(12) United States Patent
Santerre et al.

(10) Patent No.: US 12,239,758 B2
(45) Date of Patent: Mar. 4, 2025

(54) ADHESIVE DEVICE FOR BIOMEDICAL APPLICATIONS AND METHODS OF USE THEREOF

(71) Applicants: THE GOVERNING COUNCIL OF THE UNIVERSITY OF TORONTO, Toronto (CA); SUNNYBROOK HEALTH SCIENCES CENTRE, Toronto (CA)

(72) Inventors: Paul Santerre, Toronto (CA); Eli Sone, Toronto (CA); Michael Floros, Toronto (CA); Jeffrey Fialkov, Toronto (CA); Cari Whyne, Toronto (CA)

(73) Assignees: THE GOVERNING COUNCIL OF THE UNIVERSITY OF TORONTO, Toronto (CA); SUNNYBROOK HEALTH SCIENCES CENTRE, Toronto (CA)

( * ) Notice: Subject to any disclaimer, the term of this patent is extended or adjusted under 35 U.S.C. 154(b) by 430 days.

(21) Appl. No.: 17/787,552

(22) PCT Filed: Dec. 21, 2020

(86) PCT No.: PCT/CA2020/051781
§ 371 (c)(1),
(2) Date: Jun. 20, 2022

(87) PCT Pub. No.: WO2021/119853
PCT Pub. Date: Jun. 24, 2021

(65) Prior Publication Data
US 2023/0012485 A1   Jan. 19, 2023

Related U.S. Application Data

(60) Provisional application No. 62/951,810, filed on Dec. 20, 2019.

(51) Int. Cl.
*A61L 24/04* (2006.01)
*A61L 24/00* (2006.01)

(52) U.S. Cl.
CPC ......... *A61L 24/046* (2013.01); *A61L 24/0036* (2013.01)

(58) Field of Classification Search
CPC .................................................. C08G 2170/00
See application file for complete search history.

(56) References Cited

U.S. PATENT DOCUMENTS

| 3,754,285 A | 8/1973 | Greene et al. |
| 7,264,832 B2 | 9/2007 | Beckman et al. |

(Continued)

FOREIGN PATENT DOCUMENTS

| EP | 2334305 B1 | 4/2015 |
| WO | 2014/138190 A1 | 9/2014 |
| WO | 2017/044896 A1 | 3/2017 |

OTHER PUBLICATIONS

Spencer et al. Adhesive/dentin interface: the weak link in the composite restoration, Annals of biomedical engineering 38(6) (2010) 1989-2003.

(Continued)

*Primary Examiner* — Todd J Scherbel
(74) *Attorney, Agent, or Firm* — NORTON ROSE FULBRIGHT CANADA LLP

(57) ABSTRACT

An adhesive device for biomedical applications is provided comprising a support and one or more water insoluble compounds of structure 1 wherein B is an oligomer derived from a polyester, polyether, polyalkylene glycol, polysilicone or polycarbonate with a MW<10,000 g/mol, Linker L is a urethane, urea bond, or amide bond; Linker L' is a urethane or urea bond, A is a chain extender of Mw≤3000 g/mol comprising substituted or unsubstituted alkyl, cycloalkyl and/or aromatic groups, W is a terminal adhesive ben- (Continued)

Structure 1 zene-1,2-diol derivative or a terminal adhesive benzene-1,2,3-triol derivative, m is 0 or 1; and n is 0, 1, 2, 3 or 4 or a cross-linked polymer formed from said compounds. The compound(s) have a Tg lower than 25° C.

20 Claims, 29 Drawing Sheets

(56) References Cited

U.S. PATENT DOCUMENTS

| | | | |
|---|---|---|---|
| 8,119,742 | B2 | 2/2012 | Dalsin et al. |
| 8,673,286 | B2 | 3/2014 | Messersmith et al. |
| 8,916,652 | B2 | 12/2014 | Dalsin et al. |
| 9,320,826 | B2 | 4/2016 | Lee et al. |
| 9,572,910 | B2 | 2/2017 | Messersmith et al. |
| 10,045,801 | B2 | 8/2018 | Whyne et al. |
| 11,384,260 | B1 | 7/2022 | Floros et al. |
| 2010/0137903 | A1 | 6/2010 | Lee et al. |
| 2012/0029559 | A1 | 2/2012 | Lee et al. |
| 2015/0322243 | A1 | 11/2015 | Jaerger et al. |
| 2019/0022273 | A1 | 1/2019 | Hess et al. |
| 2019/0262276 | A1 | 8/2019 | Zilberman et al. |

OTHER PUBLICATIONS

Petersen et al. Tissue adhesives and fibrin glues: Nov. 2003, Gastrointestinal endoscopy 60(3) (2004) 327-333.
Spotnitz Fibrin sealant: the only approved hemostat, sealant, and adhesive—a laboratory and clinical perspective, ISRN surgery (2014).
Chivers et al. The strength of adhesive-bonded tissue joints, International journal of adhesion and adhesives 17(2) (1997) 127-132.
Lehman et al. Peripheral, Toxicity of Alkyl 2-Cyanoacrylates, Arch Sug—vol. 93, Sep. 1966, 441-446.
Wang et al. Versatile Surgical Adhesive and Hemostatic Materials: Synthesis, Properties, and Application of Thermoresponsive Polypeptides, Chemistry of Materials 29(13) (2017) 5493-5503.
Farrar. Bone adhesives for trauma surgery: A review of challenges and developments, International Journal of Adhesion and Adhesives 33 (2012) 89-97.
Sanders et al. Clinical applications of surgical adhesives and sealants, Critical Reviews™ in Biomedical Engineering 42(3-4) (2014).
Bitton et al. Phloroglucinol-based biomimetic adhesives for medical applications, Acta biomaterialia 5(5) (2009) 1582-1587.
Yu et al. Role of L-3, 4-dihydroxyphenylalanine in mussel adhesive proteins, Journal of the American Chemical Society 121(24) (1999) 5825-5826.
Lee et al. A reversible wet/dry adhesive inspired by mussels and geckos, Nature 448(7151) (2007) 338.

Lee et al. Mussel-inspired adhesives and coatings, Annual review of materials research 41 (2011) 99-132.
Waite, J. Herbert. Adhesion in byssally attached bivalves, Biological Reviews 58(2) (1983) 209-231.
Silverman et al. Understanding marine mussel adhesion, Marine biotechnology 9(6) (2007) 661-681.
Giannini et al. Effects of the solvent evaporation technique on the degree of conversion of one-bottle adhesive systems, Operative dentistry 33(2) (2008) 149-154.
Luque-Martinez et al. Effects of solvent evaporation time on immediate adhesive properties of universal adhesives to dentin, Dental Materials 30(10) (2014) 1126-1135.
Suzuki et al. Gas chromatographic estimation of occluded solvents in adhesive tape by periodic introduction method, Analytical Chemistry 42(14) (1970) 1705-1708.
Scognamiglio et al. Adhesive and sealant interfaces for general surgery applications, Journal of Biomedical Materials Research Part B: Applied Biomaterials 104(3) (2016) 626-639.
Duarte et al. Surgical adhesives: Systematic review of the main types and development forecast, Progress in Polymer Science 37(8) (2012) 1031-1050.
Forooshani et al. Recent approaches in designing bioadhesive materials inspired by mussel adhesive protein, Journal of Polymer Science Part A: Polymer Chemistry 55(1) (2017) 9-33.
Annabi et al. Surgical materials: Current challenges and nano-enabled solutions, Nano today 9(5) (2014) 574-589.
Spotnitz et al. Hemostats, sealants, and adhesives: components of the surgical toolbox, Transfusion 48(7) (2008) 1502-1516.
Vakalopoulos et al. Tissue adhesives in gastrointestinal anastomosis: a systematic review, Journal of Surgical Research 180 (2013) 290-300.
Cheung et al. Perfused culture of gingival fibroblasts in a degradable/polar/hydrophobic/ionic polyurethane (D-PHI) scaffold leads to enhanced proliferation and metabolic activity, Acta Biomaterialia 9(6) (2013) 6867-6875.
Sharifpoor et al. A study of vascular smooth muscle cell function under cyclic mechanical loading in a polyurethane scaffold with optimized porosity, Acta biomaterialia 6(11) (2010) 4218-4228.
Matheson et al. Differential effects of uniaxial and biaxial strain on U937 macrophage-like cell morphology: Influence of extracellular matrix type proteins, Journal of Biomedical Materials Research Part A 81(4) (2007) 971-981.
Matheson et al. Changes in macrophage function and morphology due to biomedical polyurethane surfaces undergoing biodegradation, Journal of cellular physiology 199(1) (2004) 8-19.
Makvandi et al. Photocurable, Antimicrobial Quaternary Ammonium-modified Nanosilica, Journal of dental research (2015) 0022034515599973.
International Search Report, International Application No. PCT/CA2020/051781, Canadian Intellectual Property Office, Feb. 23, 2021.
International Preliminary Report on Patentability, International Application No. PCT/CA2020/051781, The International Bureau of WIPO, May 17, 2022.

Structure 1

Structure 2

Structure 3

Structure 4

Structure 5

Structure 6

Structure 7

Structure 8

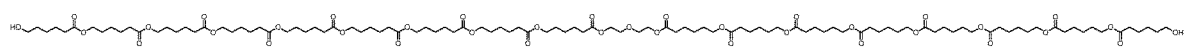
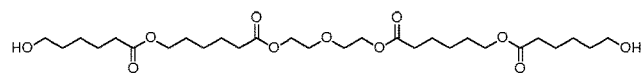
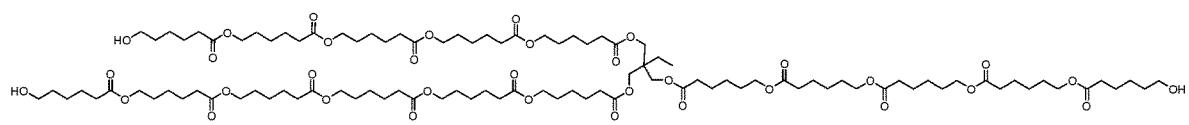
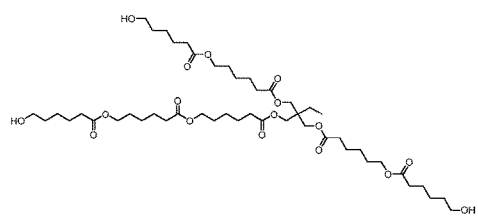
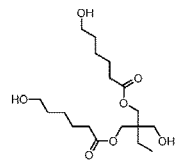
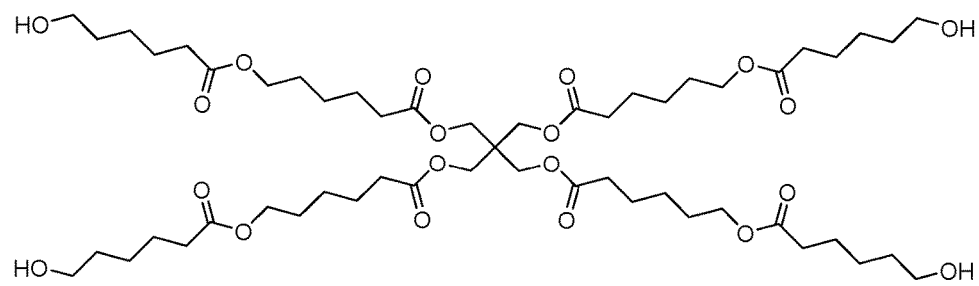
Figure 10 cont'd

Catechol Containing Compounds:

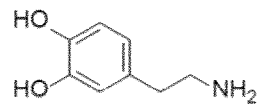

Dopamine

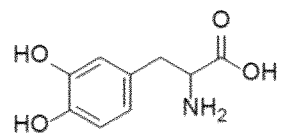

3,4-Dihydroxy-phenylalanine

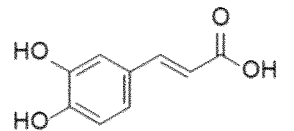

3-(3,4-Dihydroxyphenyl)-2-propenoic acid

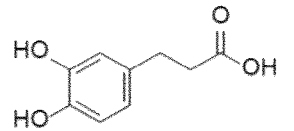

3,4-Dihydroxyhydrocinnamic acid

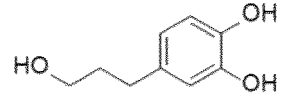

4-(3'-hydroxypropyl)catechol

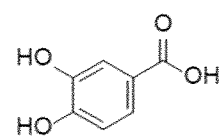

Protocatechuic acid

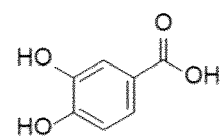

3,4-Dihydroxybenzoic acid

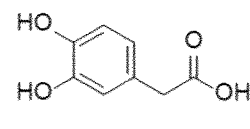

3,4-Dihydroxyphenylacetic acid

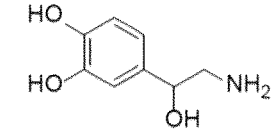

Norepinephrine

Pyrogallol based compounds:

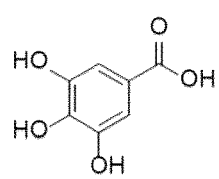

Gallic acid

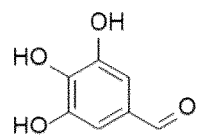

3,4,5-Trihydroxybenzaldehyde

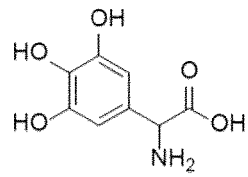

Amino(3,4,5-trihydroxyphenyl)acetic aci

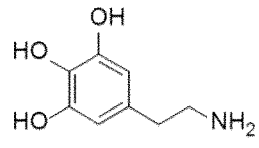

3,4,5-Trihydroxyphenethylamine

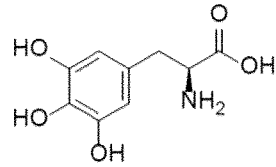

3,5-Dihydroxytyrosine

Figure 16

Activation of the dopamine hydrochloride

ADHESIVE DEVICE FOR BIOMEDICAL APPLICATIONS AND METHODS OF USE THEREOF

This application claims priority to U.S. patent application No. 62/951,810 filed Dec. 20, 2019.

FIELD OF THE INVENTION

The invention relates to adhesive devices for biomedical applications, which bond in wet and dry conditions, such as those encountered during medical procedures.

BACKGROUND

Adhesives capable of bonding in wet environments are well suited for biomedical applications. However, most commercially available adhesives suffer major compromises in bond strength, curing time and/or biocompatibility, rendering them inappropriate for many clinical applications. Conventional adhesives generally require clean, dry surfaces for optimal performance which renders them ineffective for binding in wet environments. Furthermore, the vast majority of conventional adhesives are not biodegradable or resorbable and lack suitable mechanical properties to be used as tissue adhesives or sealants. This has greatly limited the application of surgical adhesives in biomedical applications.

Dental adhesives such as glass ionomer cements (GICs), two-part epoxies and light-cured methacrylate resin systems are generally toxic, slow curing, and require an external light source, acid etching, multiple cure cycles and/other multi-step surface pretreatment techniques. Due to the toxicity and/or extensive preparation required for these materials, they have not been approved for use outside of oral applications where the lack of alternative wet adhesives have necessitated their use [1].

Adhesives which have been approved for clinical use include fibrin, cyanoacrylate, gelatin-resorcin formaldehyde/glutaraldehyde, and PEG-based glues. These adhesive systems all are limited by low bonding under wet conditions and/or poor cytocompatibility [2-9].

PEG-based adhesives, which are extensively used, are relatively non-degradable and are associated with adverse swelling issues which can cause nerve and organ damage [8].

Catechol-containing polymeric adhesives inspired by aquatic marine mussels are of interest due to the natural ability of mussels to bind to a multitude of surfaces under heavily biofouled conditions. Mussel adhesion is reversible and capable of withstanding fluctuations in temperature and ionic strength [10-12]. The four main components of the mussel adhesive are: 1) acid mucopolysaccharides which act as primers; 2) adhesive proteins consisting mainly of polyphenolic proteins rich in the catechol 3,4-dihydroxyphenylalanine (L-DOPA) and lysine; 3) fibrous proteins that act as an attachment thread between mussel and substrate; and 4) polyphenoloxidase to promote intermolecular cross-linking [13, 14].

Branched PEG and grafted catechol-containing polymer derivatives have demonstrated adhesion to biological tissues, but the requirement for solvents and long curing durations renders them unsuitable for most clinical applications [15-18]. In general, these systems are composed of non-degradable polymers and require the use of solvents which may be toxic and impede curing and bonding of the adhesive. Solvent removal is further required for the adhesives to function optimally and is generally accomplished by evaporation or other means of removal. The lengthy duration of the solvent removal process (on average lasting up to multiple days) is an important consideration when designing biocompatible adhesives [6, 19].

U.S. Pat. No. 8,673,286 discloses poly(alkylene oxide) adhesives using branched (10-20 kDa-PEG)$_4$ backbones, functionalized with DOPA$_4$, DOPA-Boc, DOPA$_3$-Lys$_2$, DOHA or DOPA with ester or urethane linkages. These adhesives must be solubilized in PBS and mixed in situ by hand in the presence of a water-solubilized oxidant (NaIO$_4$) prior to use.

PCT Pat. Appl. Publ. No. WO 2017/044896 discloses high molecular weight water soluble adhesives made of linear and branched structures made from PEG or PEGylated polyols, functionalized internally with DOPA using isocyanates. The disclosed formulations require the use of large amounts of filler material, such as dicalcium phosphate, to increase the mechanical properties of the adhesive. The adhesives further include long PEG segments which are non-biodegradable as well as hexamethyl diisocyanate which can produce toxic alkyl diamine biproducts when degraded.

U.S. Pat. No. 8,916,652 discloses branched structures made from PEG-based polyol oligomers. Structures described in the patent are functionalized internally with DOPA, DOPA-Lys, or DOHA using amide/urea linkages. Several disclosed formulations further contain ester or urethane linkages within the branches. All of these disclosed formulations, however, require the use of solvent for application; the adhesives are prepared for use by separately dissolving the polymer and NaIO$_4$ as a crosslinking agent in PBS and mixing at a ratio of 1:1 before being spread onto the surface using a spray apparatus.

US Pat. Appl. Publ. No. 2010/0137903 discloses substrates (e.g. films, meshes, etc.) which are treated with high molecular weight bioadhesives based on branched PEG oligomers for use in hernia repairs. Application of these adhesives onto substrates requires a curing procedure in which a first oxidant is added to the adherend substrate and then a weight is placed over the adhesive interface and held stationary for at least 1 hour. In some cases, a second application of oxidant is employed. A prolonged application period as described in this application is not practical or possible in most surgical procedures.

U.S. Pat. No. 8,754,285 B2 discloses the synthesis of thin films designed to adhere to a wide assortment of surfaces. The polymer adhesives consist of PCL, PEG and DOPA groups linked through ester and urethane linkages. Although these catechol-containing hydrogels have demonstrated pH-triggered curing and have potential for use as surgical adhesives [20], their complex preparation (constant stirring and careful pH control) limits their practical clinical applications. Furthermore, the adhesives disclosed in the patent use toxic solvents, which are of significant concern for in vivo translation. Furthermore, the complexity of this application process is significant, and much more difficult than the current standard of care.

All of the above adhesives suffer from similar disadvantages selected from complex, application strategies involving solvents. Organic solvents are required for application, and spreading and surface penetration strategies may be required. These limitations highlight the need for alternate adhesives which perform in wet conditions; have low toxic reactivity with cells, are easy to apply and are biodegradable; and yet have sufficient mechanical properties for given needs. Further, there is a need for adhesive devices such as tapes that are stable and convenient to use.

BRIEF SUMMARY

The present disclosure provides:
In a first embodiment, a device comprising: a support; and a water insoluble adhesive on at least one bonding site on a surface of the support; the adhesive comprises:
 a compound of structure 1

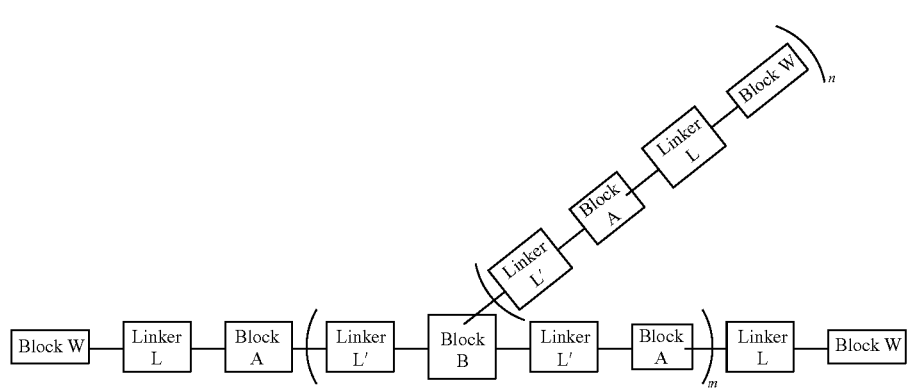

Structure I wherein
the compound is water insoluble;
the compound has a Tg lower than 25° C.;
B is a branched or unbranched oligomer derived from a polyester, polyether, polyalkylene glycol, polysilicone or polycarbonate with a MW<10,000 g/mol; Linker L is an urethane, urea bond, or amide bond;
Linker L' is an urethane or urea bond;
A is a chain extender of Mw≤3000 g/mol comprising substituted or unsubstituted alkyl, cycloalkyl and/or aromatic groups;
W is a terminal adhesive selected from an adhesive benzene-1,2-diol derivative or an adhesive benzene-1,2,3-triol derivative;
m is 0 or 1; and
n is 0, 1, 2, 3 or 4; or
a cross-linked polymer produced by cross-linking compounds of structure 1.

2. The device of embodiment 1, wherein the adhesive comprises a compound of structure 1 and a cross-linking agent, wherein the cross-linking agent promotes covalent crosslinking of the terminal adhesive with another terminal adhesive and/or of the terminal adhesive with tissue.

3. The device of embodiment 1 wherein the adhesive comprises a cross-linked polymer prepared by combining the compound of structure 1 with a crosslinking agent or a curing agent preferably selected from sodium carbonate and/or iron(III) salts.

4. The device of any preceding embodiments, wherein the adhesive is hydrolysable and/or enzyme degradable.

5. The device of embodiment 4 wherein the device is hydrolysable and/or enzyme degradable.

6. The device of any preceding embodiments, wherein the support comprises a plurality of surfaces each having at least one bonding site thereon.

7. The device of any preceding embodiments, wherein the support comprises a biocompatible sheet structure.

8. The device of embodiment 7, wherein the biocompatible sheet structure is a biodegradable and/or bioresorbable polymer material.

9. The device of embodiment 7 or 8 wherein the support comprises a plurality of bonding sites and wherein the bonding sites include pores extending through the biocompatible sheet structure, and wherein the adhesive fills the pores.

10. The device of embodiment 7 or 8, wherein the sheet comprises first and second opposed sheet surfaces and the first sheet surface is coated with the adhesive.

11. The device of embodiment 7 or 8, wherein the sheet comprises first and second opposed sheet surfaces and both the first and second opposed sheet surfaces are coated with the adhesive.

12. The device of any preceding embodiments, wherein the support is translucent.

13. The device of any preceding embodiments wherein the device is an implant.

14. The device of any preceding embodiments, further comprising one or more removable protective sheets for covering an adhesive surface of the device.

15. The device of any preceding embodiments, wherein B is an oligomer derived from polycaprolactone, polydimethylsiloxane, polypropylene glycol or polyhexamethylene carbonate, preferably polycaprolactone.

16. The device of any preceding embodiments, wherein the support comprises a polymer selected from polyesters, polylactides and polycarbonates, preferably polycaprolactone.

17. The device of any preceding embodiments, wherein the adhesive comprises two or more different compounds of structure 1 or comprises a cross-linked polymer produced by cross-linking two or more different compounds of structure 1.

18. A method of adhering a first surface and a second surface comprising: applying an adhesive device according to any preceding embodiments to at least a portion of at least one of the first and second surfaces; and bringing at least a portion of the first and second surfaces into contact with each other and/or bringing at least a portion of the first and second surfaces into contact with the adhesive device.

19. The method of embodiment 18 wherein at least one of the first and second surfaces is a wet surface, saline surface and/or a surface contaminated with proteins and/or biomolecules.

20. The method of embodiment 18 or 19 wherein the first surface comprises soft tissue and the second surface comprises hard tissue or a part of an implant or device.

21. The method of embodiment 18 or 19 wherein the first surface comprises hard tissue and the second surface comprises a part of an implant or device or hard tissue.

22. The method of any preceding embodiments further comprising applying an external energy source to the adhesive and/or at least one of the first and second surface to enhance crosslinking in situations where crosslinkers benefit from an external energy source to facilitate complete or rapid action.

23. A method of stabilizing a surface comprising applying an adhesive device as provided herein to the surface.

BRIEF DESCRIPTION OF THE DRAWINGS

These and other features of the preferred embodiments of the invention will become more apparent in the following detailed description in which reference is made to the appended drawings wherein:

FIG. 16 shows an exemplary list of 4-alkylbenzene-1,2-diol derivative and a 5-alkylbenzene-1,2,3-triol derivative that may be used for the preparation of the compounds suitable for use in devices of the present disclosure according to an embodiment;

DETAILED DESCRIPTION

Figure 1:
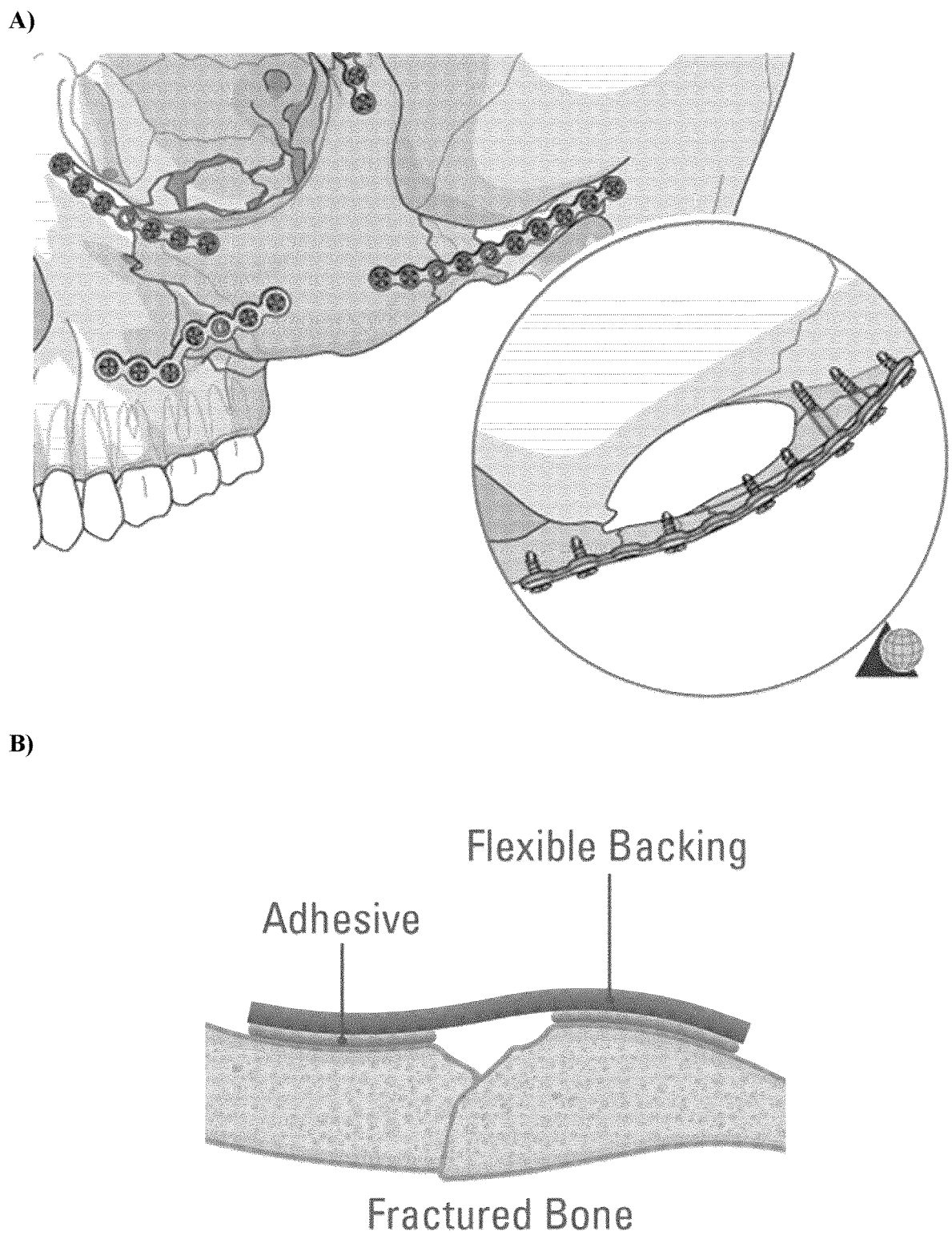
FIG. 1 shows A) a representation of a current rigid metal plate and screw fixation system fixing a craniomaxillofacial fracture, and B) a device of the present disclosure according to an embodiment consisting of a flexible backbone polymer and an adhesive stabilizing a bone fracture.

For further clarity, the following terms are defined:

Wet conditions encompass environments which include, but are not limited to, water, water with proteins and/or salts and/or blood and/or other biological macromolecules.

Physiological conditions refer to wet conditions at pH 7.4±0.3 and temperature of 37.5±3° C.

Water insoluble is defined as the ability of a material to resist dissolution and/or the formation of a heterogenous mixture when a solvent-free material is mixed with water in concentrations greater than 0.5 wt/wt % at physiological temperatures (37.5±3° C.). Visible particles of the materials will remain separate and heterogeneous as a solid or gel when the material is hand mixed in water at a concentration of 0.5 wt/wt % at physiological temperatures (37.5±3° C.).

Crosslinking is defined as the formation of a chemical bond, inclusive of covalent bonding and chelation, between two existing macromolecules (for example: adhesive-adhesive crosslinking, adhesive-protein crosslinking).

Curing is defined as the chemical process of converting a macromolecule into a higher molecular weight polymer via crosslinking reactions.

Setting is defined as an irreversible change in the state of a material, from flowable to rigidified, which occurs during curing.

Implant is defined as any material that is designed to function in contact with the human body.

Tm (Melting temperature) is defined as the temperature (or temperature range) at which a well defined first order transition occurs, as determined by an endothermic event in a differential scanning calorimetry thermogram. If there is no such transition, as is common for amorphous materials, Tm will be defined by the beginning of the substance's ability to flow or spread under an applied force (i.e., temperature within the linear viscoelastic region on a stress-sweep viscoelastic curve at which the viscous modulus>elastic modulus (tan $\delta$>1)).

Tg (Glass transition temperature) is defined as the temperature (temperature range) where the polymer transitions from a hard, glassy material to a soft, rubbery material as determined by changes in the heat capacity (Cp), reversible heat flow curves, and material rigidity or hardness obtained from differential scanning calorimetry, dynamic mechanical assessment and needle penetrometer or indentation experiments, respectively.

In the present disclosure, soft tissue refers to connective and/or fatty and/or fibrous soft tissues and/or any organ tissue consisting primarily of low calcified content relative to biomolecule content (e.g. collagens, glycosamino glycans, elastin, etc). Soft tissues connect, surround, or support bones, organs and other structures in the body. In one embodiment, soft tissues refer in particular to sub-epidermal fatty and/or fibrous tissues.

Examples of soft tissues include tendons, muscles, skin, ligaments, nerves, vessels, fascia, fibrous tissues and synovial membranes. In another embodiment soft tissues make up the protein base structures of vital organs such as the heart, blood vessels, intestines, etc.

In the present disclosure, hard tissues are mineralized and rigid tissues containing significant amounts of hydroxyapatite. Examples of hard tissues include bone, enamel, dentin and cementum.

The present disclosure provides a device comprising a water insoluble adhesive that may be used to glue or secure hard tissue to hard tissue, hard tissue to implant, hard tissue to soft tissue, soft tissue to soft tissue, soft tissue to implant or implant to implant.

The use of devices described in the present disclosure may eliminate or reduce the need to use staples, sutures, tacks, screws or the like to secure or repair damaged tissues or to secure implants or devices within or on the body.

Many previously described adhesives are comprised of polymeric chains that are decorated with periodic or randomly distributed branching side chains containing adhesive functional groups. This contributes to high intermolecular bonding (requiring solvents to assist with application and surface wetting) and poor accessibility of adhesive functional groups to the substrates where adhesion is desired.

Adhesives described in the present disclosure when compared to known bioadhesives may be characterized by a rapid high degree of surface wetting/adhesion in a biological environment, easy adherence and retention of the water insoluble adhesive to substrates, and/or elimination of solvent requirement. Such biological environment may reflect the constraints of biological elements (protein, aqueous fluids, temperature, fatty tissue, bony tissue, cells, etc.).

The present disclosure describes devices comprising water insoluble adhesive compounds consisting of short linear or short branched oligomer chains capped only at their terminal ends with phenyl moieties with two or three hydroxyl groups acting as adhesive moieties as well as well as cross-linked polymers prepared from these compounds. The oligomer chains may have a MW between 50 and 5,000 g/mol, in other embodiments, between 50 g/mol, 100 g/mol, 500 g/mol or 1000 g/mol and 5,000 g/mol, in other embodiments between 50 g/mol, 100 g/mol, 500 g/mol or 1000 g/mol and 3,000 g/mol. The water insoluble adhesive may be prepared in such way that it will degrade over a period of time when exposed to biological conditions. Alternatively, the water insoluble adhesive may be non-degradable when exposed to biological conditions.

The present disclosure provides devices comprising water insoluble adhesives which are biocompatible and non-toxic; wherein biocompatible refers to a material which does not induce an observable biological response (e.g. immunological) upon contact with cellular, tissue or other bodily fluids/components [21], and non-toxic refers to a material which does not have an observable negative effect on cell viability. Furthermore, when the compounds of the water insoluble adhesive are tailored to be degradable, the degradation products are biocompatible and non-toxic.

Having adhesive moieties at the terminal ends, while not bound by theory, the compounds of the present disclosure allow the adhesive moieties to preferentially orient to the substrate surface with minimal steric hindrance, and therefore rapid adhesion. Terminal functionalization of adhesive moieties onto the oligomeric backbone may also allow structural control, as many internally functionalized block or grafted polymers have adhesive moieties randomly oriented off of the backbone. Terminal grafting may also reduce the viscosity of the adhesives, as their bulk disrupts packing, reducing intermolecular forces.

Suitably the oligomers have a MW<10,000, preferably <5,000 g/mol or <3000. The use of oligomers with a Mw<5,000 g/mol, and especially a Mw<3,000 g/mol greatly reduces intermolecular interactions associated with them due to smaller size and reduced cumulative forces between oligomers. The reduction in intermolecular interactions between the oligomers of the compound of structure 1 may allow the adhesive described herein to be prepared without the use of a solvent resulting in faster setting/curing, low/no toxicity and improved usability of the adhesive, as solvent has been reported to interfere with adhesive bonding and presents its own toxicity concerns [22-25]. In some embodiments, the oligomer suitably has a molecular weight>50 g/mol, >100 g/mol, >300 g/mol or greater than 500 g/mol.

It is well accepted that adhesive devices for use in biomedical applications ideally may have some or many of the following characteristics [26-31]:
bond rapidly or on demand when in contact with a surface
cure in a controllable manner
work over a suitable range of temperatures
adhere to materials without the necessity of pre-treatment or cleaning
exhibit adhesion strength which is maintained over the duration of the desired application
have strong bonding and curing strength
are biodegradable
obviate the need for a solvent
have no smell
achieve desirable aesthetic properties are easy to work with and easy to apply
easy to incorporate a catalyst to achieve curing, or cures without catalyst
are easy and inexpensive to manufacture
work well in wet, dry and situations where contaminants may be present Depending on the structure, the Mw, and the formulation of the adhesive compounds used in the present disclosure as well as the properties of the associated support, the adhesive devices described in the present disclosure may have at least one of the criteria listed above.

Water Insoluble Adhesives for Use in Adhesive Devices

Figure 2:
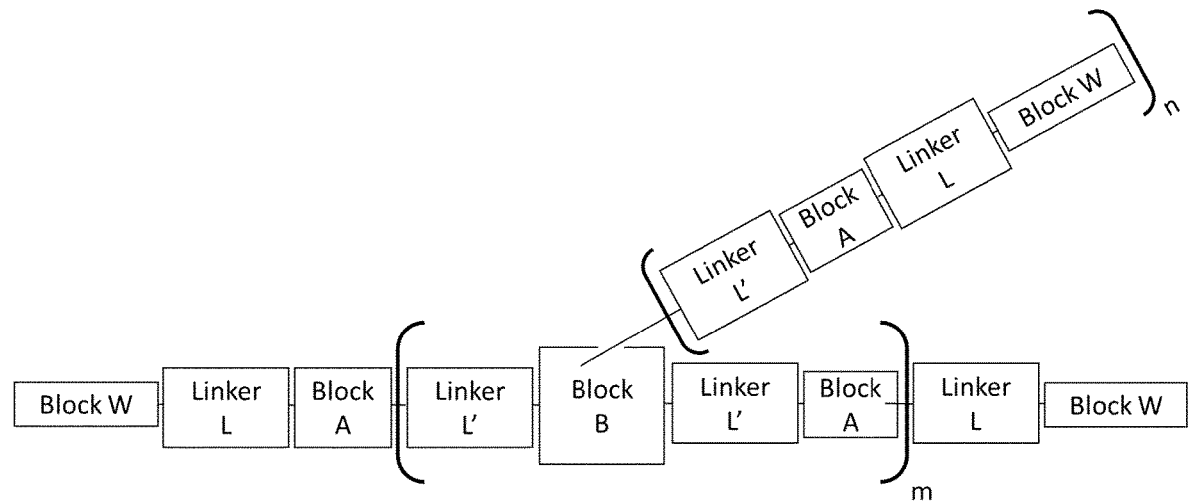
FIG. 2 shows compound of Structure 1 suitable for use in a device according to an embodiment.

According to an embodiment, the water insoluble adhesive comprises, consists of or consists essentially of a compound of structure 1 (FIG. 2) wherein B is an oligomer, Linker L is a urethane, urea bond, or amide bond; Linker L' is a urethane or urea bond, A is a chain extender, W is a terminal adhesive moiety, m is 0 or 1; and n is 0, 1, 2, 3 or 4.

Water insolubility can be rendered by assembling an adhesive using B and A components which are themselves water insoluble. Alternatively, water insolubility can be rendered by assembling an adhesive using B and A components which are themselves water soluble but which, upon reaction, undergo increases in their hydrophobic character due to reactive conversion of some or all of the water-soluble functional groups (such as hydroxyl or amine groups).

Figure 3:
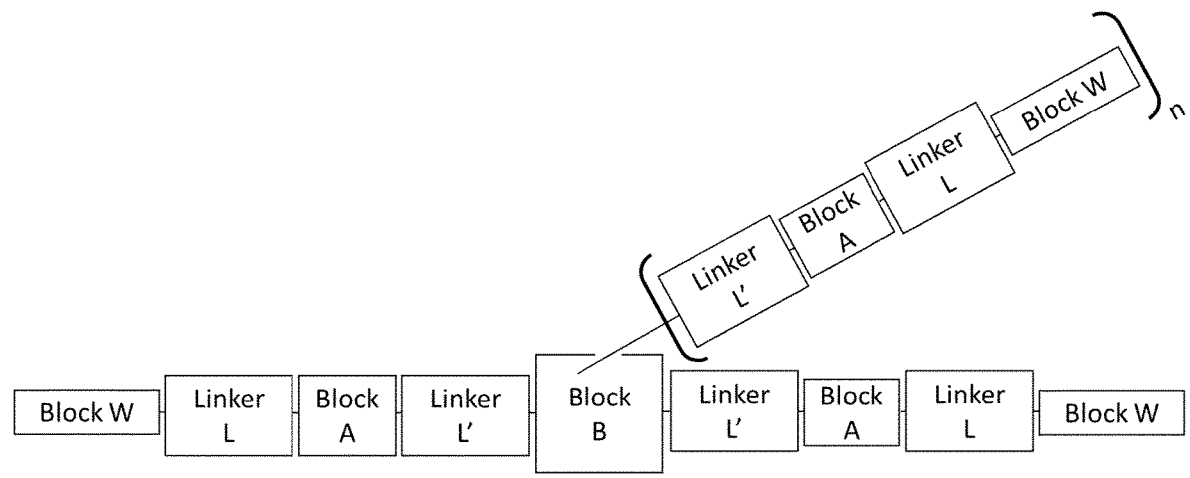
FIG. 3 shows compound of Structure 2 suitable for use in a device according to an embodiment.

According to an embodiment, the compound of structure 1 has m=1 resulting in the compound of structure 2 (FIG. 3).

Figure 4:
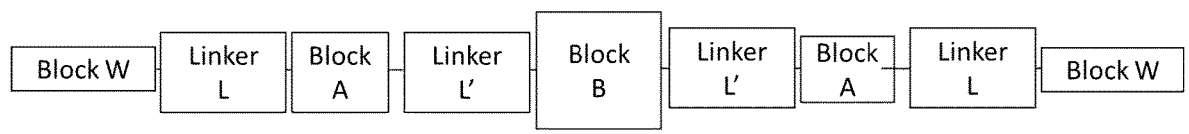
FIG. 4 shows compound of Structure 3 suitable for use in a device according to an embodiment

According to an embodiment, the compound of structure 1 has m=1 and n=0 resulting in the compound of structure 3 (FIG. 4).

Figure 5:
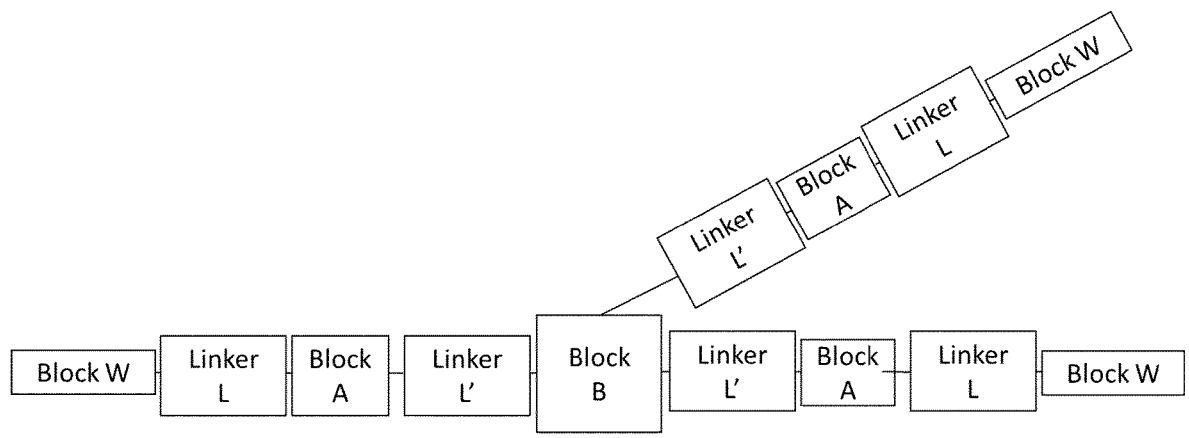
FIG. 5 shows compound of Structure 4 suitable for use in a device according to an embodiment.

According to an embodiment, the compound of structure 1 has m=1 and n=1 resulting in the compound of structure 4 (FIG. 5).

Figure 6:
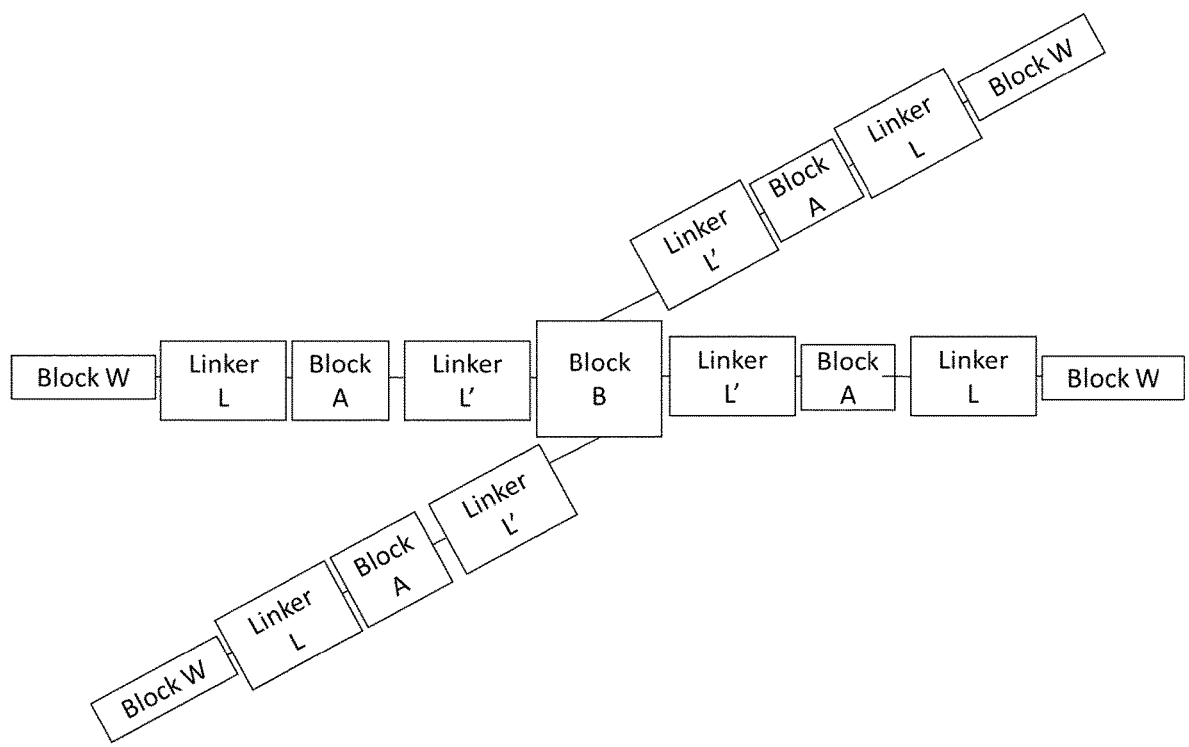
FIG. 6 shows compound of Structure 5 suitable for use in a device according to an embodiment.

According to an embodiment, the compound of structure 1 has m=1 and n=2 resulting in the compound of structure 5 (FIG. 6).

Figure 7:
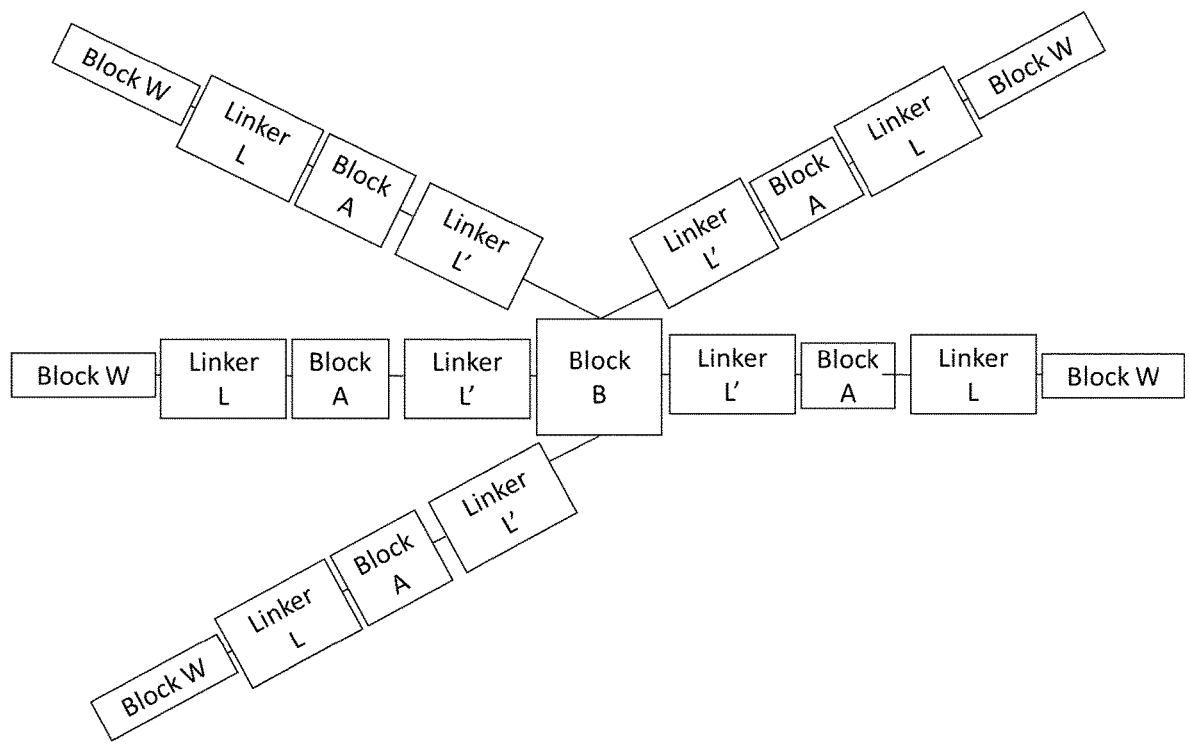
FIG. 7 shows compound of Structure 6 suitable for use in a device according to an embodiment.

According to an embodiment, the compound of structure 1 has m=1 and n=3 resulting in the compound of structure 6 (FIG. 7).

Figure 8:
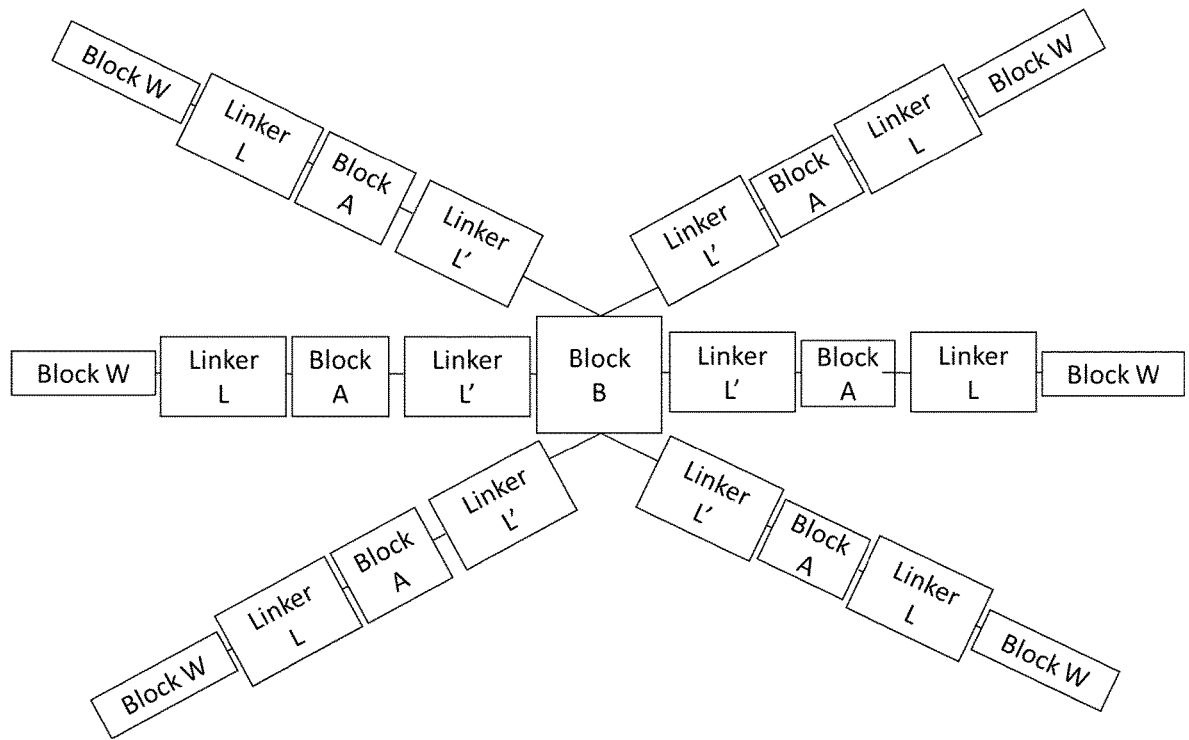
FIG. 8 shows compound of Structure 7 suitable for use in a device according to an embodiment.

According to an embodiment, the compound of structure 1 has m=1 and n=4 resulting in the compound of structure 7 (FIG. 8).

Figure 9:
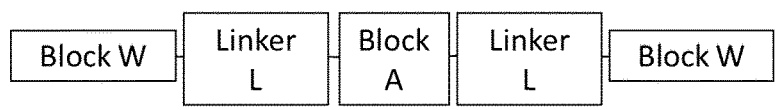
FIG. 9 shows compound of Structure 8 suitable for use in a device according to an embodiment.

Alternatively, according to an embodiment, the compound of structure 1 has m=0 resulting in the compound of structure 8 (FIG. 9).

Block B is an oligomer having a MW between 50 g/mol and 5,000 g/mol, In various embodiments, between 50 g/mol, 100 g/mol or 500 g/mol and 2000 g/mol, 3000 g/mol or 5000 g/mol. Preferably, the oligomer may have a Mw<3,000 g/mol. The Block B may be derived from any suitable biocompatible polymers such as, but not limited to fluoropolymers, polyesters, polyethers, polyalkyloxide, polyurethanes, polyamides, polysilicone, polycarbonate, or polysaccharides selected such that the compound of structure 1 is water insoluble. According to an embodiment, the Block B is an oligomer derived from polycaprolactone, polydimethylsiloxane, polypropylene glycol or polyhexamethylene carbonate. As used herein, an oligomer "derived from" an identified polymer retains the essential structure and activity of the polymer despite any modifications thereto. In various embodiments, the oligomer is selected from the identified biocompatible polymers.

According to an embodiment, the compound of structure 1 may have a Block B which is either hydrolysable or enzyme degradable under physiological conditions. Alternatively, the Block B may be non-degradable under physiological conditions.

Block B may have a finite number of branches resulting in compounds of Structure 1 or Structure 2 or more particularly compounds of Structure 4, Structure 5, Structure 6 or Structure 7. Alternatively, Block B may be linear resulting in compounds of Structure 3.

According to an embodiment, Block B may be derived from small molecules such as monomers, dimers or trimers. Such monomers, dimers and trimers may be derived from polyhydric alcohols including but not limited to trimethylolpropane, glycerol and pentaerythritol; or from their alkoxylated derivatives.

According to an embodiment, the water insoluble adhesive of may be a compound of structure 8 for which Block B is absent.

Linker L is a urethane bond, a urea bond or an amide bond and Linker L' is either a urethane bond or a urea bond. According to an embodiment, the compound of structure 1 may be designed to render Linker L and/or Linker L' hydrolysable or enzyme degradable. Alternatively, the Linker L and/or Linker L' may be non-degradable under physiological conditions.

Block A is a chain extender comprising substituted or unsubstituted alkyl, cycloalkyl and/or aromatic groups. Block A has a Mw between 20 and 3000 g/mol in some embodiments, between 20 and 65 g/mol, 100 g/mol, 200 g/mol, 500 g/mol, 1000 g/mol or 2000 g/mol. According to an embodiment, Block A is a substituted or unsubstituted alkyl group. According to an embodiment, Block A is a substituted alkyl group, wherein one or more of the hydrogens on the alkyl are replaced, introducing branching. According to an embodiment, Block A may be substituted with C1-C6 carboxylate group. According to another embodiment, Block A is a methyl hexanoate or ethyl hexanoate.

Block W is a terminal adhesive moiety having a phenyl with at least two hydroxyl groups. According to an embodiment, Block W is a terminal adhesive moiety derived from benzene-1,2-diol derivative or benzene-1,2,3-triol derivative. Biologically derived and inspired molecules containing benzene-1,2-diol or benzene-1,2,3-triol derivatives have strong and durable adhesion to various substrate surfaces including wet surfaces. These characteristics are advantageous for the preparation of adhesive molecules for biomedical applications. According to an embodiment, Block W may be a 4-alkylbenzene-1,2-diol derivative. Alternatively Block W may be a 5-alkylbenzene-1,2,3-triol derivative. According to an embodiment, Block W may have a structure selected either Structure 9 or Structure 10 wherein R may be present or absent. When R is present, R may be a C1-C6 alkyl group or C1-C6 alkene optionally substituted with OH, NH or C1-C6 alkyl.

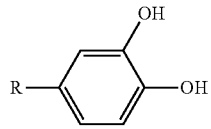

Structure 9

-continued

Structure 10

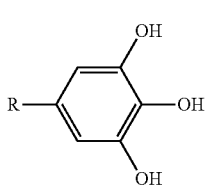

According to some embodiments, the water insoluble adhesives used comprise a compound suitably having a Tg lower than or equal to 25° C., in one embodiment lower than or equal to 20° C. prior to cross-linking.

According to an embodiment, the water insoluble adhesives used in devices according to the present disclosure may have an adhesive strength greater than 10 kPa under compression, tensile, or tensile lap shear testing. According to other embodiments, the adhesives may have an adhesive strength greater than 25 kPa, 50 kPa, greater than 75 kPa or greater than 100 kPa under compression, tensile, or tensile lap shear testing. Water insoluble adhesives according to disclosed embodiments that have an adhesive strength between 10 kPa and 25 kPa may have particular utility in applications where it is beneficial to have a water insoluble adhesive that is relatively flexible, including applications involving the adhesion of soft tissues and, in particular, skin. According to an embodiment, the water insoluble adhesives used in devices according to the present disclosure may comprise a plurality of compounds derived from the compound of structure 1 with additional admixture(s) whose function may include directly enhancing the adhesive performance (for example, but not limited to polymers, cross-linking agents, fillers and porogens), and/or to provide combination products with further value add (for example, but not limited to drugs, fillers, therapeutics, regenerative materials or other compounds).

According to an embodiment, the water insoluble adhesives used in devices of the present disclosure may comprise a plurality of compounds derived from the compound of structure 1. The water insoluble adhesives may comprise a compound of structure 1 having m=0 and another compound of structure 1 having m=1 and n is either 0, 1, 2, 3 or 4. More particularly, the water insoluble adhesives may comprise a compound of structure 1 having m=0 and another compound of structure 1 having m=1 and n is 0.

According to an embodiment, the water insoluble adhesives used in devices of the present disclosure may comprise a compound of structure 1 having m=1 and n=0 and another compound of structure 1 having m=1 and n is 0, 1, 2, 3 or 4. More particularly, the water insoluble adhesives may comprise a compound of structure 1 having m=1 and n=0 and another compound of structure 1 having m=1 and n=1. According to another embodiment, the water insoluble adhesives of the present disclosure may consist essentially of compounds of structure 1.

According to preferred embodiments, the water insoluble adhesives used in devices of the present disclosure further comprise a crosslinking agent or a curing agent. In order to achieve a desirable mechanical property and desired setting speed, in some embodiments, the water insoluble adhesive can benefit from the inclusion of crosslinking agents or curing agents. In one embodiment, the setting speed is ≤5 hours. In another embodiment, the setting speed is ≤2 hours. In another embodiment, the setting speed is ≤60 minutes. In another embodiment, the setting speed is ≤15 minutes. In another embodiment, the setting speed is ≤5 minutes. In another embodiment, the setting speed is ≤2 minutes. In another embodiment, the setting speed is ≤1 minute. In another embodiment, the setting speed is ≤30 seconds. In another embodiment, the setting speed is ≤10 seconds. The use of such agents may improve the rigidity and cohesive strength of the adhesives while reducing creep and deformation. 4-alkylbenzene-1,2-diol derivative or a 5-alkylbenzene-1,2,3-triol derivative may be chelated with the use of suitable complexing agents (e.g. Fe(III) salts), and/or irreversibly crosslinked via the use of oxidants, light, basic pH, and enzymes. In some embodiments, the compounds of Structure 1 may have a lower Tg or melting point than the operational temperature. Under such conditions, a curing agent or crosslinking agent is useful to rigidify the adhesives, providing increased cohesive strength. When a crosslinking agent such as an oxidant or a chelating agent is included within the water insoluble adhesive, it may promote covalent crosslinking of the catechol groups with other catechols and/or tissue.

According to an embodiment, the water insoluble adhesives described for use in devices of the present disclosure comprise compounds of structure 1 having a Mw<5,000 g/mol and a Tg lower than 20° C. rendering optional the use of a solvent; alternatively the water insoluble adhesive comprises compounds of structure 1 having a Mw<5,000 g/mol and a Tg lower than 20° C. rendering optional the use of a solvent; and alternatively the water insoluble adhesive of the present disclosure comprises compounds of structure 1 having a Mw<3,000 g/mol and a Tg lower than 20° C. rendering optional the use of a solvent. According to another embodiment, the water insoluble adhesives may be solvent free.

The solvent-optional or solvent-free nature of the water insoluble adhesive of the present disclosure is advantageous as numerous solvents are known to be toxic and may impede with the bonding of the adhesive to the substrate and may even interfere with the crosslinking and curing process if crosslinking agents or curing agents are used. For example, it is known that adhesives dissolved in solvents typically have reduced cohesive and adhesive properties and rely on diffusion or evaporation of the solvent for improved mechanical performance. Depending on the environment and the nature of the solvent, this diffusion or evaporation of the solvent may be on the order of minutes, hours, days or even longer periods of time. Solvents have been known to cause toxicity or other undesirable effects including intoxication and strong odors [31-32]. Furthermore, using a water insoluble adhesive that does not require a solvent is advantageous for biomedical applications as it alleviates the need for the solvent to evaporate, diffuse or be removed by another mechanism, which are frequent requirements when an adhesive system includes a solvent The latter events are usually accomplished over an extended time period that may occur over hours or even multiple days, creating very long setting times and limiting the biomedical applications and use of said adhesive formulations.

Methods of Preparing Water Insoluble Adhesives for Use in Adhesive Devices

The compound of structure 1 may be prepared according to a method comprising the steps of:
1. reacting an amino or alcohol group present at each of at least two end portions of an oligomer with one of two isocyanate groups of a diisocyanate molecule. The diisocyanate has a substituted or unsubstituted alkyl-derived chain extender, a substituted or unsubstituted cycloalkyl-derived chain extender, or a substituted or unsubstituted benzyl-derived chain extender sandwiched between the two isocyanate groups;

2. reacting the second isocyanate of the diisocyanate molecule with an amine group, alcohol group or carboxy group present on an alkyl chain of a 4-alkylbenzene-1,2-diol derivative or a 5-alkylbenzene-1,2,3-triol derivative.

The compound of structure 8 may be prepared by a method comprising the step of reacting each isocyanate group of a diisocyanate with an amine group, alcohol group or carboxy group present on an alkyl chain of a 4-alkylbenzene-1,2-diol derivative or a 5-alkylbenzene-1,2,3-triol derivative. The diisocyanate has a substituted or unsubstituted alkyl-derived chain extender, a substituted or unsubstituted cycloalkyl-derived chain extender, or a substituted or unsubstituted benzyl-derived chain extender between the two isocyanate groups.

According to an embodiment, the oligomer backbone has a Mw of about <5,000 g/mol, <5,000 g/mol or <3,000 g/mol. The oligomer may be non-degradable. Alternatively, the oligomer may be hydrolysable or enzyme degradable under physiological conditions. The oligomer may be branched or unbranched and may be derived from any suitable water insoluble polymer or a soluble polymer that in combination with block A yields a water insoluble compound of structure 1 that is currently used in implant devices and known to those skilled in the art, such as, but not limited to, fluoropolymers such as PTFE and ETFE, polyethers, polyesters (PLA, PGA, PCL), polyalkyloxide (PEG, PPG), polyurethanes, polyamides, polysilicone (PDMS), polycarbonate (PCN), polyketones (PK), polyacetals (POM), polyolefins or polysaccharides (chitin, chitosan). More, particularly, the oligomer may be derived from a polyester, polyether, polyalkyloxide, polysilicone or polycarbonate. In a preferred embodiment, the oligomer may be derived from polycaprolactone, polydimethylsiloxane, polypropylene glycol, or polyhexamethylene carbonate. While the term oligomer is used, in some embodiments, there are no repeating units i.e. B comprises a single monomeric unit, which has the essential structure and activity of the identified polymers.

According to an embodiment, the oligomer may be linear, resulting in compounds of Structure 3. Alternatively, the oligomer may be branched resulting in compounds of Structure 4, Structure 5, Structure 6 or Structure 7.

Figure 10:
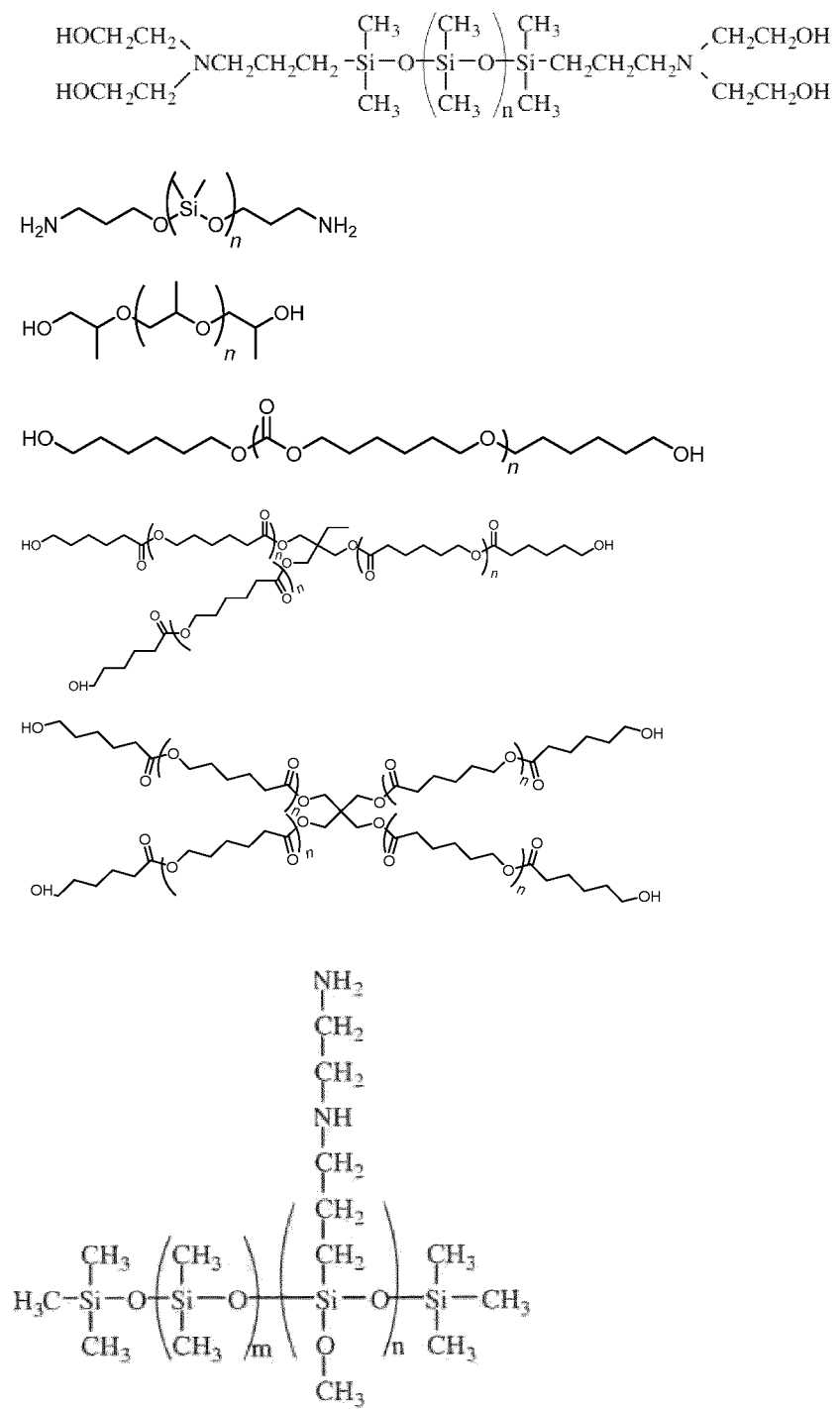
FIG. 10 shows an exemplary list of commercially available monomers or oligomers that may be used for the preparation of compounds suitable for use in devices of the present disclosure according to an embodiment.
Figure 11:
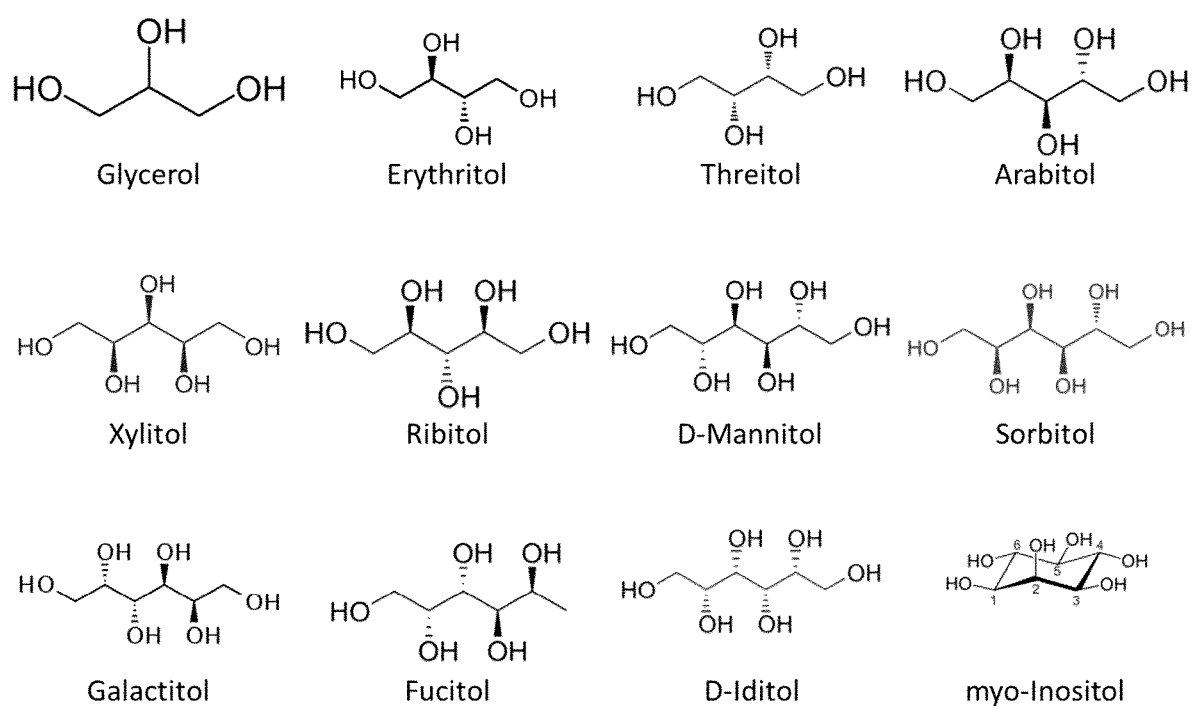
FIG. 11 shows an exemplary list of polyalcohols and sugar alcohols that may be used as a starting point for the preparation of the oligomer for adhesives for use in preparing adhesive devices of the present disclosure.
Figure 12:
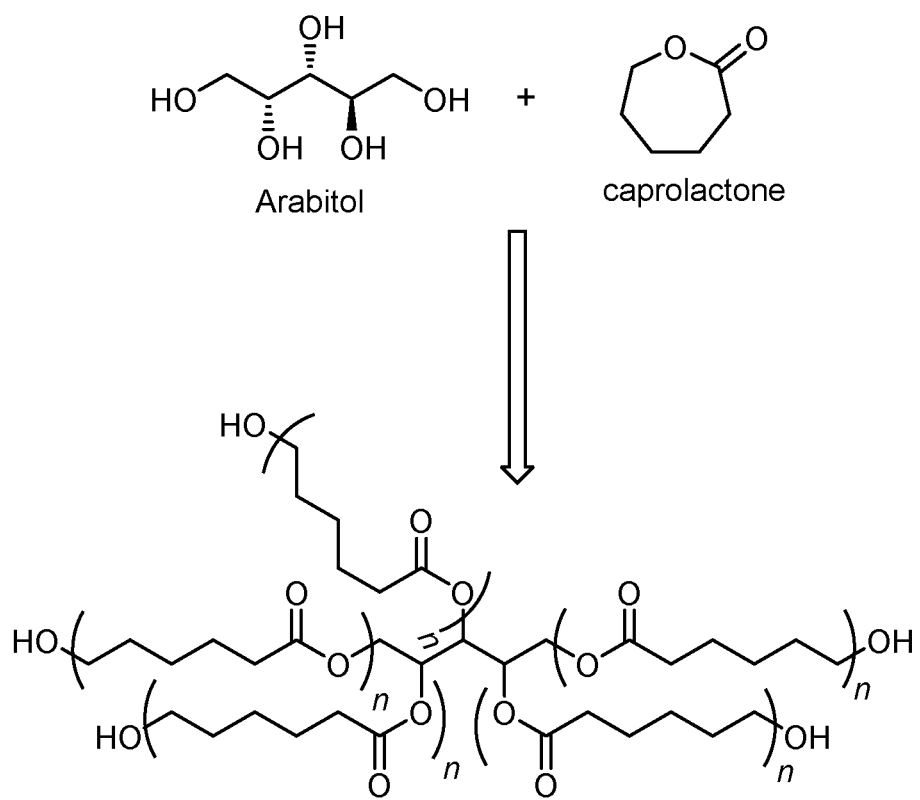
FIG. 12 shows general preparation of polycaprolactone pentaol oligomers for use in preparing adhesive devices of the present disclosure according to an embodiment.
Figure 13:
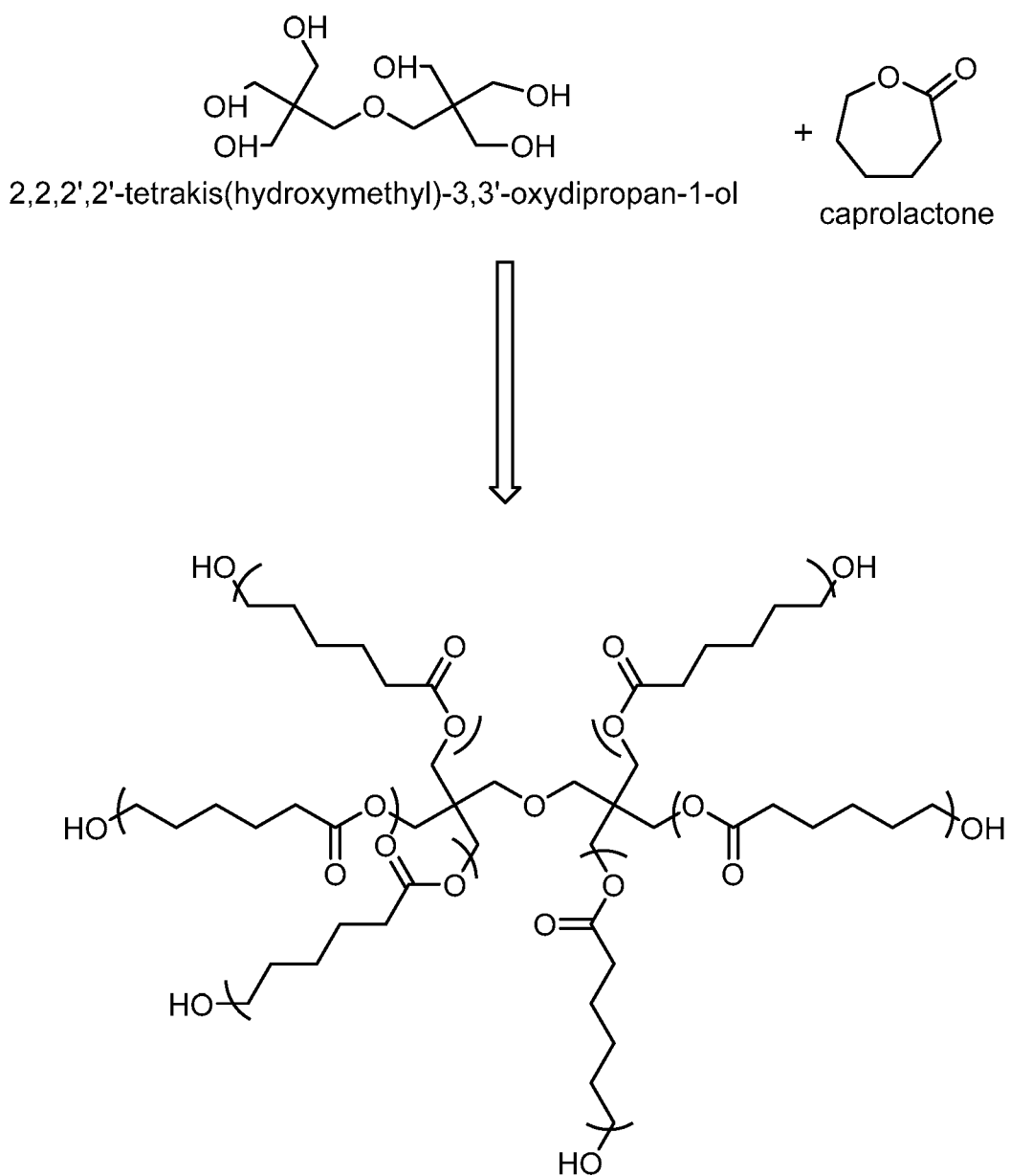
FIG. 13 shows general preparation of polycaprolactone hexaol oligomers for adhesives for use in preparing adhesive devices of the present disclosure according to an embodiment.
Figure 14:
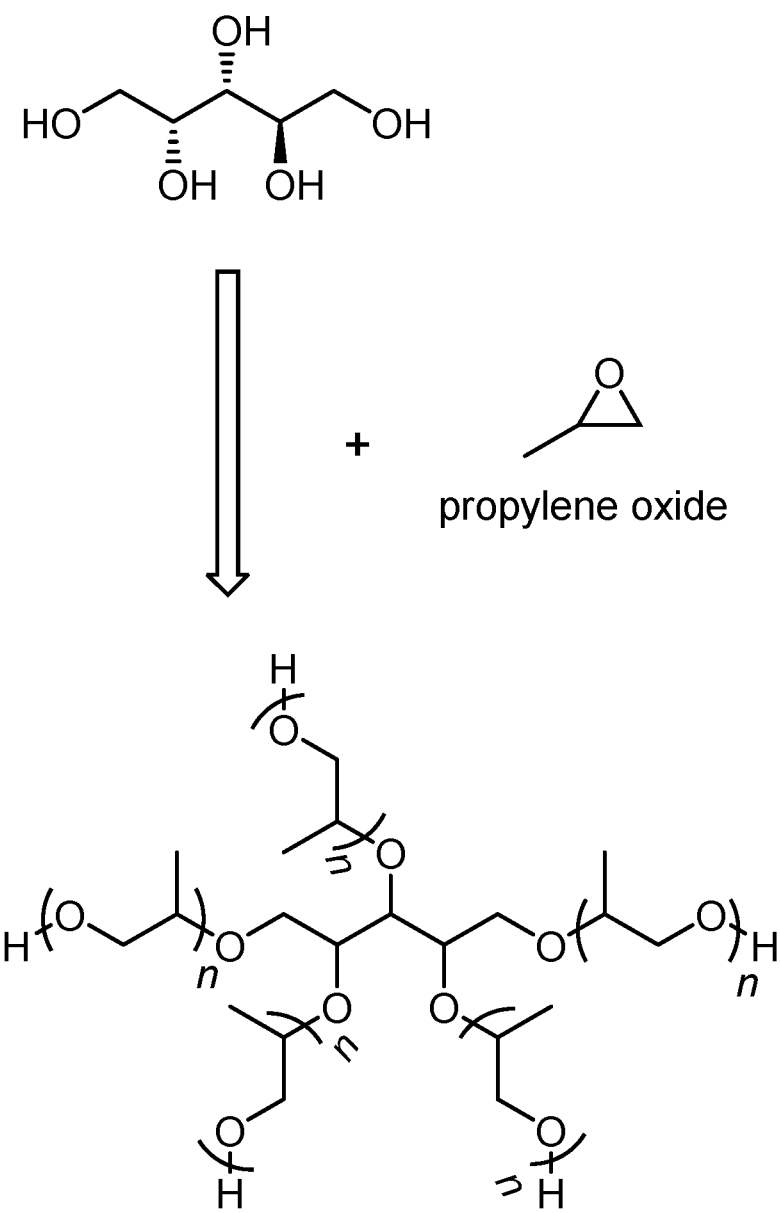
FIG. 14 shows the general preparation of a PPG pentaol oligomers for adhesives for use in preparing adhesive devices of the present disclosure according to an embodiment.

According to an embodiment, the oligomer may be selected from commercially available oligomers. FIG. 10 is an exemplary list of commercially available oligomers that may be used for the preparation of the compounds of the present disclosure. Alternatively, the oligomers may be prepared by a skilled person using common general knowledge in the field of polymer chemistry [32]. FIG. 11 shows non-limiting examples of sugar alcohols that may be used as a starting point for the preparation of the oligomer. FIG. 12 and FIG. 13 show examples of the general preparation of polycaprolactone pentaol and hexaol oligomers. FIG. 14 shows an example of the general preparation of PPG pentaol oligomers.

Figure 15:
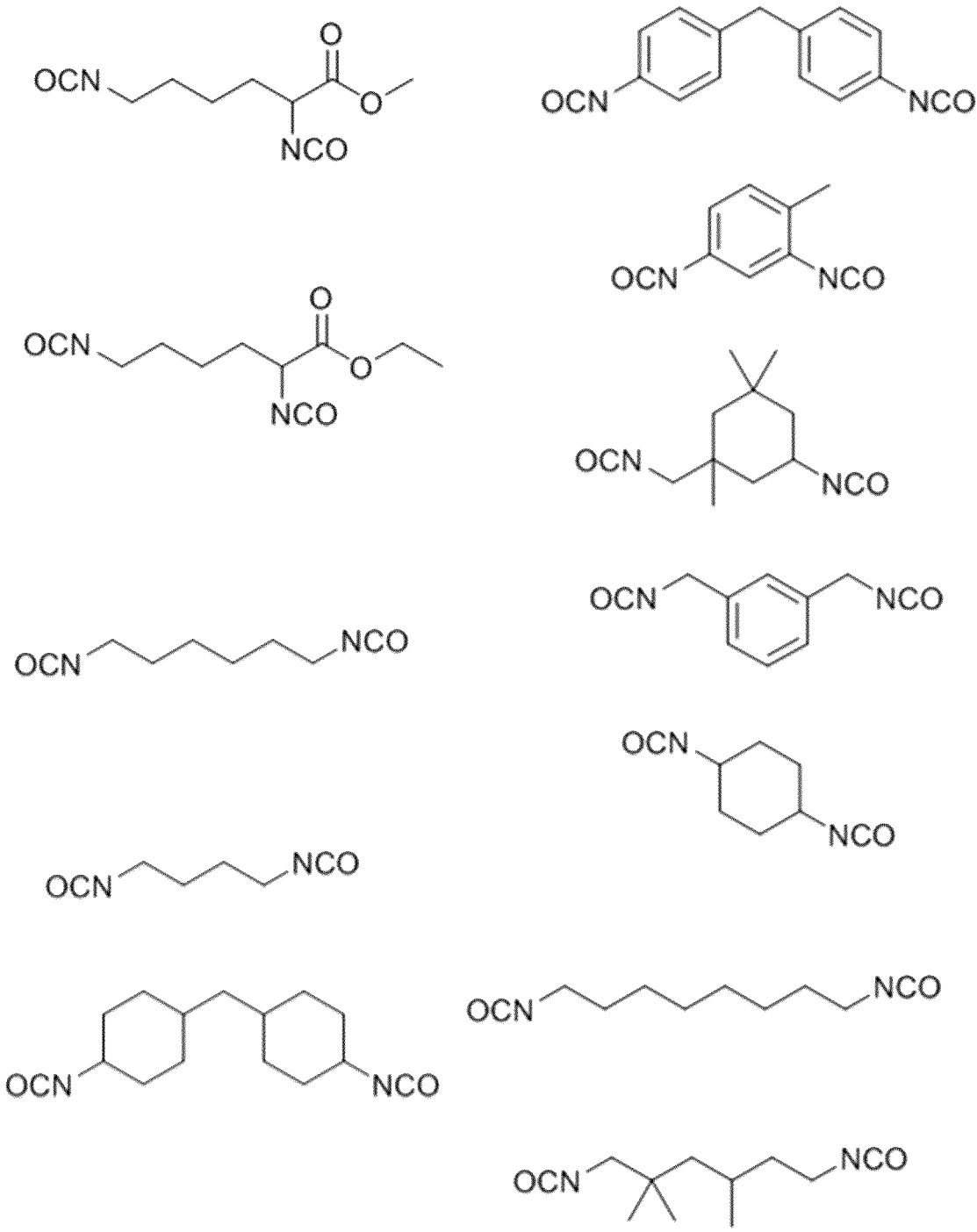
FIG. 15 shows an exemplary list of diisocyanate molecules that may be used for the preparation of the compounds suitable for use in devices of the present disclosure according to an embodiment.

According to an embodiment, the diisocyanate molecule may be selected from the group shown in FIG. 15.

According to an embodiment, the 4-alkylbenzene-1,2-diol derivative or a 5-alkylbenzene-1,2,3-triol derivative may be selected from the group shown in FIG. 16. This class of compounds have been known for their adhesion properties and are suitable for the synthesis of adhesive molecules. According to another embodiment, the preferred 4-alkylbenzene-1,2-diol derivative is dopamine and the preferred 5-alkylbenzene-1,2,3-triol derivative is 3,4,5-trihydroxyphenethylamine.

In some embodiments, the adhesive includes cross-linked structures. Biocompatible crosslinking agents are known to persons of skill in the art. Suitable crosslinking agents can include inorganic oxidants ($Na_3VO_4$ and tetrabutylammonium (meta)periodate (TBAP)), an organic or inorganic bases (($Na_2CO_3$), triethylamine) or organic complexing salts (Iron (III) citrate—FeCit), $FeCl_3$ and $FePO_4$).

In some embodiments, cross-linking agents are used in an amount of between 0.01 and 10 w/w % based on the weight of the adhesive, more preferably in an amount of between 0.1 and 5 w/w % based on the weight of the adhesive.

Adhesives may be applied to a support which is subsequently cut to size or a support may be cut to preferred shape and size and subsequently coated. Adhesive may be applied by methods known to those of skill in the art and can include e.g. spraying the adhesive onto the support or submerging the adhesive in the support (for applications where all surfaces of the support will be coated with adhesive). The amount of adhesive used with the support will vary depending on. the intended application of the device. Thickness ratios of between about 1:3 and 8:3 adhesive:backing layers have been found suitable, and a ratio of about 3:4 adhesive:backing thickness layer (e.g. 0.15 mm thick adhesive layer on a 0.2 mm thick backing layer) has been found particularly suitable.

The adhesive may be cross-linked to the support. In some embodiments, cross-linking reactions are delayed until time of use e.g. by storing the device under conditions that inhibit cross-linking reactions. Various approaches are available to ensure stability of the devices and can include cold storage and transportation, addition of antioxidants, encapsulation of the cross-linking agents in temperature triggered materials, careful selection of cross-linking agents that do not react at common storage conditions or addition of cross-linking agents that require external energy to initiate the cross-linking reactions.

The adhesive device may be provided "ready-to-use" with a removable backing covering the adhesive or as separate components that are assembled at the time of use by applying the adhesive to the support, including as a kit.

Suitable support materials include common biocompatible polymers including polyesters, polylactides, polypropylene, polyolefins, polyurethanes, polyamides, carbohydrate polymers and other natural or synthetic derived polymers.

The water insoluble adhesive devices described in the present disclosure may be used to adhere a first surface and a second by applying an adhesive device to at least a portion of at least one of the first and second surface; and bringing at least a portion of the first and second surfaces into contact with each other and/or bringing at least a portion of the first and second surfaces into contact with the adhesive device.

The first surface may comprise soft tissue and the second surface may comprise hard tissue such as bone. Alternatively, both surfaces may be soft tissue, or hard tissue such as bone. Alternatively, the first surface may comprise soft tissue and the second surface may be a surface of an implant or device. Alternatively, the first surface may comprise hard tissue such as bone and the second surface may be a surface of an implant or device.

According to an embodiment, the device can be applied to the above surfaces using a source of external energy to enhance the curing of the adhesive with said surface.

According to an embodiment, the devices described in the present disclosure may provide effective adhesion to one or more surfaces that are wet prior to application of the adhesive or if the device must be applied in a wet environment.

Alternatively, the device of the present disclosure may provide effective adhesion to one or more surfaces that are adhered together with the adhesive device and wet following application of the adhesive device. The device of the present disclosure may continue to provide effective adhesion to one or more surfaces that are adhered together and submerged in aqueous media following application of the adhesive device.

In particular, the adhesive device of the present disclosure may provide effective adhesion to one or more surfaces that are adhered together in the presence of blood or may continue to provide effective adhesion to one or more surfaces that are exposed to blood following bonding.

Non-limiting examples of soft-to-hard tissue binding include the attachment of tendons, muscles, cartilage or skin to bone.

Non-limiting examples of soft-soft tissue binding where the device is advantageous include wound closure to curtail bleeding, closure of surgical incisions, skin grafts, cartilage attachment to skin, lung punctures, and cardiac tamponade.

Non-limiting examples of hard-to-hard tissue binding where the device is advantageous include bone fractures and bone grafts.

Non-limiting examples of implantable devices that could benefit from attachment in situ using the device include lead for real-time glucose monitoring meter, lead for a pacemaker, and insulin delivery system.

Another example that could benefit from in situ attachment is use of the device comprising a flexible or ridged polymer support with one side coated with adhesive for application in stabilization of bone fractures [33-34]. This could include an initially flexible structure that is rigidified and has a bioadhesive/cement located on one surface of the structure for sticking to bone.

The present disclosure provides a device comprising a water insoluble adhesive having at least one compound of structure 1. The device comprises the water insoluble adhesive and a support, in one embodiment, a biocompatible support. The support may, for example, be a sheet structure and the water insoluble adhesive may be coated onto or impregnated into the sheet or portions thereof (e.g. there may be discrete bonding sites). In one embodiment, the sheet is a flexible rigidifiable biocompatible sheet i.e. a 30 flexible sheet whose stiffness can be increased. In one embodiment, the water insoluble adhesive is located on a first surface of the sheet. In one embodiment, the sheet has first and second opposed surfaces and both surfaces are coated with the adhesive. In one embodiment, the biocompatible sheet is a sheet as described in US2015/0202046. In one embodiment, the main constituent on the biocompatible sheet structure is a biodegradable and/or bioresorbable polymer. In some embodiments, the polymer material contains repeating groups which include any one or a combination of amides, peptides, urethanes, esters, carbonates, anhydrides, ethers, and sulphonamides. In one embodiment, the device further comprises a porous ceramic. In one embodiment, the device is a bone tape comprising a flexible rigidifiable biocompatible sheet as described in US2015/0202046 and a water insoluble bioadhesive as described herein. The dimensions of the sheet (length, width, thickness) may be varied depending on the application and the bone tape may be cut prior to use. The device may further comprise a removable protective sheet to protect the water insoluble adhesive prior to use.

Preferred protective sheet materials include polyesters (preferably polycaprolactone), polylactides (PLA, PLGA, Polydioxanone, etc.), polycarbonates (specifically poly(trimethylene carbonate)) and other biocompatible polymers. The support material must have compatibility with the adhesive such that adhesion between the adhesive and support are sufficient to provide application specific performance over a relevant timeline (e.g. ~ 6 weeks of strong bonding for bone healing). Incompatible support materials may be chemically or physically modified to improve adhesion by treatment with oxygen plasma, acid etchants, basic agents, binding agents or other suitable surface modifiers.

In one embodiment, the support is formed from polycaprolactone. which due to its mechanical properties and high similarities to the adhesive structure can result in good performance at physiological temperatures and strong bonding to the adhesive without pretreatment or modifications of the polycaprolactone surface. In one embodiment, polycaprolactone is used without pretreatment or modifications of the polycaporlactone surface.

The device may be an implant comprising a biocompatible support and a water insoluble adhesive as described herein coated onto or impregnated into the support.

The water insoluble adhesive and support components of the device may be hydrolysable or enzyme degradable under physiological conditions. Furthermore, the entire device may be hydrolysable or enzyme degradable under physiological conditions.

According to an embodiment, the device of the present disclosure may be used to perform a number of functions, including but not limited to:

Align, orient, or fasten tissues together so they can heal

Align, orient, or fasten tissues together so that they are more aesthetically desirable Close a wound or void so fluid loss, pressure loss, air loss, etc. is slowed or minimized Seal a wound, defect or void by fixing another impermeable material over the wound, defect or void Affix a prosthetic or biomaterial Localize a drug, drug delivery agent, sensor or other device in a certain area.

In one embodiment, the device is the water insoluble adhesive coated onto a support which may be comprised of a patch or tape for use in medical procedures, such as craniomaxillofacial surgery.

According to an embodiment, the device may be used for the fixation of medical devices to a target site or tissue. Examples may include fixation of a therapeutic patch, a surgical mesh for hernia, bone fractures, or other applications, an insulin delivery or monitoring device, a wound dressing or bandage, a sensor, a catheter, or a regenerative material such as a bio-scaffold.

According to an embodiment, the device may be comprised of the support, such as a biomedical mesh with the water insoluble adhesive providing adherence to tissues. Examples may include a biomedical mesh that does not need to be sutured, screwed, stapled, or otherwise fastened to tissues or biological structures. Additional examples may include a biological mesh support that provides improved fixation when compared to mechanical fixation alone. In a select embodiment, this could be used to adhere fragments of bone to a mesh, resulting in improved bone stabilization. In another embodiment, the adherent mesh may provide more uniform adhesion, improving healing. In another embodiment, the adherent mesh may integrate with cells better, improving integration with tissues. In another embodiment, the adherent mesh may be loaded with a drug, protein, biomaterial or other therapeutic agent to enhance or improve healing.

According to an embodiment, the water insoluble adhesive may be used to functionalize a surface of the support. This may be used to improve cellular adhesion to the surface, control, select or recruit adhesion of preferential types of cells, or attach a therapeutic agent or compound to the surface. In a select embodiment, this could be used to adhere antibiotic or antifungal elements, rendering the surface less susceptible to bacterial contaminations. In one embodiment, the described bioadhesive may be used to functionalize a non-adherent surface e.g. so that cells or proteins are able to attach to the surface, enabling or improving surface functionalization and degree of integration e.g. one surface of the support can be an adherent surface and the opposite surface can be a functionalized surface.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

The above description and accompanying drawings should be taken as illustrative of the invention and it is to be understood that it is intended to cover any variations, uses, or adaptations of the invention following, in general, the principles of the invention and including such departures from the present disclosure as come within known or customary practice within the art to which the invention pertains. The embodiments of the invention described above are intended to be exemplary only. The scope of the invention is therefore intended to be limited solely by the scope of the appended claims.

EXAMPLES

With the exception of Adhesive 6 (Example 6), which is prepared as a comparative control catechol-blocked non-adhesive system, all of the adhesives presented in the following examples present utility in adhesive devices for different applications, with some adhesive examples presenting properties which make them better suited for devices directed at certain applications compared to other adhesive examples. Particularly significant, the adhesive formulations as described herein may be used without solvent. This can be a significant advantage because, among other things, as demonstrated in Example 14, residual solvent can decrease the cohesive strength of adhesives.

Examples 1-8 present the syntheses of water insoluble adhesives to be used in the adhesive device of the present disclosure; example 9 demonstrates the biocompatibility of the select adhesives for use in the adhesive device of the present disclosure, examples 10-12 present the adhesive properties of the adhesives for use in the adhesive device of the present disclosure, example 13 presents a working example of the device of the present disclosure, and example 14 presents the effect of residual solvent on the performance of adhesives disclosed herein.

Example 1: Difunctional PCL Adhesive (Adhesives 1a-b)

Figure 17:
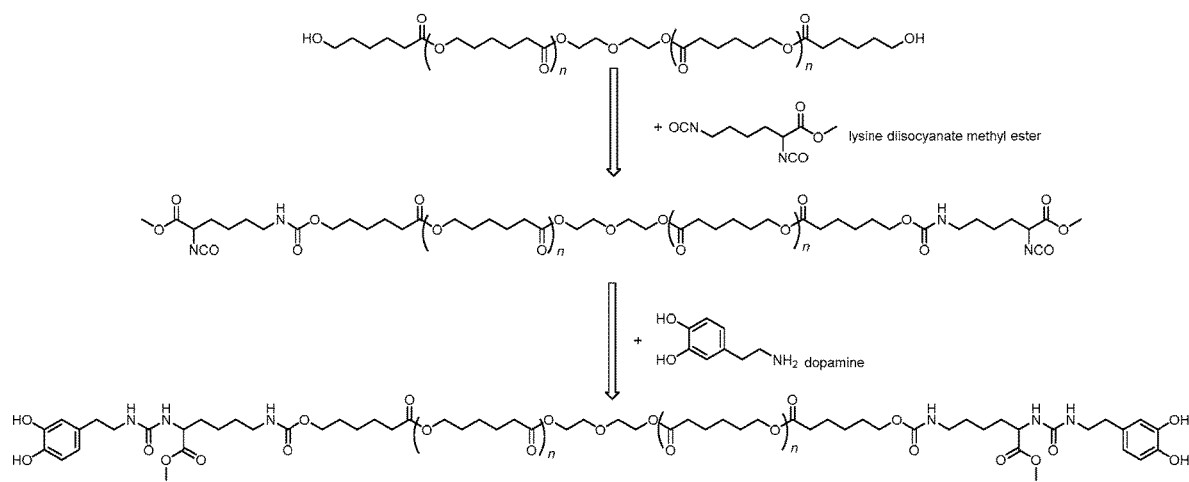
FIG. 17 shows a generalized reaction scheme for the synthesis of difunctional PCL adhesives according to an embodiment.

FIG. 17 shows a generalized reaction scheme for the synthesis of difunctional PCL adhesives in which the terminal hydroxyl groups of a PCL-diol reacts with one of two isocyanate groups of the diisocyanate molecule resulting in a-PCL-diisocyanate molecule. The free isocyanates then react with a reactive moiety (here an amine) present on the alkyl chain of the 4-alkylbenzene-1,2-diol derivative (here dopamine).

Figure 18:
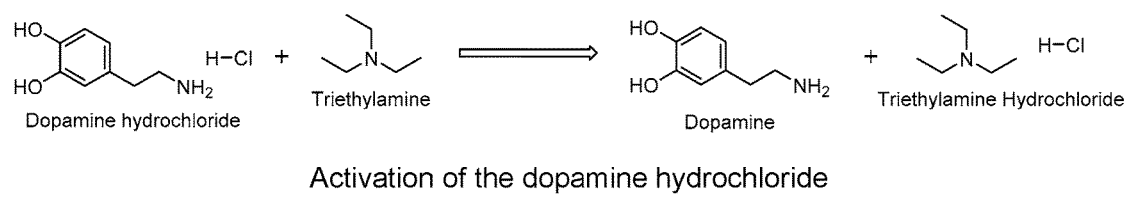
FIG. 18 shows a method for the activation of dopamine hydrochloride into free dopamine according to an embodiment.

Example 1a: Synthesis of Adhesive 1a as an Example of a Difunctional PCL Adhesive a) Activation of the Dopamine Derivative (Dopa):
FIG. 18 shows the activation of dopamine hydrochloride. One molar equivalent of dopamine hydrochloride was dissolved in a minimum volume of anhydrous DMAc at room temperature. An equivalent molar amount of triethylamine was added to complex the hydrochloride salt from dopamine. This mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated Polycaprolactone (PCL) Oligomers (Prepolymer 1a):
15 mmol of polycaprolactone diol with an average molecular weight of 530 g/mol ($\bar{n}$=2) was added to a dry 250 mL 3-neck flask and degassed under vacuum at 60° C. for 12 h. The flask was purged with argon and 75 mL anhydrous DMAc was added through a septum with stirring under argon protection. Once the reaction mixture was completely clear, it was cooled to room temperature. 31.5 mmol of LDI (Methyl Ester L-Lysine Diisocyanate; 5% molar excess to the PCL hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give the prepolymer 1a.

c) Synthesis of PCL Based Oligomeric Dopamine Adhesive (Adhesive 1a):
Prepolymer 1a was functionalized by adding 33 mmol of activated dopamine in 60 mL of DMAc to the reaction mixture. An ice bath was used to dissipate heat from this rapid and exothermic step. The reaction was stirred for an additional 2 hours to ensure complete reaction, then the mixture was slowly poured into 500 mL ethyl acetate at room temperature. The mixture was slowly stirred for 30 minutes, then 250 mL deionized $H_2O$ slightly acidified with a few drops of HCl was added. This two-phase system was transferred to a 1 L separatory funnel and washed 5 times with slightly acidic deionized water, retaining the organic phase between washings, to remove DMAc and undesirable reaction products. The solvent was removed under vacuum and the product was dissolved in a minimum volume of 1:1 acetone/ethanol. Approximately 5× the volume of hexanes was slowly added with stirring and the mixture was left in a fridge overnight. The cold solvent fraction was then decanted off, leaving the product stuck to the walls of the beaker.

Example 1b: Synthesis of Adhesive 1b as an Example of a Difunctional PCL Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCL Oligomers (Prepolymer 1b):

10 mmol of polycaprolactone diol with an average molecular weight of 2000 g/mol ($\bar{n}$=28.5) was added to a dry 250 mL 3-neck flask and degassed under vacuum at 60° C. for 12 h. The flask was purged with argon and 50 mL anhydrous DMAc was added through a septum with stirring under argon protection. Once the reaction mixture was completely clear, it was cooled to room temperature. 21 mmol of LDI (Methyl Ester L-Lysine Diisocyanate, 5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 1b.

c) Synthesis of PCL Based Oligomeric Dopamine Adhesive (Adhesive 1b):

Prepolymer 1b was functionalized by adding 22 mmol of activated dopamine in 40 mL of DMAc to the reaction mixture. An ice bath was used to dissipate heat from this rapid and exothermic step. The reaction was stirred for an additional 2 hours to ensure complete reaction, then the mixture was slowly poured into 500 mL ethyl acetate at room temperature. The mixture was slowly stirred for 30 minutes, then 250 mL deionized $H_2O$ slightly acidified with a few drops of HCl was added. This 2-phase system was transferred to a 1 L separatory funnel and washed 5 times with slightly acidic deionized water, retaining the organic phase between washings, to remove DMAc and undesirable reaction products. The solvent was removed under vacuum and the product was dissolved in a minimum volume of 1:1 acetone/ethanol. Approximately 5× the volume of hexanes was slowly added with stirring and the mixture was left in a fridge overnight. The cold solvent fraction was then decanted off, leaving the product stuck to the walls of the beaker.

Example 2: Trifunctional PCL Adhesive (Adhesives 2a-c)

Figure 19:
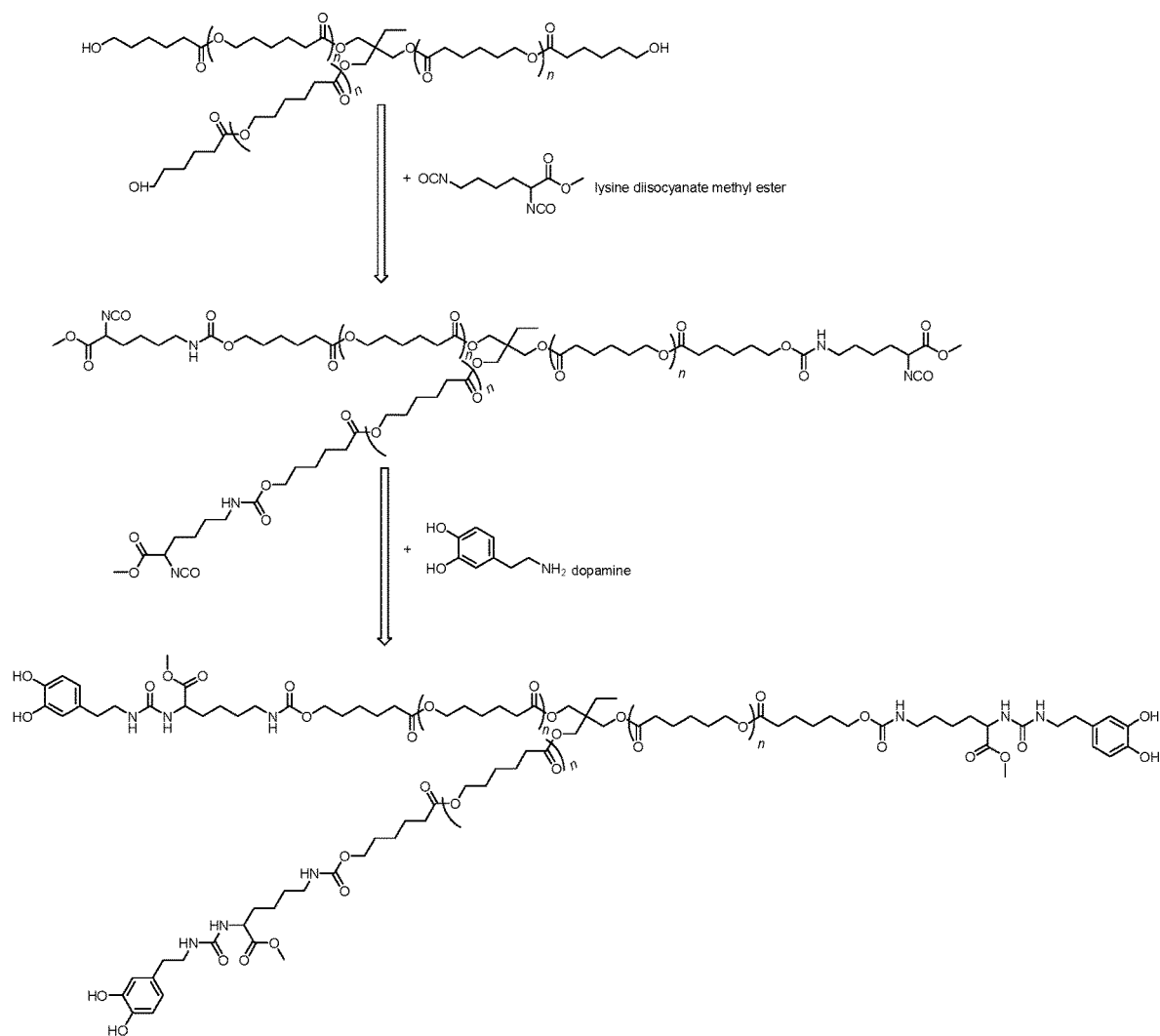
FIG. 19 shows a generalized reaction scheme for the synthesis of water insoluble trifunctional PCL adhesives according to an embodiment.

FIG. 19 shows a generalized reaction scheme for the synthesis of trifunctional PCL adhesives in which the terminal hydroxyl groups of a PCL-triol reacts with one of two isocyanate groups of the diisocyanate molecule resulting in a PCL-triisocyanate molecule. The free isocyanates then react with a reactive moiety (here an amine) present on the alkyl chain of the 4-alkylbenzene-1,2-diol derivative (here dopamine)

Example 2a: Synthesis of Adhesive 2a as an Example of a Trifunctional PCL Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCL Oligomers (Prepolymer 2a):

Ten mmol of polycaprolactone triol with an average molecular weight of 300 g/mol ($\bar{n}$=0.7) was added to a dry 250 mL 3-neck flask and degassed under vacuum at 60° C. for 12 h. The flask was purged with argon and 25 mL anhydrous DMAc was added through a septum with stirring under argon protection. Once the reaction mixture was completely clear, it was cooled to room temperature. 31.5 mmol of LDI (Methyl Ester L-Lysine Diisocyanate, 5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 2a.

c) Synthesis of PCL Based Oligomeric Dopamine Adhesive (Adhesive 2a)

Prepolymer 2a was functionalized by adding 33 mmol of activated dopamine in 50 mL of DMAc to the reaction mixture. An ice bath was used to dissipate heat from this rapid and exothermic step. The reaction was stirred for an additional 2 hours to ensure complete reaction, then the mixture was slowly poured into stirred deionized ice water (200 mL) at 0° C. Stirring was ceased, and Adhesive 2a was recovered as a thick viscous fluid on the bottom of the flask after decanting the water fraction. It was re-dissolved in acetone (75 mL) and precipitated out of solution with deionized water (200 mL) twice more to remove any residual triethylamine, dopamine, LDI derivatives and other reaction by-products.

Example 2b: Synthesis of Adhesive 2b as an Example of Trifunctional PCL Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCL Oligomers (Prepolymer 2b):

10 mmol of polycaprolactone triol with an average molecular weight of 900 g/mol ($\bar{n}$=2.3) was added to a dry 250 mL 3-neck flask and degassed under vacuum at 60° C. for 12 h. The flask was purged with argon and 25 mL anhydrous DMAc was added through a septum with stirring under argon protection. Once the reaction mixture was completely clear, it was cooled to room temperature. 31.5 mmol of LDI (Methyl Ester L-Lysine Diisocyanate, 5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 2b.

c) Synthesis of PCL Based Oligomeric Dopamine Adhesive (Adhesive 2b)

Prepolymer 2b was functionalized by adding 33 mmol of activated dopamine in 50 mL of DMAc to the reaction mixture. An ice bath was used to dissipate heat from this rapid and exothermic step. The reaction was stirred for an additional 2 hours to ensure complete reaction, then the mixture was slowly poured into stirred deionized water (200 mL) at room temperature. Stirring was ceased, and Adhesive 2b was recovered as a thick viscous fluid on the bottom of the flask after decanting the water fraction. It was re-dissolved in acetone (75 mL) and precipitated out of solution with deionized water (200 mL) twice more to remove any residual triethylamine, dopamine, LDI derivatives and other reaction by-products.

Example 2c: Synthesis of Adhesive 2c as an Example of Trifunctional PCL Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCL Oligomers (Prepolymer 2c):

10 mmol of polycaprolactone triol with an average molecular weight of 2000 g/mol ($\bar{n}$=5.5) was added to a dry 250 mL 3-neck flask and degassed under vacuum at 60° C. for 12 h. The flask was purged with argon and 50 mL anhydrous DMAc was added through a septum with stirring under argon protection. Once the reaction mixture was completely clear, it was cooled to room temperature. 31.5 mmol of LDI (Methyl Ester L-Lysine Diisocyanate, 5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 2c.

c) Synthesis of PCL Based Oligomeric Dopamine Adhesive (Adhesive 2c)

Prepolymer 2c was functionalized by adding 33 mmol of activated dopamine in 50 mL of DMAc to the reaction mixture. An ice bath was used to dissipate heat from this rapid and exothermic step. The reaction was stirred for an additional 2 hours to ensure complete reaction, then the mixture was slowly poured into stirred deionized water (200 mL) at room temperature. Stirring was ceased, and Adhesive 2c was recovered as a thick viscous fluid on the bottom of the flask after decanting the water fraction. It was re-dissolved in a 1:1 ethanol/acetone mixture (150 mL) and precipitated out of solution with slightly acidified deionized water (500 mL) twice more to remove any residual reaction by-products Example 3: Tetrafunctional PCL Adhesive (Adhesive 3)

Figure 20:
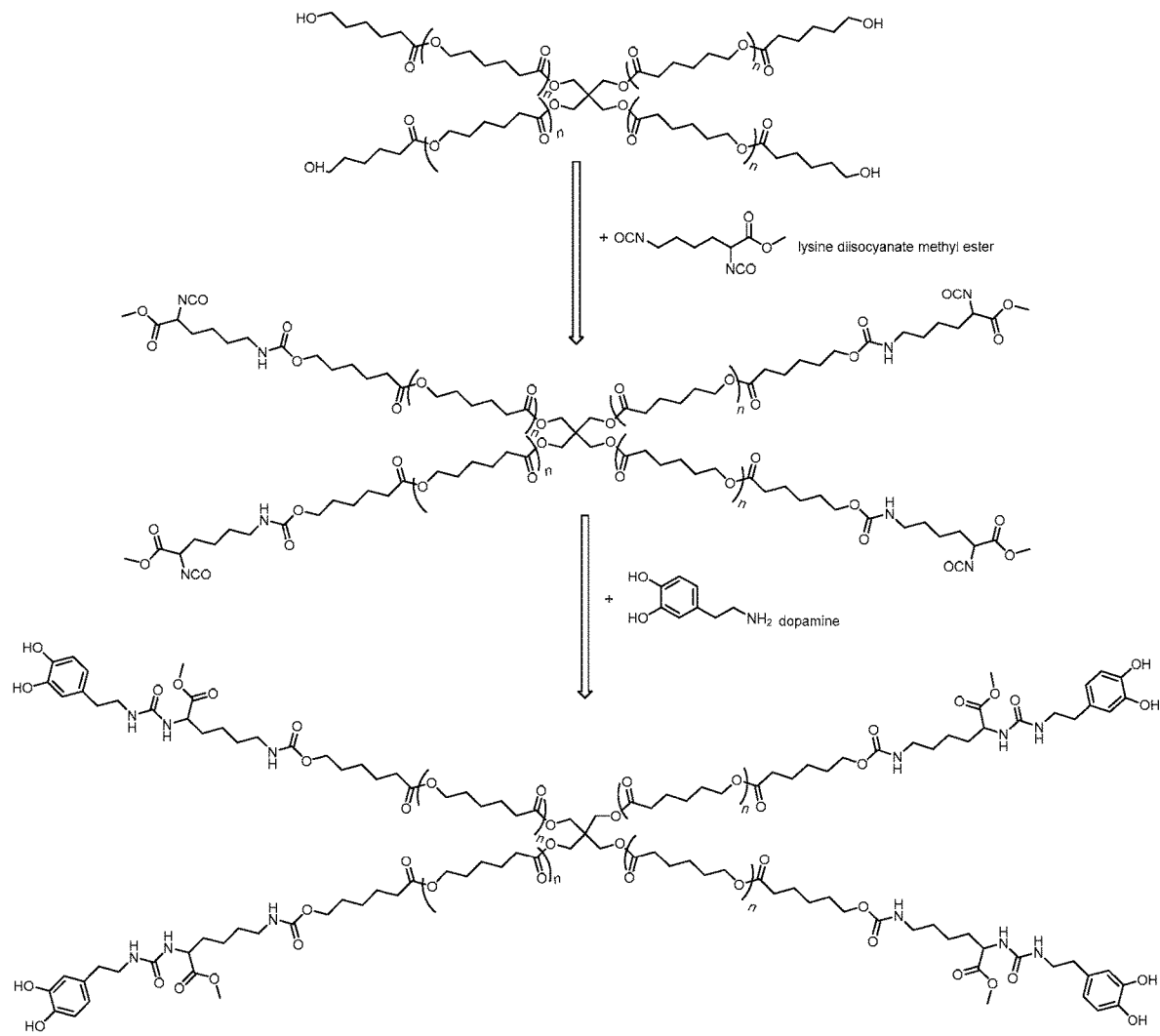
FIG. 20 shows a generalized reaction scheme for the synthesis of water insoluble tetrafunctional PCL adhesives according to an embodiment.

FIG. 20 shows a generalized reaction scheme for the synthesis of tetrafunctional PCL adhesives in which the terminal hydroxyl groups of a PCL-tetraol reacts with one of two isocyanate groups of the diisocyanate molecule resulting in a PCL-Tetraisocyanate molecule. The free isocyanates then react with a reactive moiety (here an amine) present on the alkyl chain of the 4-alkylbenzene-1,2-diol derivative (here dopamine).

Example 3a: Synthesis of Adhesive 3a as an Example of Tetrafunctional PCL Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCL Oligomers (Prepolymer 3a):

10 mmol of polycaprolactone tetrol with an average molecular weight of 1000 g/mol ($\bar{n}$=2) was added to a dry 250 ml 3-neck flask and degassed under vacuum at 60° C. for 12 h. The flask was purged with argon and 50 mL anhydrous DMAc was added through a septum with stirring under argon protection. Once the reaction mixture was completely clear, it was cooled to room temperature. 42 mmol of LDI (5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give Prepolymer 3a.

c) Synthesis of PCL Based Oligomeric Dopamine Adhesive (Adhesive 3a)

Prepolymer 3a was functionalized by adding 44 mmol of activated dopamine in 50 mL of DMAc to the reaction mixture. An ice bath was used to dissipate heat from this rapid and exothermic step. The reaction was stirred for an additional 2 hours to ensure complete reaction, then the mixture was slowly poured into a mixture of diethyl ether (700 mL) and deionized water (300 mL) at room temperature. The mixture was stirred vigorously for 2 hours, then stirring was ceased and the reaction mixture was cooled in the fridge. The liquid phase was decanted off, and Adhesive 3a was recovered from the walls of the beaker. It was re-dissolved in a mixture of acetone/ethyl acetate (200 mL) and precipitated out of solution with hexanes (500 mL) to remove any residual reaction by-products.

Example 4: Pentafunctional PCL Adhesive (Adhesive 4)

Figure 21:
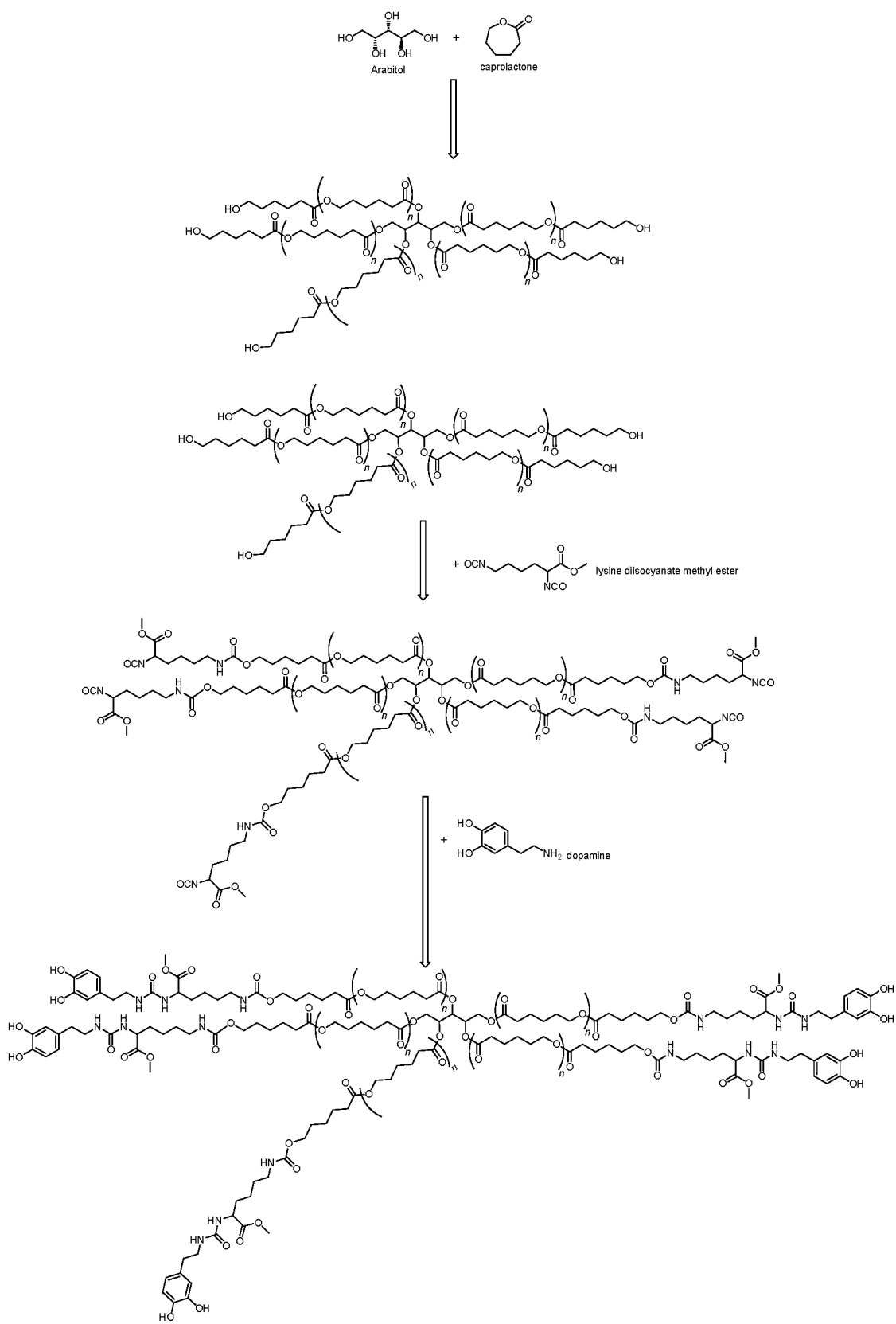
FIG. 21 shows a generalized reaction scheme for the synthesis of water insoluble penta-functional PCL adhesives via arabitol according to an embodiment.

FIG. 21 shows a generalized reaction scheme for the synthesis of pentafunctional PCL adhesive in which the terminal hydroxyl groups of a PCL-Pentaiol reacts with one of two isocyanate groups of the diisocyanate molecule resulting in a PCL-Pentaisocyanate molecule. The free isocyanates then react with a reactive moiety (here an amine) present on the alkyl chain of the 4-alkylbenzene-1,2-diol derivative (here dopamine) to give Adhesive 4.

Example 5: Hexafunctional PCL Adhesive (Adhesive 5)

Figure 22:
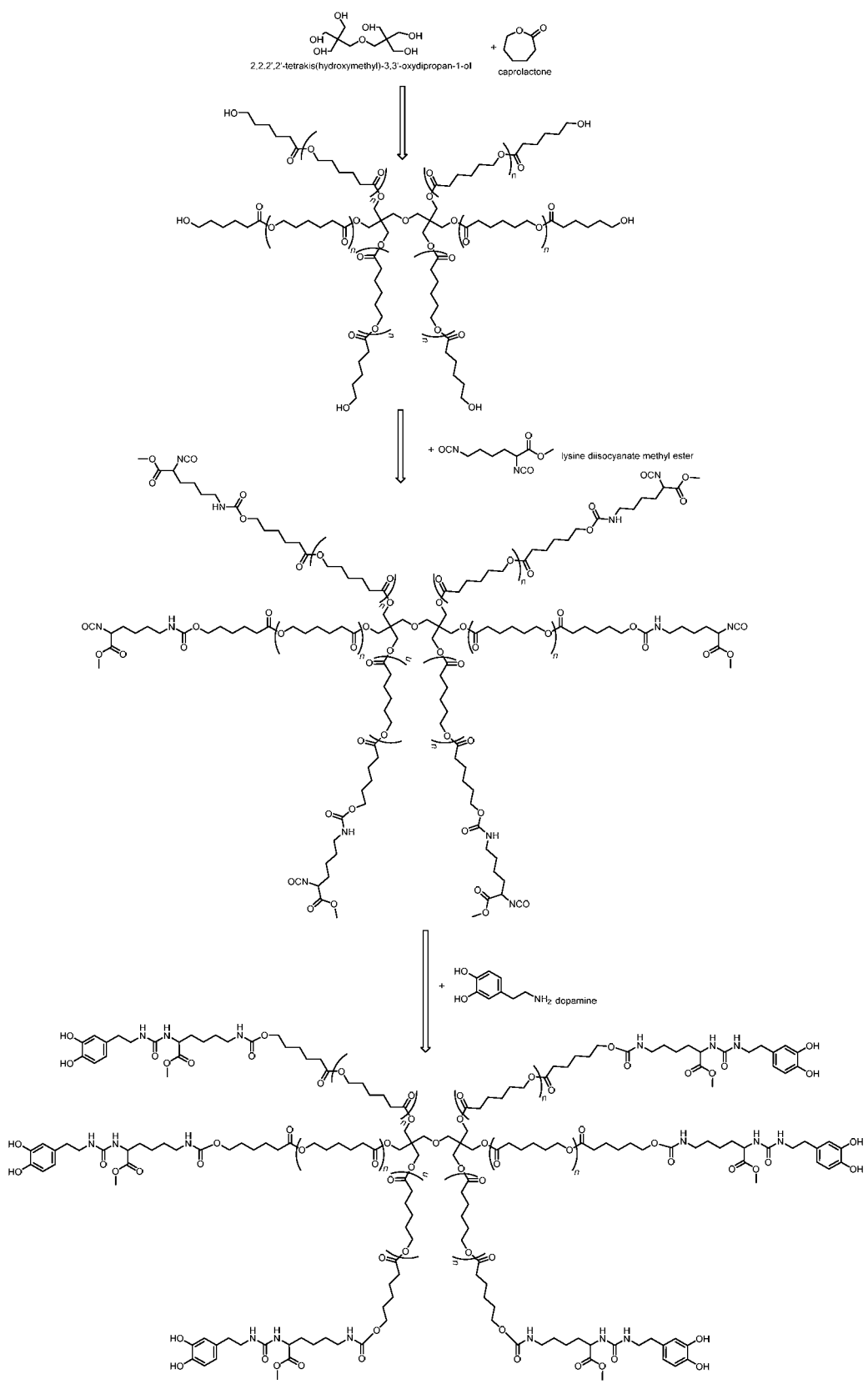
FIG. 22 shows a generalized reaction scheme for the synthesis of water insoluble hexafunctional PCL adhesives via tetrakis(hydroxymethyl)oxydipropanol according to an embodiment.

FIG. 22 shows a generalized reaction scheme for the synthesis of hexafunctional PCL adhesive in which the terminal hydroxyl groups of a PCL-Hexol reacts with one of two isocyanate groups of the diisocyanate molecule resulting in a PCL-Triisocyanate molecule. The free isocyanates then react with a reactive moiety (here an amine) present on the alkyl chain of the 4-alkylbenzene-1,2-diol derivative (here dopamine) to give Adhesive 5.

Example 6: Trifunctional PCL Control (Adhesive 6)

For comparative purposes, Adhesive 6 was prepared as a negative control from a dopamine derivative in which the catechol groups were blocked by methoxy functional groups.

a) Synthesis of Isocyanate Terminated PCL Oligomers (Prepolymer 6)

10 mmol of polycaprolactone triol with an average molecular weight of 900 g/mol ($\bar{n}$=2.3) was added to a dry 250 mL 3-neck flask and degassed under vacuum at 60° C. for 12 h. The flask was purged with argon and 25 mL anhydrous DMAc was added through a septum with stirring under argon protection. Once the reaction mixture was completely clear, it was cooled to room temperature. 31.5 mmol of LDI (Methyl Ester L-Lysine Diisocyanate, 5% molar excess to hydroxyl groups) was added to the reaction mixture with a syringe through a silicone rubber septum and the mixture was stirred for 1 hour at room temperature. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 6.

b) Synthesis of PCL Based Oligomeric Dopamine Control (Adhesive 6)

Prepolymer 6 was functionalized with methoxy capped dopamine by adding 33 mmol of 3,4-Dimethoxyphenethylamine in 50 mL of DMAc to the reaction mixture. An ice bath was used to dissipate heat from this rapid and exothermic step. The reaction was stirred for an additional 2 hours to ensure complete reaction, then the mixture was slowly poured into stirred deionized water (200 mL) at room temperature. Stirring was ceased, and Adhesive 6 was recovered as a thick viscous fluid on the bottom of the flask after decanting the water fraction. It was re-dissolved in acetone (100 mL) and precipitated out of solution with deionized water (200 mL) twice more to remove any residual reaction by-products.

Example 7: Difunctional Poly(dimethylsiloxane) (PDMS) Adhesive (Adhesive 7)

Figure 23:
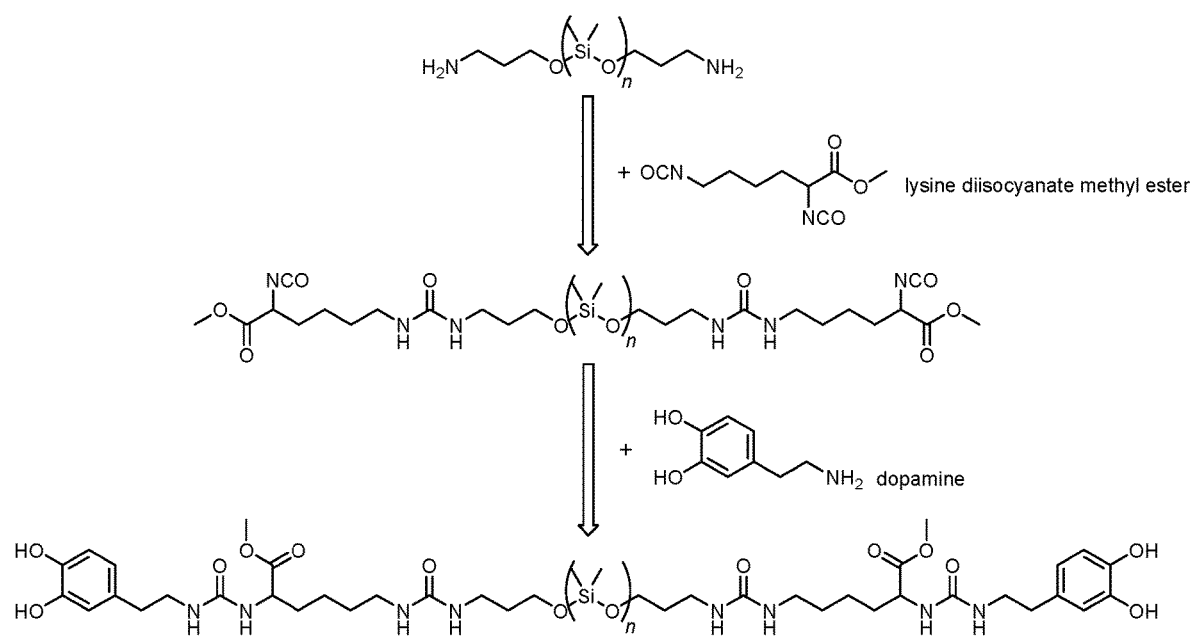
FIG. 23 shows a generalized reaction scheme for the synthesis of water insoluble difunctional PDMS adhesive according to an embodiment.
Figure 24:
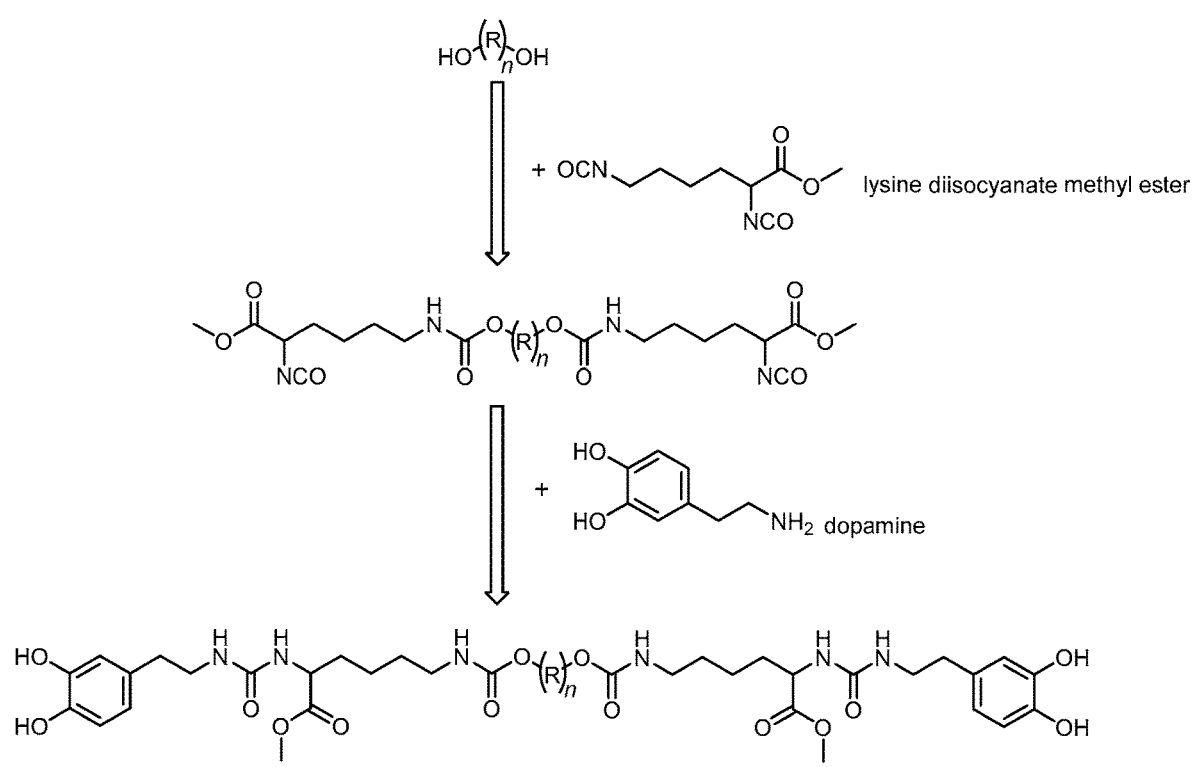
FIG. 24 shows a generalized reaction scheme for the synthesis of a water insoluble difunctional adhesive according to an embodiment.

FIG. 23 shows a generalized reaction scheme for the synthesis of for the synthesis of difunctional PDMS adhesive in which the terminal hydroxyl groups of a PDMS-Diamine reacts with one of two isocyanate groups of the diisocyanate molecule resulting in a PDMS-Diisocyanate molecule. The free isocyanates then react with a reactive moiety (here an amine) present on the alkyl chain of the 4-alkylbenzene-1,2-diol derivative (here dopamine).

Example 7a: Synthesis of Adhesive 7a as an Example of Difunctional PDMS Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PDMS Oligomers (Prepolymer 7a):

10.5 g of diamine terminated PDMS with an average molecular weight of 2500 g/mol ($\bar{n}$=32) was added to a dry 250 mL 3-neck flask and degassed under vacuum at 60° C. for 12 h. The flask was purged with argon and 100 ml anhydrous DMAc was added through a septum with stirring under argon protection. Once the reaction mixture was completely clear, it was cooled in an ice bath. 1.87 g of LDI (5% molar excess to amine groups) was added to the reaction mixture with a syringe through a silicone rubber septum. The reaction mixture was stirred in the ice bath for 2 hours, and then an additional 2 hours at room temperature to give prepolymer 7a.

c) Synthesis of PDMS Based Oligomeric Dopamine Adhesive (Adhesive 7a)

Prepolymer 7a was functionalized by adding 1.76 g activated dopamine in 40 mL of DMAc to the reaction mixture. An ice bath was used to dissipate heat from this rapid and exothermic step. The reaction was stirred for an additional 2 hours to ensure complete reaction, then the mixture was slowly poured into methanol (300 mL) at room temperature. The mixture was stirred vigorously for 1 hour, then stirring was ceased and the reaction mixture was cooled in the fridge. The liquid phase was decanted off, and the Adhesive 7a was recovered from the walls of the beaker. It was re-dissolved in acetone (200 mL) and precipitated by pouring into methanol a second time (500 mL) to remove any residual reaction by-products.

Example 8: Difunctional Poly(Hexamethylene Carbonate) (PCN) Adhesive (Adhesive 8)

Figure 25:
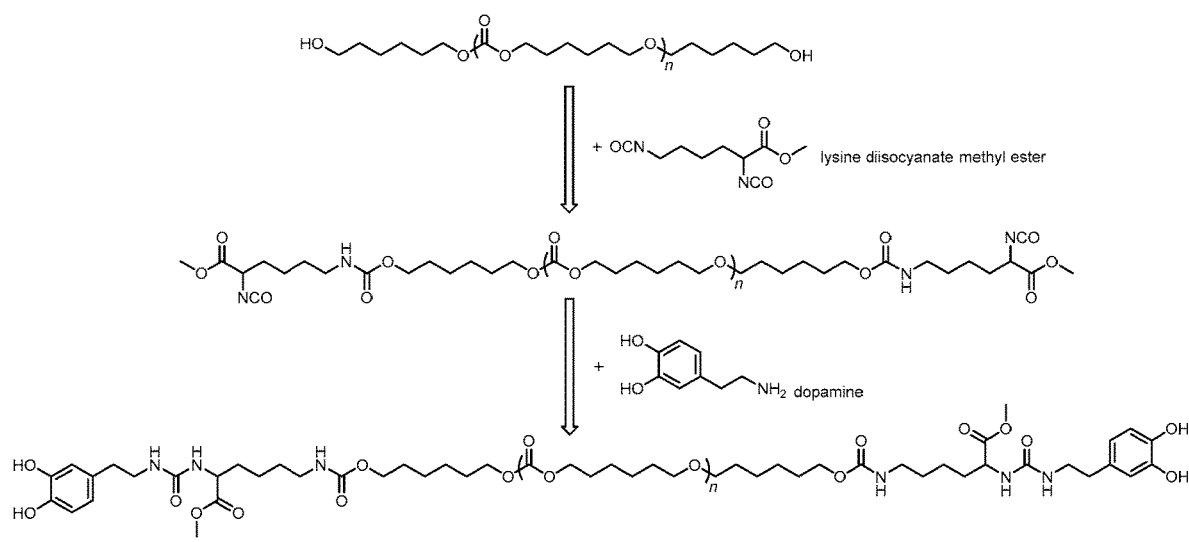
FIG. 25 shows a generalized reaction scheme for the synthesis of water insoluble difunctional PCN adhesive according to an embodiment.

FIG. 25 shows a generalized reaction scheme for the synthesis of difunctional PCN adhesives in which the terminal hydroxyl groups of a PCN-Diol reacts with one of two isocyanate groups of the diisocyanate molecule resulting in a PCN— Diisocyanate molecule. The free isocyanates then react with a reactive moiety (here an amine) present on the alkyl chain of the 4-alkylbenzene-1,2-diol derivative (here dopamine).

Example 8a: Synthesis of Adhesive 8a as an Example of Difunctional PCN Adhesive a) Activation of the Dopamine Derivative (Dopa):

Dopamine hydrochloride was activated as previously described. One molar equivalent of dopamine hydrochloride was dissolved into a minimum of anhydrous DMAc at room temperature. An equivalent amount of triethylamine was added to complex the hydrochloride salt from dopamine. The mixture was stirred for 30 minutes, yielding a cloudy solution. Triethylamine hydrochloride was separated from the activated dopamine by centrifuging for 10 minutes at 5000 rpm and −10° C. The activated dopamine was decanted from the solid triethylamine pellet and used immediately.

b) Synthesis of Isocyanate Terminated PCN Oligomers (Prepolymer 8a):

12.6 g of dialcohol terminated Poly(hexamethylene carbonate) diol (PCN) with an average molecular weight of 1048 g/mol ($\bar{n}=7$) was added to a dry 250 mL 3-neck flask and degassed under vacuum at 60° C. for 12 h. The flask was purged with argon and 50 mL anhydrous DMAc was added through a septum with stirring under argon protection. Once the reaction mixture was completely clear, it was cooled to room temperature. 5.3 g of LDI (5% molar excess to alcohol groups) was added to the reaction mixture with a syringe through a silicone rubber septum. The reaction mixture was then ramped to 60° C. over 4 hours, followed by a second ramp to 75° C. over an additional 4 hours. Finally, the reaction was stirred at 75° C. for 2 hours, then cooled to room temperature to give prepolymer 8a.

c) Synthesis of PCN Based Oligomeric Dopamine Adhesive (Adhesive 8a)

Prepolymer 8a was functionalized by adding 5.0 g activated dopamine in 100 mL of DMAc to the reaction mixture. An ice bath was used to dissipate heat from this rapid and exothermic step. The reaction was stirred for an additional 2 hours to ensure complete reaction, then the mixture was slowly poured into a 1:1 mixture of hexanes and diethyl ether (500 mL) at room temperature. The mixture was stirred vigorously for 1 hour, then stirring was ceased and the reaction mixture was cooled in the fridge. The liquid phase was decanted off, and Adhesive 8a was recovered from the walls of the beaker. It was re-dissolved in acetone (250 mL) and precipitated by pouring into cold methanol (500 mL) to remove any residual reaction by-products.

Example 9: Cytotoxicity Testing

Cytotoxicity Assays: In vitro cytotoxicity of adhesive formulations was assessed by direct contact with cells, according to ISO 10993-5 [35], which describes test methods to evaluate in vitro cytotoxicity of medical devices and, therefore, determine the in vitro biological response of mammalian cells using appropriate parameters. DNA mass quantification and Water-soluble tetrazolium (WST-1) assays were used to evaluate the toxicity of the formulations to a cell line. Negative and positive controls consisted of growth media with untreated cells and 5% Dimethyl sulfoxide (DMSO), respectively.

Cell Culture and Sample Preparation: A10 smooth muscle cell line (ATCC, CRL-1476™) were cultured in Dulbecco's modified Eagle's medium (DMEM), supplemented with 100 U mL$^{-1}$ penicillin/100 µg of streptomycin and 10% fetal bovine serum in a humidified atmosphere at 37° C. with 5% C02. The medium was changed every other day, allowing the cells to grow and reach confluency. When the cells reached 80-90% confluence, they were passaged following treatment with 0.25% trypsin-EDTA solution. This procedure was repeated until the cells entered their standard cellular cycle [36, 37]. Samples of adhesives were preconditioned in an incubator with DMEM for 24 h. Then, cells were seeded onto the samples, to which 200 µL of A10 suspension (approximately 25,000 cells/mL) was added. The seeded specimens were confined in the wells of a 96-well plate for 24 h, 72 h and 7 days.

DNA mass quantification: At each time-point, cells were lysed with ice-cold lysis buffer (0.05% Triton X-100, 50 mM EDTA in PBS) for 1 h and tested for DNA assay as previously described [37-39]. First, 0.1% Hoechst Dye 33258 was diluted in a Trizma base/NaCl/EDTA buffer (0.10 M Trizma base, 0.2 M NaCl and 0.001 M EDTA in dH2O, pH 7.4) and 100 µL was added to a 96-well plate (Microfluor 2 Black, VWR). Then, 10 µL of cell lysate was added to the dye and read against a calf thymus DNA standard in a fluorescence microplate reader (BioTek Cytation 3, Biotek, Winooski, Vt., USA), with the excitation wavelength set at 360 nm and the emission wavelength observed at 460 nm [36].

WST-1 assay: For the WST assay, after removing media and rinsing with 1× with PBS, 200 µL of DMEM was added to each well. Next, 20 µL of the WST reagent was added to each well and the microplate will be incubated at 37° C. with 5% C02 for 1 h. The absorbance was read using a multi-mode reader (BioTek Cytation 3, Biotek, Winooski, Vt., USA) at 450 nm, with a reference wavelength of 650 nm [36]. Cell viability (%) was obtained using the equation:

$$\text{Cell viability (\%)} = \left[1 - \left\{\frac{At - Ab}{At - Ac}\right\}\right] \times 100 [40].$$

Statistical analysis: Data was analyzed using the software PASW Statistics 21.0 (SPSS Inc, Chicago, Ill., USA). Two-Way analysis of variance (ANOVA) and Tukey's multiple comparison post-hoc tests will be used to determine a statistical significance between the groups for the DNA mass quantification and WST-1 assays. Homogeneity of variance and normality were verified with Levene's and Shapiro-Wilk tests, respectively. The confidence interval for all the tests will be set at 95%.

TABLE 1

DNA assay results for A10 cells exposed to select adhesives after 24 h, 72 h and 7 days incubation at 37° C. with 5% $CO_2$. Cell viability results are relative to values for DMEM negative control at each time point. 5% DMSO was used as a positive control. Results are expressed as Mean ± Standard Deviation, n = 4.

| Group | Relative DNA mass (%) | | |
|---|---|---|---|
| | 24 h | 72 h | 7 d |
| DMEM (Negative control) | 100.0 ± 9.2 | 100.0 ± 12.1 | 100.0 ± 21.1 |
| 5% DMSO (Positive control) | 15.3 ± 5.3 | 1.3 ± 1.9 | 1.4 ± 1.6 |
| Adhesive 2b | 102.6 ± 16.2 | 87.0 ± 6.0 | 89.2 ± 7.2 |
| Adhesive 2c | 104.3 ± 10.5 | 95.6 ± 10.1 | 88.3 ± 8.9 |
| Adhesive 5 | 128.8 ± 13.0 | 109.9 ± 28.2 | 71.9 ± 5.5 |
| Adhesive 3a | 74.7 ± 18.2 | 36.5 ± 7.2 | 48.8 ± 18.5 |

TABLE 2

WST-1 cell viability assay results for A10 cells exposed to select adhesives after 24 h, 72 h and 7 days incubation at 37° C. with 5% $CO_2$. Cell viability results are relative to values for DMEM negative control at each time point. 5% DMSO was used as a positive control. Results are expressed as Mean ± Standard Deviation, n = 4.

| Group | Relative Cell viability (%) | | |
|---|---|---|---|
| | 24 h | 72 h | 7 d |
| DMEM (Negative control) | 100.0 ± 6.5 | 100.0 ± 5.8 | 100.0 ± 12.3 |
| 5% DMSO (Positive control) | 18.4 ± 0.9 | 4.4 ± 1.1 | 1.0 ± 0.5 |
| Adhesive 2b | 77.1 ± 2.4 | 79.7 ± 10.0 | 74.0 ± 10.0 |
| Adhesive 2c | 69.3 ± 9.1 | 75.5 ± 4.2 | 77.4 ± 16.2 |
| Adhesive 5 | 83.5 ± 2.4 | 70.6 ± 8.0 | 74.5 ± 24.3 |
| Adhesive 3a | 100.2 ± 13.4 | 56.9 ± 3.9 | 60.5 ± 8.3 |

Tables 1 and 2 show that many of the adhesive systems exhibit cytocompatibility (70%) after at least 24 hrs of contact with the A10 cell lines, indicating their suitability for use in medical device applications.

Example 10: Determination of the Thermal Properties of a Bioadhesive

Melting and glass transition data was obtained by differential scanning calorimetry (DSC). Calorimetry studies were performed on a DSC Q200 (TA Instruments, Newcastle, Del., U.S.A.) equipped with a RCS90 refrigerated cooling system. Each sample (4-8 mg) was hermetically sealed into an aluminium DSC pan, and subsequently introduced into the DSC sample chamber continuously which was purged with a dry nitrogen flow of 60 mL/min. The sample was equilibrated at 100° C. for 2 minutes to erase thermal history and/or facilitate crosslinking in the presence of crosslinking agents. A modulation frequency with an amplitude of 1.0° C./minute was initiated, and the sample was then cooled at a rate of 10.0° C./min down to −80° C. where it was held isothermally for 2 min. Finally, the sample was heated from −80° C. to 100° C. at a rate of 10.0° C./min and held isothermally for an additional 2 minutes. Thermal properties were calculated from the thermograms with TA Universal Analysis 2000 software.

TABLE 3a

Glass transition temperature (Tg) of non-crosslinked adhesives and mixtures as determined by DSC from the midpoint of the Tg transition curve on the heating cycle. Samples were run in hermetically sealed aluminium DSC pans with 3-6 mg of sample per run. Tg values determined by the TA Universal Analysis 2000 software from samples run at 10° C./min with a continuous modulation at an amplitude of 1.0° C./ minute. Comparison between heat flow, reversable heat flow, and non-reversable heat flow thermograms were used to isolate the glass transition events based on their second order phase transition behaviour.

| Adhesive | Glass Transition Temperature—Tg (° C.) |
|---|---|
| Adhesive 1b | −51.7 ± 2.3 |
| Adhesive 2a | −1.2 ± 1.0 |
| Adhesive 2b | −21.5 ± 1.8 |
| Adhesive 2c | −40.8 ± 1.5 |
| Adhesive 3a | −8.1 ± 1.4 |
| Adhesive 5 | 14.2 ± 3.0 |
| Adhesive 7a | −18.2 ± 10.3 |
| Adhesive 8a | −32.0 ± 4.7 |
| Mixture (wt/wt %) 60% Adhesive 5a + 40% Adhesive 2b | 0.7 ± 2.3 |
| Mixture (wt/wt %) 70 Adhesive 5a + 30% Adhesive 2b | 6.6 ± 2.0 |
| Mixture (wt/wt %) 80% Adhesive 5a + 20% Adhesive 2b | 11.9 ± 0.6 |
| Mixture (wt/wt %) 90% Adhesive 5a + 10% Adhesive 2b | 18.0 ± 0.3 |

TABLE 3b

Glass transition temperature (Tg) of crosslinked adhesives as determined by DSC from the midpoint of the Tg transition curve on the heating cycle. Crosslinked samples were obtained upon handmixing of the crosslinking agent with the adhesive at room temperature at the desired weight ratios immediately prior to sample pan preparation. Samples were run in hermetically sealed aluminium DSC pans with 3-6 mg of sample per run. Tg values were determined by the TA Universal Analysis 2000 software from samples run at 10° C./ min with a continuous modulation at an amplitude of 1.0° C./ minute. Comparison between heat flow, reversable heat flow, and non-reversable heat flow thermograms were used to isolate the glass transition events based on their second order phase transition behaviour.

| Adhesive | Glass Transition Temperature—Tg (° C.) |
|---|---|
| Adhesive 2a + 5% wt/wt FeCh | 49.5 ± 0.4 |
| Adhesive 2a + 5% wt/wt $FePO_4$ | 49.0 ± 1.2 |
| Adhesive 2a + 5% wt/wt FeCit | 47.4 ± 2.1 |
| Adhesive 2a + 5% wt/wt $Na_3VO_4$ | 53.4 ± 2.0 |
| Adhesive 2a + 5% wt/wt $Na_2CO_3$ | 48.2 ± 0.8 |
| Adhesive 2a + 5% wt/wt TBAP | 53.8 ± 2.3 |
| Adhesive 2b + 5% wt/wt $FePO_4$ | −10.8 ± 0.6 |
| Adhesive 2b + 5% wt/wt TBAP | −11.6 ± 0.8 |
| Adhesive 5 + 5% wt/wt TBAP | 22.0 ± 0.9 |

Differential scanning calorimetry was used to determine the transition temperatures of the bioadhesives described herein. None of the adhesives displayed sharp or well-defined melting points; instead they all possessed well defined and narrow glass transition temperatures. These indicated the absence of crystalline domains and the inherent nature of their amorphous state, respectively. Higher glass transition temperatures are typical of glassy materials, whilst materials with lower glass transition temperatures remain amorphous for longer/until lower temperatures.

Variations in the glass transition temperatures of the non-crosslinked adhesives (Table 3a) were observed related to the inherent glass transition temperatures of the oligomeric backbone chemistry and were also related to oligomer length and catechol functionalization degree.

Adhesive mixtures which were physically blended (i.e., not chemically crosslinked; Table 3a) generally displayed only a single glass transition temperature between the range of the two mixtures, indicating complete solubilization of the adhesives with each other upon mixing. Typically, the resulting glass transition temperature was more heavily weighted towards the major weight constituent of the mixture, as can be seen from the changes in the mixing ratio between Adhesive 5a and Adhesive 2b in Table 3a.

Table 3b, on the other hand, shows that upon heating the adhesives in the presence of the crosslinking agents, the glass transitions shifted to notably higher temperatures, indicative of the successful rigidification of the low molecular weight-insoluble adhesives described herein. Importantly, Table 3b shows that similar degrees of rigidification could be obtained with the use of facile non-toxic crosslinking agents such as iron (III) phosphate, which is widely used in nutritional supplements for humans, as compared to more toxic crosslinkers such as the periodate (TBAP) or caustic iron (III) chloride.

However, while Table 3b shows a relative insensitivity of the adhesives to the nature of the crosslinking agent, it does reveal that the different adhesives do not respond to crosslinking-mediated rigidification in the same manner. For example, upon crosslinking, Adhesive 2a undergoes a change in Tg of ~50° C., whilst Adhesive 2b and Adhesive 5 undergo a substantially smaller increase in Tg of ~10° C. each. Consideration of the catechol group densities of the different adhesives does not readily explain this difference in the rigidification of the adhesives; both Adhesives 2a and 5 possess similar catechol group densities per unit mass of adhesive (2 mmol/g) whilst the catechol density of Adhesive 2b is 1.5 mmol/g. On the other hand, the steric complexities of the adhesives—which affect and eventually limit the interactions of the adhesive moieties with the crosslinkers—do increase with their molecular masses, indicating that the lower molecular weight systems are more amenable to rigidification upon crosslinking compared to larger molecular weight systems (MW of adhesives 2a, 2b and 5 are 1401, 2018 and 3019, respectively). Thus, with careful tuning based on informed structure-property correlations, it is possible to identify and select specific adhesive-only and/or adhesive-adhesive combinations that, when crosslinked, would present a range of tunable material properties such as the desired degree of rigidity, setting rate, and/or different degrees of hardness and/or flexibility.

Example 11: Testing Adhesion on Different Interfaces

This section presents evidence that the adhesives are functional with a variety of adherends, and, therefore, their utility for a wide range of medical device applications.

Example 11a: Skin/Glass

Figure 26:
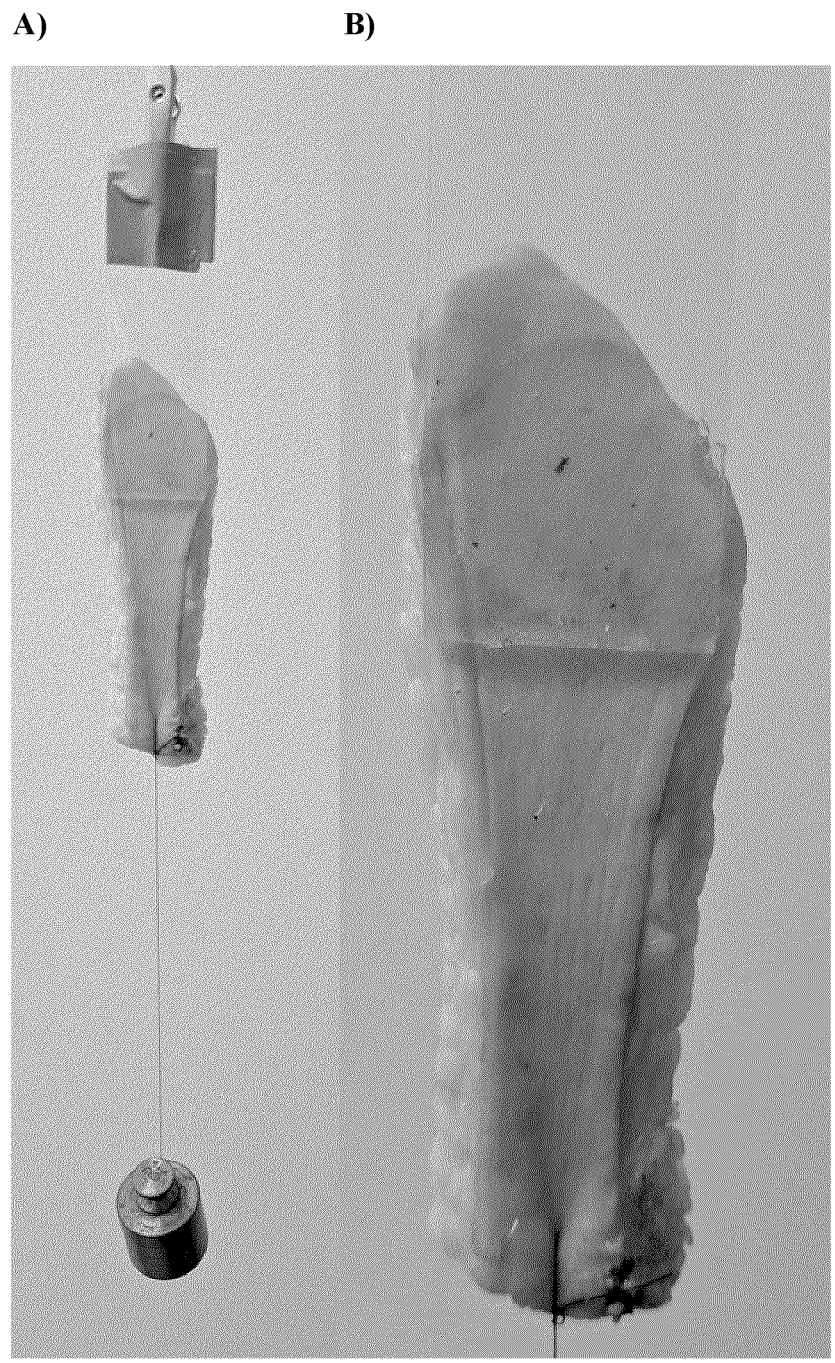
FIG. 26 shows an example of the use of the water insoluble Adhesive 2a to secure a piece of polymer film to porcine skin.

Porcine skin was fixed to a dry glass microscopy slide using Adhesive 2a adhesive. 100 mg of adhesive was spread evenly on a warmed glass slide and a strip (3.0 cm×10.0 cm×1.0 cm) of porcine skin freshly obtained from a local butcher was pressed by hand force onto the slide with the skin side in contact with the adhesive coated side of the glass slide for approximately 5 seconds. A 100 g brass weight was then sutured through the tissue and hung from the skin so that the weight of the tissue and brass weight was loaded entirely onto the biocompatible adhesive glass/skin bond. The adherend samples were left loaded and undisturbed at room temperature (approximately 22° C.). Photographs were taken 10 minutes after the weight was initially loaded (FIG. 26). Photo depicts a 100 g weight connected to porcine skin after hanging suspended by the skin/adhesive/polymer bond at room temperature for 10 minutes.

Example 11b: Bone/Bone

Figure 27:
FIG. 27 shows an example of the use of the water insoluble Adhesive 2a to secure bone to bone.

Porcine rib bones were bound together using Adhesive 2a adhesive. 50 mg of the adhesive was spread evenly on a 37° C. rib bone, that was previously immersed in a sterile saline solution (0.9% NaCl) at 37° C. for 1 hour and blotted with cotton gauze to remove excess saline just prior to adhesive application. A second porcine rib subjected to identical conditions was pressed by hand force firmly onto the first such that the area with the adhesive made contact with both ribs for approximately 5 seconds. A 100 g brass weight was tied around the lower rib and freely hung so that the weight of the bone and brass weight was held by the biocompatible adhesive bone/bone bond. The adherend samples were left loaded and undisturbed at room temperature (approximately 22° C.). Photographs were taken 10 minutes after the weight was initially loaded (FIG. 27). Photo depicts a 100 g weight connected to two porcine rib bones bound together by a bone/adhesive/bone bond after hanging suspended at room temperature for 10 minutes.

Example 11c: Bone/Skin

Figure 28:
FIG. 28 shows an example of the use of the water insoluble Adhesive 2a to secure porcine skin to bone.

Porcine rib and skin were bound together using Adhesive 2a adhesive. 50 mg of the adhesive was spread evenly on a warmed (~37° C.) rib bone and a piece of skin at room temperature was stuck to the rib. A suture was placed through the skin to secure it and allow it to hang freely. No load was applied, and photographs were taken immediately after the tissue samples were bound together (FIG. 28). Photo depicts a porcine rib bone bound to porcine skin by a bone/adhesive/skin bond after hanging suspended at room temperature for 10 minutes.

Example 11d: Skin/Skin

Figure 29:
FIG. 29 shows an example of the water insoluble Adhesive 2a to secure porcine skin to skin.

Porcine fatty skin tissues were bound together using Adhesive 2a adhesive. 50 mg of the adhesive was spread evenly onto a warmed (~37° C.) piece of skin tissue and a second piece of tissue was pressed onto the first for approximately 5 seconds. No load was applied, and photographs were taken immediately after the tissue samples were bound together. Photographs were taken immediately after the tissue samples were bound together (FIG. 29). Photo depicts porcine skin bound to porcine skin by a skin/adhesive/skin bond immediately after application at room temperature.

Example 11e: Bone/Polymer/Skin

Figure 30:
FIG. 30 shows an example of the water insoluble Adhesive 2a to secure porcine bone to a polymeric film and porcine skin to the same polymeric film.

A 2.0 cm×6.0 cm×0.4 mm piece of polycaprolactone (Mw=90 000 g/mol) was coated evenly on one side with 50 mg Adhesive 2b. One end of the tape was bound to the porcine rib bone and the other end of the polycaprolactone tape was bound to porcine skin. An even layer of 50 mg of Adhesive 2b was present at each interface between the polycaprolactone and the tissues. The bone and tissue specimens were affixed to the polycaprolactone by being briefly pinched (approximately 5 seconds for each interface) so that they overlapped with the adhesive coated area. The porcine bone was clamped to a retort stand so that the polycaprolactone and porcine skin was suspended hanging freely from the bone. A 100 g brass weight was fixed to the porcine skin with a suture and hung freely to load the test sample. The brass weight and testing specimens were fully supported by the Adhesive 2b adhesive at both the skin to polycaprolactone and bone to polycaprolactone interfaces. The adherend samples were left loaded and undisturbed at room temperature (approximately 22° C.). Photographs were taken 10 minutes after the weight was initially loaded (FIG. 30). This is an example of a soft tissue/device and device/hard tissue interfaces. Photo depicts a polymeric film bound at the top to a porcine rib bone and bound at the bottom to a piece of porcine skin. A 100 g weight is suspected such that the loading is simultaneously on both the polymer/adhesive/bone and polymer/adhesive/skin bond, and the photo was captured after hanging suspended at room temperature for 10 minutes.

Example 12: Testing Adhesion Strength

Adhesion strength is a major design criterion for any adhesive. Here we define adhesion strength in shear, in either compression or tension depending on the sample type. Adhesion strength values were obtained from the maximum stress (converted to Pa from the applied force and cross-sectional area in contact between the two substrates tested). Adhesion was tested using a variety of temperatures, substrates, and formulations with and without induced crosslinking.

In general, adhesives with higher crosslinking density, higher melting temperatures and/or higher Tg values were less elastic, with little or no plastic deformation and a catastrophic failure mechanism. Without wishing to be bound by a theory, this is typical of materials with reduced elasticity and reflective of elevated crosslinking and/or being tested in a rigid or glassy state where there is limited plastic deformation of the adhesive oligomers, thus limiting rearrangement and elastic deformation or strain hardening. The less rigid adhesives generally failed by a ductile failure mode following a degree of plastic deformation.

Example 12a: The Effect of Crosslinkers and Substrates

To determine the effect of different crosslinkers on adhesion strength, several oxidants and complexing agents were mixed into adhesives at different weight ratios and applied to samples and allowed to cure. Adhesion strength was measured using a compressive shear test.

Crosslinking agents in this test included the inorganic oxidants $Na_3VO_4$ and tetrabutylammonium (meta)periodate (TBAP), an inorganic base ($Na_2CO_3$), an organic complexing salt (iron (III) citrate—FeCit), and two inorganic complexing salts ($FeCl_3$ and $FePO_4$). Briefly, crosslinkers were hand mixed into different adhesives on glass slides with the aid of heat and immediately applied onto aluminum, ceramic or glass substrates using a contact area of 90 mm². Samples were loaded in shear on an Instron 4301 universal testing machine under modified ASTM D905-08 conditions.

TABLE 4a

Adhesion properties of bioadhesives using varying crosslinking agents and concentrations. Testing was conducted on an Instron 4301 universal testing machine with a 1000N load cell and an applied strain rate of 2 mm/min at ambient room temperature on standard sized samples consisting of two pieces of dry aluminium or ceramic or glass adherends with approximately 0.20 g of adhesive between surfaces. Contact surface areas were kept nearly constant (~90 mm²) for all samples in the set. Results are expressed as Mean ± standard deviation, n = 4. Glass is defined as commercially available plain glass slides. Ceramic samples are composed of calcium polyphosphate tablets.

| Adhesive, Crosslinking agent, Substrate | Adhesive Strength (MPa) |
|---|---|
| Adhesive 2a + 5% wt/wt $Na_3VO_4$ (Aluminium) | 2.7 ± 0.9 |
| Adhesive 2a + 2.5% wt/wt $Na_3VO_4$ (Aluminium) | 6.2 ± 1.9 |
| Adhesive 2a + 5% wt/wt $Na_2CO_3$ (Aluminium) | 3.0 ± 0.9 |
| Adhesive 2a + 2.5% wt/wt $Na_2CO_3$ (Aluminium) | 5.8 ± 2.8 |
| Adhesive 2a + 5% wt/wt $Na_3VO_4$ (Ceramic) | 1.2 ± 0.6 |
| Adhesive 2a + 5% wt/wt $Na_2CO_3$ (Glass) | 1.4 ± 0.5 |
| Adhesive 2a + 5% wt/wt TBAP (Aluminium) | 8.2 ± 2.7 |
| Adhesive 2a + 2.5% wt/wt TBAP (Aluminium) | 8.4 ± 2.2 |
| Adhesive 2a + 5% wt/wt FeCh (Aluminium) | 1.7 ± 0.5 |
| Adhesive 2a + 5% wt/wt $FePO_4$ (Aluminium) | 1.9 ± 0.9 |
| Adhesive 2a + 5% wt/wt FeCit (Aluminium) | 2.6 ± 0.7 |
| Adhesive 2b + 5% wt/wt $Na_2CO_3$ (Aluminium) | 0.9 ± 0.5 |
| Adhesive 2b + 2.5% wt/wt $Na_2CO_3$ (Aluminium) | 1.6 ± 0.9 |
| Adhesive 2b + 5% wt/wt $Na_3VO_4$ (Aluminium) | 1.2 ± 0.6 |
| Adhesive 2b + 2.5% wt/wt $Na_3VO_4$ (Aluminium) | 0.8 ± 0.5 |
| Adhesive 2b + 5% wt/wt $Na_3VO_4$ (Ceramic) | 0.3 ± 0.2 |
| Adhesive 2b + 5% wt/wt TBAP (Aluminium) | 1.7 ± 0.5 |
| Adhesive 2b + 2.5% wt/wt TBAP (Aluminium) | 0.8 ± 0.3 |
| Adhesive 2b + 5% wt/wt $FePO_4$ (Aluminium) | 0.6 ± 0.3 |
| Adhesive 2a + Adhesive 2b + 5% wt/wt $Na2CO_3$ (Aluminium) | 1.6 ± 0.5 |
| Adhesive 2a + Adhesive 2b + 5% wt/wt $NazCO_3$ (Glass) | 1.9 ± 0.2 |

TABLE 4b

Mechanical properties of bioadhesives on differing substrates tested at room temperature (~22° C.) without crosslinking agents under modified ASTM D905-08 conditions. Data obtained by compression lap shear strength test using an Instron 4301 universal testing machine, with a 1000N load cell and an applied strain rate of 2 mm/min. Testing was conducted on standard sized samples consisting of two pieces of dry adherends with approximately 0.20 g of adhesive between surfaces. Contact surface areas were kept constant (90 mm²) for all samples in the set. Results are expressed as Mean ± standard deviation, n = 4. Glass is defined as commercially available plain glass slides. Ceramic samples are composed of calcium polyphosphate tablets.

| Adhesive & Substrate | Adhesive Strength (MPa) |
|---|---|
| Adhesive 2a on glass | 1.7 ± 0.3 |
| Adhesive 2b on aluminium | 1 2 ± 1.0 |
| Adhesive 2b on ceramic | 1.6 ± 0.6 |
| Adhesive 2a + Adhesive 2b (50:50 wt %) on glass | 1.6 ± 0.2 |
| Adhesive 6 on aluminium | ND* |
| Adhesive 6 on glass | ND* |

*ND = No Data; unable to connect to adhesion testing apparatus without premature failure. This is consistent with expected results; i.e., materials without catechol groups are not adhesive.

Without the incorporation of the crosslinking agents (Table 4b), the adhesive strengths of all the adhesives were independent of the substrate employed—a characteristic indicative of the inherent cohesive susceptibility of the uncrosslinked adhesives at the test conditions (room temperature).

Table 4a shows that upon addition of the various crosslinking agents, the adhesion strength of Adhesive 2a could be increased five-fold. On the other hand, Adhesive 2b presented no apparent improvements in its cohesive strength with the use of oxidants or complexing agents (Table 4a). This difference in performance upon crosslinking between the adhesives can be directly linked to their crosslinked glass transition temperatures, recall from Table 3b that upon crosslinking, the Tg of Adhesive 2a moves to above room temperature, whilst that of Adhesive 2b is still well below room temperature. This means that under the adhesion strength test condition, the crosslinked Adhesive 2a is tested in its glassy state, while crosslinked Adhesive 2b is still flowable and thus easily sheared at room temperature. This result teaches that improving adhesion strength/crosslink density with the use of crosslinking agents is strongly dependent on the degree of rigidification that occurs during the curing process and, therefore, on the molecular weights of the adhesive, as was previously discussed in Example 10.

Example 12b: The Effect of Temperature on Adhesive Strength

Adhesives were tested at temperatures above and below their glass transition temperatures in order to determine the influence of temperature on their performance. Glass transition temperatures were determined using dynamic scanning calorimetry (DSC), and adhesion strength was measured using a compressive shear test. Results are reported in Table 4c for non-crosslinked samples.

TABLE 4c

Mechanical properties of bioadhesives tested approximately 20° C. above and 20° C. below the midpoint of their glass transition temperature (as determined by DSC) without crosslinking agents on rectangular aluminium stubs under modifiedASTM D905-08 conditions. Adhesive mixtures were prepared by cryogenic milling. Approximately 60 mg of the adhesive was applied evenly over the 2 cm$^2$ surface area. Testing was conducted after samples stabilized at the required testing temperatures. Data obtained by compression lap shear strength testing using Instron 4301 universal testing machine, with a 1000N load cell and an applied strain rate of 5.0 mm/min. Results are expressed as Mean ± standard deviation, n = 3.

| Adhesive | Tg (° C.) on heat) | Test Temp [°C] | Stress (MPa) Above Tg | Stress (MPa) Below Tg |
|---|---|---|---|---|
| Adhesive 2c | −40.8 ± 1.5 | −80, −20 | 0.22 ± 0.12 | 4.38 ± 0.85 |
| Adhesive 3a | −8.1 ± 1.4 | −80, −10 | 0.71 ± 0.71 | 2.24 ± 0.90 |
| Adhesive 5 | 14.2 ± 3.0 | 4, 37 | 1.07 ± 0.47 | 1.28 ± 0.62 |
| Adhesive 2b | −21.5 ± 1.8 | −80, 4 | 0.16 ± 0.08 | 3.84 ± 1.13 |
| Mixture (wt/wt %)— 90 Adhesive 5/ 10 Adhesive 2b | 18.0 ± 0.3 | 4, 37 | 1.36 ± 0.31 | 1.54 ± 0.64 |
| Mixture (wt/wt %)— 80 Adhesive 5/ 20 Adhesive 2b | 11.9 ± 0.6 | 4, 37 | 0.92 ± 0.42 | 1.52 ± 0.91 |
| Mixture (wt/wt %)— 70 Adhesive 5/ 30 Adhesive 2b | 6.6 ± 2.0 | −20, 37 | 0.87 ± 0.48 | 1.59 ± 0.08 |
| Mixture (wt/wt %)— 60 Adhesive 5/ 40 Adhesive 2b | 0.7 ± 2.3 | −20, 37 | 0.48 ± 0.38 | 1.19 ± 0.51 |

Table 4c shows the adhesion strengths of the adhesives at different temperatures. Since no oxidants were used in these experiments to induce crosslinking, the results presented reflect the natural cohesive strengths of the reported dry adhesive formulations. As is typical of all thermoplastic/hotmelt adhesives, the adhesives, without crosslinking, were vulnerable to the temperature at which they were tested, typically presenting higher adhesion strengths at temperatures well below their glass transitions.

In formulations with glass transitions far below 37° C., the adhesive strengths are considerably reduced at room temperature or physiological temperatures, and the adhesives fail cohesively. For example, Adhesive 2a and Adhesive 2b exhibit poor cohesion at simulated physiological temperatures, undergoing flow and creep behaviour when minimal forces are applied. However, when doped with an adhesive with a Tg closer to 37° C. (e.g. Adhesive 5), the glass transitions are shifted towards higher temperatures, allowing these materials to be functional at physiological temperatures, thereby increasing their utility.

Compared to all of the pure adhesives, Adhesive 5 has a uniquely high glass transition temperature which accounts for its high cohesive strengths well above its Tg (at 37° C.) without the necessity for a crosslinking agent. This feature is unique among the many formulations found in the patent literature which require co-oxidants to achieve practical cohesive strength within a finite period under wet conditions. This novel finding capitalizes on uniquely defined thermal transitions that the material undergoes. The polymer is naturally adhesive, even at room temperature.

Example 12c: Testing Adhesion Under Wet Conditions

Compared to the starting oligomers, the adhesives possess increased hydrophilicity on account of the urethane and urea linkages present in the adhesives, in addition to the already existing ester group linkages of the starting oligomers. While these are desirable for biodegradability, these same properties also can make the adhesives susceptible to failure due to water ingress during use.

Possible strategies to reduce water ingress include increasing the hydrophobic domains within the adhesive system by blending with more hydrophobic adhesives and/or additives such as high molecular weight (HMW) PCL, and/or increasing the crosslinking within the adhesive network so as to decrease the swelling potential of the adhesive itself whilst maintaining or improving the cohesive integrity of the system.

To assess the performance of the adhesives for use under surgical conditions, the adhesive strengths of various physically linked and chemically crosslinked adhesive samples were investigated. Adhesive mixtures were cryogenically milled, applied to aluminium stubs, and submerged in simulated body fluid (PBS) at 37° C. for 24 hrs. Adhesion strength was assessed using a compressive shear test. Results are presented in Table 4d alongside the dry strengths of the respective samples (tested at time 0 with equilibration to 37° C. prior to testing).

TABLE 4d

Mechanical properties of crosslinked bioadhesives tested at physiological temperatures (37° C.) on rectangular aluminium stubs under modified ASTM D905-08 conditions. Adhesive mixtures were prepared by cryogenic milling. Approximately 60 mg of the adhesive/adhesive blend was applied evenly over the 2 cm² surface area. Samples were submerged in PBS for 24 hrs at 37° C. Data was obtained by compression lap shear strength testing using Instron 4301 universal testing machine, with a 1000N load cell and an applied strain rate of 5.0 mm/min. Results are expressed as Mean ± standard deviation, n = 4. Dry strength refers to adhesion strength values obtained at 37° C. with no incubation period, and wet strength refers to adhesion strength values obtained after incubation in PBS solution at 37° C. for 24 hrs.

| Adhesive | Dry Strength (MPa) | Wet Strength (MPa) |
| --- | --- | --- |
| Adhesive 2a | 1.27 ± 0.51 | 0.40 ± 0.37 |
| Mixture (wt/wt %)—Adhesive 5:Adhesive 2b, 90:10 | 1.36 ± 0.30 | 1.82 ± 0.59 |
| Mixture (wt/wt %)—PCL:Adhesive 2a, 50:50 | 1.38 ± 0.42 | 0.19 ± 0.05 |
| Mixture (wt/wt %)—PCL:Adhesive 2a:Na$_2$CO$_3$, 50:45:5 | 2.34 ± 0.54 | 1.07 ± 0.23 |
| Mixture (wt/wt %)—PCL:Adhesive 2a:Na$_2$CO$_3$, 60:35:5 | | 0.75 ± 0.20 |
| Mixture (wt/wt %)—PCL:Adhesive 2a:Na$_2$CO$_3$, 35:60:5 | | 0.64 ± 0.24 |
| Mixture (wt/wt %)—PCL:Adhesive 2a:FeCl$_3$, 50:45:5 | 1.03 ± 0.28 | 0.41 ± 0.18 |
| Mixture (wt/wt %)—PCL:Adhesive 2a:FePO$_4$, 50:45:5 | 1.31 ± 0.37 | 1.33 ± 0.28 |
| Mixture (wt/wt %)—PCL:Adhesive 2a:FeCit, 50:45:5 | 1.42 ± 0.30 | 1.66 ± 0.64 |
| Mixture (wt/wt %)—PCL:Adhesive 2a:FeCl$_3$:Na$_2$CO$_3$, 50:45:2.5:2.5 | 0.98 ± 0.50 | 0.20 ± 0.06 |
| Mixture (wt/wt %)—PCL:Adhesive 2a:FePO$_4$:Na$_2$CO$_3$, 50:45:5 | 1.26 ± 0.29 | 1.30 ± 0.41 |
| Mixture (wt/wt %)—PCL:Adhesive 2a:FeCit:Na$_2$CO$_3$, 50:45:5 | 1.19 ± 0.45 | 1.5 ± 0.58 |
| Mixture (wt/wt %)—Adhesive 2a:FePO$_4$, 95:5 | 1.33 ± 0.37 | 0.87 ± 0.27 |
| Mixture (wt/wt %)—Adhesive 2a:FeCl$_3$, 95:5 | 3.82 ± 0.75 | 1.23 ± 0.36 |
| Mixture (wt/wt %)—Adhesive 2a:Na$_2$CO$_3$, 95:5 | 1.10 ± 0.30 | 0.35 ± 0.33 |
| Mixture (wt/wt %)—Adhesive 2a:TBAP, 95:5 | 1.59 ± 0.21 | 0.89 ± 0.50 |

Table 4d shows that for many of the tested non-chemically crosslinked systems, the adhesive strengths, whilst strong in shear at 37° C., failed cohesively after a 24 hr of incubation under wet conditions. Thus, inducing physical chain entanglement networks in adhesive-adhesive blends and/or increasing hydrophobic content alone may not be sufficient for adhesive devices intended for use in wet conditions.

On the other hand, the best strength retention performances were obtained when the adhesives were blended with both PCL and crosslinkers. Without wishing to be bound by a theory, it is possible that the inorganic salts function as both crosslinkers and second phase strengtheners, and PCL is beneficial in wet environments to slow leaching or dissolution of the second phase strengtheners from the adhesive blends.

The effect of neutral soluble (NaCl) and basic insoluble (tricalcium phosphate) salts on the strength retention of the adhesives was further investigated in order to further understand the significance of the crosslinking reactions compared to phase strengthening roles of the inorganic salts. Results are presented in Table 4e.

TABLE 4e

Mechanical properties of crosslinked bioadhesives tested at physiological temperatures (37° C.) on rectangular aluminium stubs under modified ASTM D905-08 conditions. Adhesive mixtures were prepared by cryogenic milling. Approximately 50 mg of the adhesive blend was applied (without the aid of heat to induce crosslinking) evenly over the 2 cm² surface area. Samples were submerged in PBS for 24 hrs at 37° C. Data obtained by compression lap shear strength testing using Instron 4301 universal testing machine, with a 1000N load cell and an applied strain rate of 5.0 mm/min. Results are expressed as Mean ± standard deviation, n = 4.

| Additive | Wet Strength (MPa) |
| --- | --- |
| Tricalcium phosphate (TCP) | 0.74 ± 0.03 |
| Sodium chloride (NaCl) | 0.41 ± 0.28 |
| Sodium carbonate (Na$_2$CO$_3$) | 1.23 ± 0.27 |
| PCL (control) | 0.67 ± 0.14 |

It was assumed that if phase strengthening alone were responsible for the wet adhesion strengths, then only the insoluble salt (TCP) would have presented any improvements compared to the soluble neutral (NaCl) and basic (Na$_2$CO$_3$) salts and the control (PCL). Alternately, if pH-induced crosslinking alone was responsible for the wet adhesion strengths, then both Na$_2$CO$_3$ and TCP would present the desired strength retention values. Table 4e, however, shows that neither of these were the case—only the soluble but basic Na$_2$CO$_3$ salt presented any significant wet strength retention value. Without wishing to be bound by theory, sodium carbonate may dissolve in the presence of water to increase the local pH surrounding the adhesive, possibly stimulating oxidation of the dopamine residues, thus resulting in pH-induced crosslinking. In the presence of PCL, the adhesive-PCL chain entanglements may facilitate localized pooling of the basic solution, affording the pH-induced crosslinking reaction time to occur.

Overall, these results reinforce the importance of increasing both the crosslinking density and the hydrophobic content within the adhesives in order to improve adhesive strength.

Example 13: Testing Adhesion Under Wet Conditions on Biological Tissues (Bone)

Ideally, bioadhesive devices will function in wet, biofouled conditions at physiological temperatures. Additionally, the adhesives cannot rely on solvent drying for curing and should not be cytotoxic or release cytotoxic degradation products. These are the major challenges of surgical adhesive development. In particular, water ingress and/or solubility is the downfall of many adhesives, especially when they are not fully dry from solvents. The suitability of these adhesives for use in surgical applications was assessed using adhesive tests on samples which were wet or submerged for 24 h. However, submerged samples do not reflect the in vivo environment, but more show the resistance to water ingress. In fact, maintaining strength in vivo may actually prove easier, as there is far less diffusion and available water at the implant.

Example 13a: Water Ingress

Compared to the starting oligomers, the adhesives possess increased hydrophilic domains on account of the urethane and urea linkages present in the adhesives, in addition to the already existing ester group linkages of the starting oligomers. While these are desirable for biodegradability, these same properties also can make the adhesives susceptible to failure due to water ingress during use. To reduce water ingress, high molecular weight (HMW) PCL and sodium carbonate (a cross-linking agent) were combined with the adhesives. HMW PCL increases the hydrophobicity of the adhesive due to the intrinsic hydrophobicity of the PCL itself. Without wishing to be bound by a theory, sodium carbonate may act as both a second phase strengthener and a cross-linker. It will dissolve in the presence of water to increase the local pH surrounding the adhesive, possibly stimulating oxidation of the dopamine residues, thus resulting in crosslinking. This crosslinking could further reduce water ingress and support adhesion. Both additives may not be necessary to prevent ingress, especially because of the low surface area exposed to physiological fluid in vivo; however, both are shown here as proof of principle.

Wet Bone Substrate Preparation

Process of Preparing Adhesives for the Device:

Prior to testing, the adhesives were processed to incorporate different mixtures of specific adhesives or additives. Additives can be oxidants, polymers or second phase strengtheners. Here we combined Adhesive 2a with PCL (~90 kDa) and $Na_2CO_3$ at a 35:60:5 ratio, respectively, for protection against water ingress. HMW PCL increases hydrophobicity and $Na_2CO_3$ provides second-phase strengthening and the possibility for pH induced crosslinking in the event of water ingress. The adhesive mixtures were homogenized by cryo-milling on a Retsch CryoMill (Retsch, DE) equipped with a 50 mL steel milling jar with 4 steel ball bearings. Samples were cooled to −196° C. using one 10 min precooling cycle prior to 8×5-minute cryomilling cycles at 30 Hz. Adhesive mixtures were allowed to return to room temperature before being removed from the steel milling jar. The finely powdered, homogenized adhesive mixtures were transferred to scintillation flasks using a cooled polyethylene funnel and stored at −20° C. until use.

Flesh was removed from porcine rib bones and the surfaces were washed using aqueous detergent and ethanol to remove fats and residual material. Ribs were submerged in a phosphate buffered saline (PBS, Sigma) and allowed to incubate for at least 5 minutes before testing.

Preparation of Support Material:

PCL sheets were prepared by hot pressing using a Carver laboratory press. 4.6 g of PCL pellets (MW=90,000 g/mol, Sigma) were placed in a stainless-steel mold with a template $15.0 \times 20.0 \times 4 \times 10^2$ cm. The mold was placed on the platen between PTFE liners. Platens were heated to 190° C., and the pellets were heated until translucent. A top sheet was applied to the melt and ~2 metric tonnes of pressure was applied, pressing the melted polymer pellets into the mold. Locking vice grips were then attached to the plates on three sides to maintain pressure when removing from the press. Full pressure was held for ~30 s before slowly being released. The template was plunged into a sink filed with cold water to quench the polymer films from the melt. When the plates were cold, the vice grips were removed, and the PCL sheet was carefully removed from the mold. Sheets were trimmed to the mold dimensions with scissors, and further cut into 1.0×4.0 cm strips. An area of 1.5×1.0 cm was marked on each strip for consistent adhesive application. Marked regions on the strips were crimped using vice-grips to increase flexibility and provide a texture. PCL strips were plasma treated for 2 min under a partial oxygen atmosphere using a plasma cleaner (Harrick Plasma, USA) with an attached oxygen tank.

Preparation of Device:

To prepare samples, the adhesive formulation was warmed to room temperature before exposing to atmosphere (preventing condensation). The adhesive formulation was warmed using a forced air, electric heat gun to allow for spreading onto the bone using a spatula. The PCL strip was pressed by hand onto the adhesive for ~10 s to form the adhesive backing. Wet bones were incubated for 5 minutes in PBS and blotted dry before applying the adhesive. Samples were incubated at 37° C. for 24 h in either air or tap water before testing.

A commercially available, surgical cyanoacrylate-based adhesive was used as a control, but due to some limitations the application protocol was adapted. Bone samples were prepared in the same manner. The adhesive was applied to the wet bone surface and the PCL film was applied to the adhesive. However, due to slow curing of the commercial adhesive, the film was held for up to 5 minutes before moving to incubator. In one case, lab tape was wrapped around the bone to hold the PCL in place while the adhesive cured for 5 minutes. Delamination (due to incomplete curing) was observed on the edge of most samples and additional cyanoacrylate was added to the edges to accommodate.

Samples were loaded mechanically, immediately after removing from the 37° C. environment. Mechanical testing was performed using an Instron 4301 Universal Testing Machine (Instron) with a 200 N load cell and an applied strain rate of 5 mm/min in tensile mode. Samples were clamped ~1 mm below the tape application site on the bone and 2.5 cm above the bone on the tape side. Tests were finished after failure occurred or yielding in the PCL strip was observed. Failure mechanism was recorded by visual inspection after failure.

TABLE 5a

Mechanical properties of an adhesive blend (Adhesive 2a:PCL (~90 kDa):$Na_2CO_3$ at a 35:60:5 w/w ratio) obtained by modified lap shear testing using Instron 4301 universal testing machine, with a 200N load cell and an applied strain rate of 5 mm/min. Results are shown as means ± standard deviations and are reported for the adhesive blend on dry (uncrosslinked), PBS wetted (induced crosslinking) and submerged porcine bone (induced crosslinking), compared to a commercially available surgical cyanoacrylate (Covidien surgical adhesive).

| Sample Condition | Peak Force [N] | Peak Stress [kPa] | N value |
|---|---|---|---|
| Dry bone | 52.82 ± 6.87 | 264.08 ± 34.36 | n = 3; 3* |
| PBS-Wetted bone | 46.97 ± 3.09 | 234.86 ± 15.46 | n = 3; 1* |
| Submerged bone (in water) | 44.07 ± 24.42 | 220.34 ± 122.10 | n = 8 |
| Wet bone—cyanoacrylate | 67.90 ± 6.70 | 339.52 ± 33.51 | n = 3 |

Asterisks indicate the number of adhesive failures.

No significant difference was observed between the dry, wet and submerged bone samples using ANOVA analysis, indicating that the inclusion of the hydrophobic PCL segments and/or pH-induced crosslinking were effective for preventing/reducing water ingress within the adhesives upon use.

In all conditions, most failures occurred in the PCL film, and were observed as necking occurring at the tape region which did not overlap the bone with a resulting drop in the observed stress. Where failures did not occur in the tape region, the systems failed adhesively, as indicated by the asterisks in the table above. These results show that the cohesive integrity of the adhesive systems remained intact when used under wet conditions (i.e., on wet systems and upon submersion).

Further, the tested adhesive performed as well as commercial, surgical cyanoacrylate even after being submerged for 24 h, indicating the commercial suitability of the adhesive formulations presented herein. A further advantage of the claimed adhesives compared to commercial counterparts such as that used herein is the ease of use; as reported above, the commercial adhesive was very slow curing, and required extra effort and time to keep the adherends in position while the adhesive set. On the other hand, the claimed adhesives of this work 'set' immediately upon heat spreading/contact.

Example 13b: Testing Effect of Physiological Fluids on Adhesion

To test the effect of physiological fluids on adhesion of a polymer film to bone, tensile tests were conducted on samples submerged in varying solutions for 24 h.

Adhesive was prepared by combining Adhesive 2a with PCL (~90 kDa) and $Na_2CO_3$ at a 35:60:5 ratio, respectively, as described above. Adhesive was applied to the bone and gently heated using a heat lamp. PCL (90 kDa) film was cut into 1×4 cm pieces, crimped and plasma treated before application. The strips were applied to warm bone-adhesive samples and pressed for ~10 s. The overlap area was held constant at ~2 $cm^2$. Samples were submerged in water (control), PBS and equine blood (void of clotting factors) and incubated at 37° C. for ~24 h. After incubation, samples were rinsed with ultrapure water and held at 37° C. until testing.

Samples were loaded mechanically, immediately after removing from the 37° C. environment. Mechanical testing was performed using an Instron 4301 Universal Testing Machine (Instron) with a 100 N load cell and an applied strain rate of 5 mm/min in tensile mode. Samples were clamped ~1 mm below the tape application site on the bone and 2.5 cm above the bone on the tape side. Tests were finished after failure occurred or yielding in the PCL strip was observed. Failure mechanism was recorded by visual inspection after failure.

Data analysis was performed with IBM SPSS Statistics version 25.0. One-way ANOVA and Tukey post-hoc tests were used to analyze data comparing the different physiological solutions. The level of significance was set at 5%.

TABLE 5b

Adhesive strength values of polymer film with Adhesive 2a combined with PCL and $Na_2CO_3$ (35:60:5 ratio) to bone submerged in different physiological solutions. Data was generated in a tensile test at a strain rate of 5 mm/min with an overlap area of 2 $cm^2$. Results are shown as mean ± standard deviation (n = 3).

| Sample Condition | Peak Force [N] | Peak Stress [kPa] | N value |
|---|---|---|---|
| Water | 41.03 ± 11.05 ab | 205.16 ± 55.29 ab | 3 |
| PBS | 37.73 ± 15.07 b | 172.04 ± 46.74 b | 3 |
| Blood | 56.41 ± 3.20 a | 282.06 ± 15.99 a | 3 |

No statistical significance was found between the peak force values for samples incubated in water and PBS, while samples incubated in blood exhibited significantly higher values (Table 5).

Figure 31:
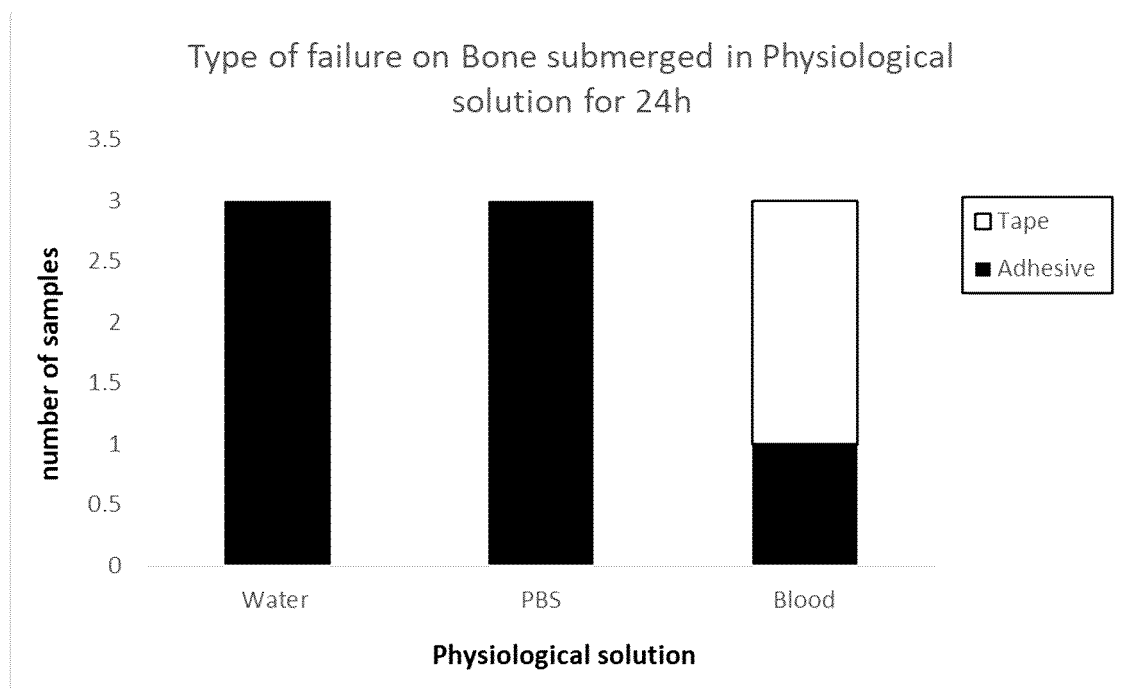
FIG. 31 shows failure modes for samples incubated in physiological fluids for 24 h.

All samples submerged in water and PBS failed adhesively whereas two of the three samples incubated in blood failed within the tape (observed as necking occurring at the tape region which did not overlap the bone, similar to what was presented in Example 13a). The bar graph (FIG. 31) shows the failure modes for the samples incubated in physiological fluids for 24 h. All sample preparation was done in a similar manner. Evidently, higher failure forces exhibited by samples incubated in blood are consistent with both stronger cohesive and adhesive performance of the adhesives under simulated real-use conditions.

Example 14: Testing Effect of Residual Solvent on Adhesive Performance

Residual solvent is a major challenge for bioadhesives. Synthesis in the presence of a solvent requires rigorous drying protocols to fully remove solvent, as solvents are often cytotoxic, and could accelerate in water ingress.

To test the effect of residual solvent on mechanical properties of uncrosslinked adhesive increasing amounts of solvent were incorporated into adhesive and mechanical properties were measured using a modified lap shear test. This experiment was designed to mimic both incomplete drying of the adhesive after synthesis, and what occurs when solvents are utilized for adhesive spreading and/or adhesive application.

To incorporate increasing amounts of solvent into adhesives, the process started with dry Adhesive 5. Using cryogenic milling 0, 5, 10 and 50 wt % anhydrous ethanol were incorporated into aliquots of adhesive. Briefly, ethanol was added dropwise to a specific mass percent of the adhesive. Adhesive/solvent mixtures were added to a large 50 mL steel milling canister containing 4 ball-bearings. Adhesive/ethanol mixtures were homogenized using cryogenic milling on a Retsch Cryomill at −196° C. Mixtures were milled for 3 cycles at 30 Hz with ~5 minutes of cooling between cycles. Adhesive-ethanol mixtures were transferred to scintillation vials and stored at −20° C. before use.

Aluminum stubs were prepared and cleaned with acetone. The surface of each stub was smooth, and a 2×1 cm area was indicated to ensure constant overlap area. ~60 mg of each adhesive-ethanol mixture was spread onto the stubs and an overlapping stub was applied by hand and pressed together for ~10 s. 0 and 5 wt % ethanol adhesives required some heat for spreading. Overlap area was held constant at 2 $cm^2$. Values could not be obtained for 50 wt % ethanol adhesive, as the cohesive strength was insufficient to hold the aluminum stubs together. Even at 10 wt % ethanol, the adhesive exhibited insufficient strength; the force of gravity resulted in deformation. 4 repeats of 0, 5, and 10 wt % ethanol adhesives were prepared and kept at room temperature for ~1 hr before testing.

Samples were tested on a Universal Testing Machine (Instron) under compression, using a modified lap shear test, at a strain rate of 5 mm/min. Stress and displacement data were recorded.

Figure 32:
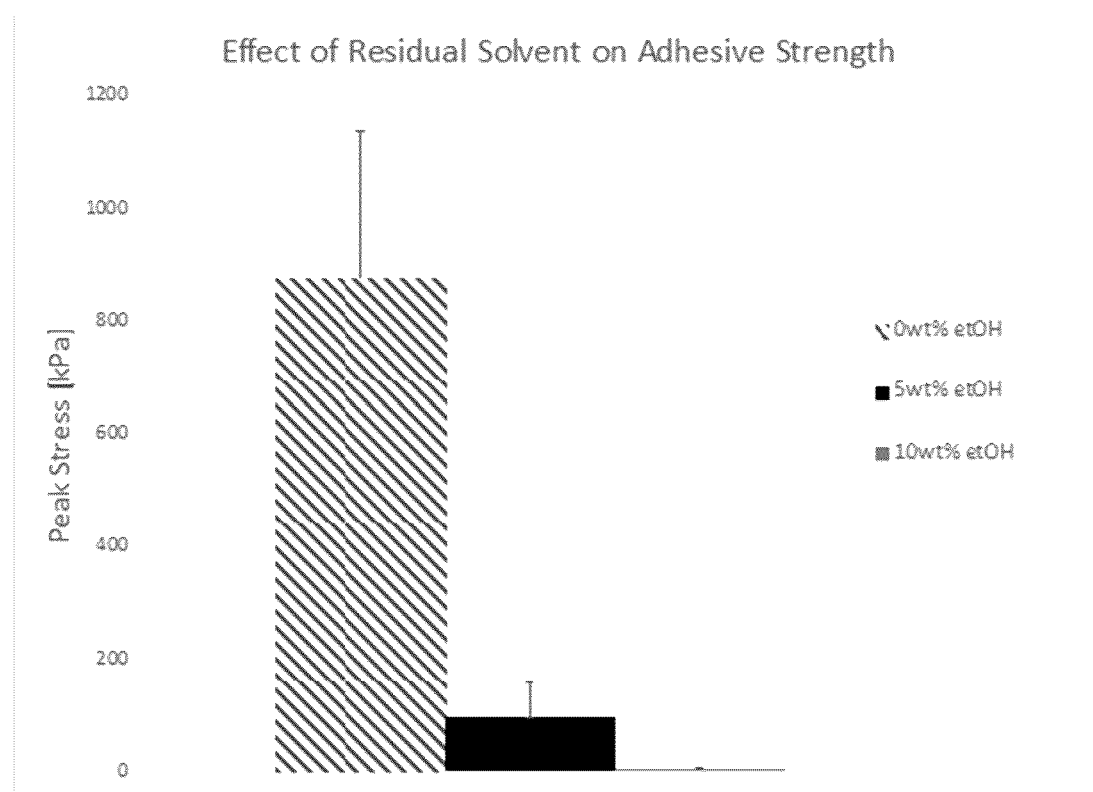
FIG. 32 shows the effect of residual solvent on the adhesive strength of the water insoluble Adhesive 5.

Increasing amounts of residual ethanol affected the cohesive strength of Adhesive 5. FIG. 32 shows adhesive strength with increasing residual solvent. 5 wt % ethanol reduced adhesive strength by 9×. Data was generated in compression using a modified lap shear test at a strain rate of 5 mm/min on aluminum stubs with an overlap area of 2 $cm^2$. Samples were tested at room temperature. Error bars indicate standard deviation (n=4). Doubling solvent to 10 wt % further reduced adhesive strength by ~30×.

Clearly, increasing amounts of residual solvent decreases the cohesive strength of adhesives.

REFERENCES

[1] P. Spencer, Q. Ye, J. Park, E. M. Topp, A. Misra, O. Marangos, Y. Wang, B. S. Bohaty, V. Singh, F. Sene, Adhesive/dentin interface: the weak link in the composite restoration, Annals of biomedical engineering 38(6) (2010) 1989-2003.

[2] B. Petersen, A. Barkun, S. Carpenter, P. Chotiprasidhi, R. Chuttani, W. Silverman, N. Hussain, J. Liu, G. Taitelbaum, G. G. Ginsberg, Tissue adhesives and fibrin glues: November 2003, Gastrointestinal endoscopy 60(3) (2004) 327-333.

[3] W. D. Spotnitz, Fibrin sealant: the only approved hemostat, sealant, and adhesive—a laboratory and clinical perspective, ISRN surgery 2014 (2014).

[4] R. Chivers, R. Wolowacz, The strength of adhesive-bonded tissue joints, International journal of adhesion and adhesives 17(2) (1997) 127-132.

[5] I. Peripheral, Toxicity of Alkyl 2-Cyanoacrylates.

[6] D. Lu, H. Wang, T. e. Li, Y. Li, X. Wang, P. Niu, H. Guo, S. Sun, X. Wang, X. Guan, Versatile Surgical Adhesive and Hemostatic Materials: Synthesis, Properties, and Application of Thermoresponsive Polypeptides, Chemistry of Materials 29(13) (2017) 5493-5503.

[7] D. F. Farrar, Bone adhesives for trauma surgery: A review of challenges and developments, International Journal of Adhesion and Adhesives 33 (2012) 89-97.

[8] L. Sanders, J. Nagatomi, Clinical applications of surgical adhesives and sealants, Critical Reviews™ in Biomedical Engineering 42(3-4) (2014).

[9] R. Bitton, E. Josef, I. Shimshelashvili, K. Shapira, D. Seliktar, H. Bianco-Peled, Phloroglucinol-based biomimetic adhesives for medical applications, Acta biomaterialia 5(5) (2009) 1582-1587.

[10] M. Yu, J. Hwang, T. J. Deming, Role of L-3, 4-dihydroxyphenylalanine in mussel adhesive proteins, Journal of the American Chemical Society 121(24) (1999) 5825-5826.

[11] H. Lee, B. P. Lee, P. B. Messersmith, A reversible wet/dry adhesive inspired by mussels and geckos, Nature 448(7151) (2007) 338.

[12] B. P. Lee, P. B. Messersmith, J. N. Israelachvili, J. H. Waite, Mussel-inspired adhesives and coatings, Annual review of materials research 41 (2011) 99-132.

[13] J. H. WAITE, Adhesion in byssally attached bivalves, Biological Reviews 58(2) (1983) 209-231.

[14] H. G. Silverman, F. F. Roberto, Understanding marine mussel adhesion, Marine biotechnology 9(6) (2007) 661-681.

[15] B. P. Lee, J. L. Dalsin, J. L. Murphy, L. Vollenweider, A. N. Lyman, F. Xu, J. White, W. D. Lew, M. Brodie, Adhesive compounds and methods use for hernia repair, Google patents, 2016.

[16] B. P. Lee, L. Vollenweider, J. L. Murphy, F. Xu, J. L. Dalsin, J. Virosco, W. Lew, J. White, Bioadhesive constructs, Google patents, 2013.

[17] P. B. Messersmith, J. L. Dalsin, B. P. Lee, S. A. Burke, DOPA-functionalized, branched, poly (aklylene oxide) adhesives, Google patents, 2014.

[18] J. L. Dalsin, B. P. Lee, L. Vollenweider, S. Silvary, J. L. Murphy, F. Xu, A. Spitz, A. Lyman, Multi-armed catechol compound blends, Google patents, 2014.

[19] B. P. Lee, S. Silvary, J. L. Murphy, Multibranched bioadhesive compounds and synthetic methods therefor, Google patents, 2017.

[20] P. B. Messersmith, L. He, D. E. Fullenkamp, pH responsive self-healing hydrogels formed by boronate-catechol complexation, Google patents, 2017.

[21] M. Szycher, Szycher's dictionary of biomaterials and medical devices, Routledge 2019.

[22] E. J. Beckman, M. Buckley, S. Agarwal, J. Zhang, Medical adhesive and methods of tissue adhesion, Google patents, 2007.

[23] M. Giannini, C. A. G. Arrais, P. M. Vermelho, R. Reis, L. Santos, E. R. Leite, Effects of the solvent evaporation technique on the degree of conversion of one-bottle adhesive systems, Operative dentistry 33(2) (2008) 149-154.

[24] I. V. Luque-Martinez, J. Perdigão, M. A. Muñoz, A. Sezinando, A. Reis, A. D. Loguercio, Effects of solvent evaporation time on immediate adhesive properties of universal adhesives to dentin, Dental Materials 30(10) (2014) 1126-1135.

[25] M. Suzuki, S. Tsuge, T. Takeuchi, Gas chromatographic estimation of occluded solvents in adhesive tape by periodic introduction method, Analytical Chemistry 42(14) (1970) 1705-1708.

[26] F. Scognamiglio, A. Travan, I. Rustighi, P. Tarchi, S. Palmisano, E. Marsich, M. Borgogna, I. Donati, N. de Manzini, S. Paoletti, Adhesive and sealant interfaces for general surgery applications, Journal of Biomedical Materials Research Part B: Applied Biomaterials 104(3) (2016) 626-639.

[27] A. Duarte, J. Coelho, J. Bordado, M. Cidade, M. Gil, Surgical adhesives: Systematic review of the main types and development forecast, Progress in Polymer Science 37(8) (2012) 1031-1050.

[28] P. Kord Forooshani, B. P. Lee, Recent approaches in designing bioadhesive materials inspired by mussel adhesive protein, Journal of Polymer Science Part A: Polymer Chemistry 55(1) (2017) 9-33.

[29] N. Annabi, A. Tamayol, S. R. Shin, A. M. Ghaemmaghami, N. A. Peppas, A. Khademhosseini, Surgical materials: Current challenges and nano-enabled solutions, Nano today 9(5) (2014) 574-589.

[30] W. D. Spotnitz, S. Burks, Hemostats, sealants, and adhesives: components of the surgical toolbox, Transfusion 48(7) (2008) 1502-1516.

[31] K. A. Vakalopoulos, F. Daams, Z. Wu, L. Timmermans, J. J. Jeekel, G.-J. Kleinrensink, A. van der Ham, J. F. Lange, Tissue adhesives in gastrointestinal anastomosis: a systematic review, Journal of Surgical Research 180(2) (2013) 290-300.

[32] G. Odian, Principles of polymerization, John Wiley & Sons 2004.

[33] C. M. Whyne, R. M. Pilliar, J. A. Fialkov, P. Santerre, E. Regev, Bone stabilization device and method of production, European Patent Office, 2015, p. EP2879600A4.

[37] C. M. Whyne, R. M. Pilliar, J. A. Fialkov, P. Santerre, E. Regev, Bone stabilization device and method of production, in: W. I. P. Organization (Ed.) WO2014019083A1 2015.

[35] Iso, Biological evaluation of medical devices-Part 5: Tests for in vitro cytotoxicity, International Organization for Standardization Geneve, Switzerland, 2009.

[36] J. W. C. Cheung, E. E. Rose, J. P. Santerre, Perfused culture of gingival fibroblasts in a degradable/polar/hydrophobic/ionic polyurethane (D-PHI) scaffold leads to enhanced proliferation and metabolic activity, Acta biomaterialia 9(6) (2013) 6867-6875.

[37] S. Sharifpoor, C. A. Simmons, R. S. Labow, J. P. Santerre, A study of vascular smooth muscle cell function under cyclic mechanical loading in a polyurethane scaffold with optimized porosity, Acta biomaterialia 6(11) (2010) 4218-4228.

[38] L. A. Matheson, G. N. Maksym, J. P. Santerre, R. S. Labow, Differential effects of uniaxial and biaxial strain on U937 macrophage-like cell morphology: Influence of extracellular matrix type proteins, Journal of Biomedical Materials Research Part A 81(4) (2007) 971-981.

[39] L. A. Matheson, J. P. Santerre, R. S. Labow, Changes in macrophage function and morphology due to biomedical polyurethane surfaces undergoing biodegradation, Journal of cellular physiology 199(1) (2004) 8-19.

[40] P. Makvandi, M. Ghaemy, A. A. Ghadiri, M. Mohseni, Photocurable, Antimicrobial Quaternary Ammonium-modified Nanosilica, Journal of dental research (2015)

The invention claimed is:
1. A device comprising:
a support;
and
a water insoluble adhesive on at least one bonding site on a surface of the support, the adhesive comprising:
a compound of structure 1

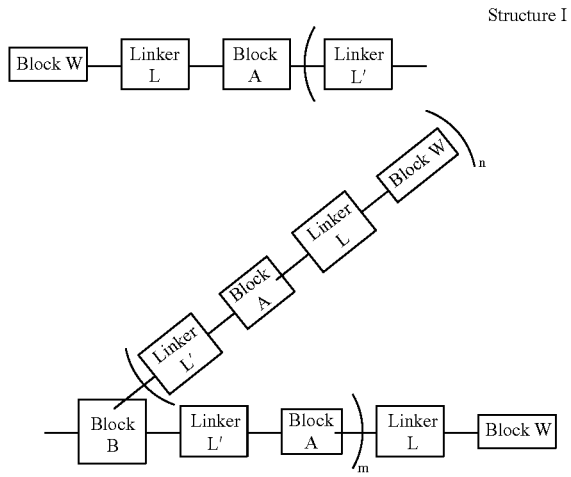

Structure I wherein
the compound is water insoluble;
the compound has a Tg lower than 25° C.;
B is a branched or unbranched oligomer derived from a polyester, polyether, polyalkylene glycol, polysilicone or polycarbonate with a MW<10,000 g/mol;
Linker L is an urethane, urea bond, or amide bond;
Linker L' is an urethane or urea bond;
A is a chain extender of Mw s 3000 g/mol comprising substituted or unsubstituted alkyl, cycloalkyl and/or aromatic groups;

W is a terminal adhesive selected from an adhesive benzene-1,2-diol derivative or an adhesive benzene-1,2,3-triol derivative;
m is 0 or 1; and
n is 0, 1, 2, 3 or 4; or
a cross-linked polymer produced by cross-linking compounds of structure 1.

2. The device of claim 1, wherein the adhesive comprises a compound of structure 1 and a cross-linking agent, wherein the cross-linking agent promotes covalent cross-linking of the terminal adhesive with another terminal adhesive and/or of the terminal adhesive with tissue.

3. The device of claim 1 wherein the adhesive comprises a cross-linked polymer prepared by combining the compound of structure 1 with a crosslinking agent or a curing agent preferably selected from sodium carbonate and/or iron(III) salts.

4. The device of claim 1 wherein the adhesive is hydrolysable and/or enzyme degradable.

5. The device of claim 1, wherein the support comprises a plurality of surfaces each having at least one bonding site thereon.

6. The device of claim 1, wherein the support comprises a biocompatible sheet structure.

7. The device of claim 6 wherein the support comprises a plurality of bonding sites and wherein the bonding sites include pores extending through the biocompatible sheet structure, and wherein the adhesive fills the pores.

8. The device of claim 6, wherein the sheet comprises first and second opposed sheet surfaces and both the first and second opposed sheet surfaces are coated with the adhesive.

9. The device of claim 1, wherein the support is translucent.

10. The device of claim 1 wherein the device is an implant.

11. The device of claim 1, further comprising one or more removable protective sheets for covering an adhesive surface of the device.

12. The device of claim 1, wherein B is an oligomer derived from polycaprolactone, polydimethylsiloxane, polypropylene glycol or polyhexamethylene carbonate, preferably polycaprolactone.

13. The device of claim 1, wherein the support comprises a polymer selected from polyesters, polylactides and polycarbonates, preferably polycaprolactone.

14. The device of claim 1, wherein the adhesive comprises two or more different compounds of structure 1 or comprises a cross-linked polymer produced by cross-linking two or more different compounds of structure 1.

15. A method of adhering a first surface and a second surface comprising:
applying an adhesive device to at least a portion of at least one of the first and second surfaces; and bringing at least a portion of the first and second surfaces into contact with each other and/or bringing at least a portion of the first and second surfaces into contact with the adhesive device
wherein the device comprises:
a support; and
a water insoluble adhesive on at least one bonding site on a surface of the support, the adhesive comprising:

a compound of structure 1

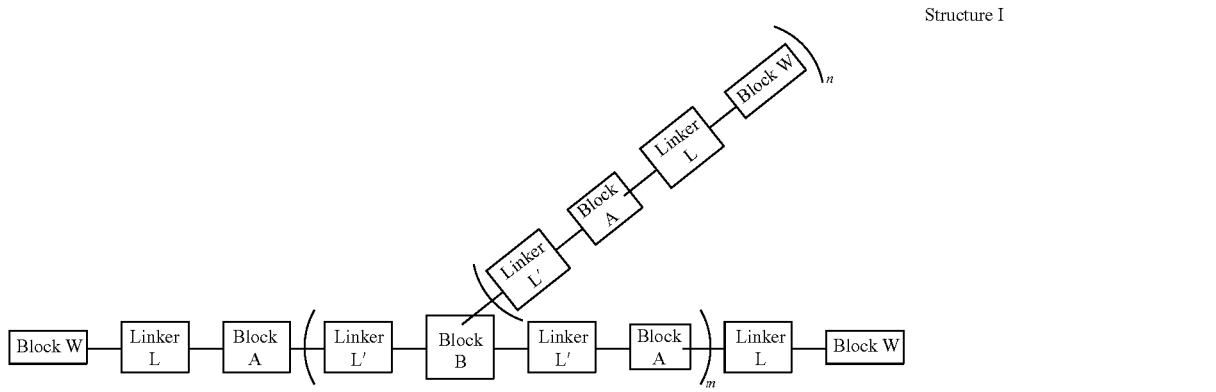
Structure I wherein the compound is water insoluble;

the compound has a Tg lower than 25° C.;

B is a branched or unbranched oligomer derived from a polyester, polyether, polyalkylene glycol, polysilicone or polycarbonate with a MW<10,000 q/mol;

Linker L is an urethane, urea bond, or amide bond;

Linker L' is an urethane or urea bond;

A is a chain extender of Mw≤3000 q/mol comprising substituted or unsubstituted alkyl, cycloalkyl and/or aromatic groups;

W is a terminal adhesive selected from an adhesive benzene-1,2-diol derivative or an adhesive benzene-1,2,3-triol derivative;

m is 0 or 1; and n is 0, 1, 2, 3 or 4; or a cross-linked polymer produced by cross-linking compounds of structure 1.

16. The method of claim 15 wherein at least one of the first and second surfaces is a wet surface, saline surface and/or a surface contaminated with proteins and/or biomolecules.

17. The method of claim 15 wherein the first surface comprises soft tissue and the second surface comprises hard tissue or a part of an implant or device.

18. The method of claim 15 wherein the first surface comprises hard tissue and the second surface comprises a part of an implant or device or hard tissue.

19. The method of claim 15 further comprising applying an external energy source to the adhesive and/or at least one of the first and second surface to enhance crosslinking in situations where crosslinkers benefit from an external energy source to facilitate complete or rapid action.

20. A method of stabilizing a surface comprising applying an adhesive device to the surface
wherein the device comprises:
a support; and
a water insoluble adhesive on at least one bonding site on a surface of the support, the adhesive comprising:
a compound of structure 1

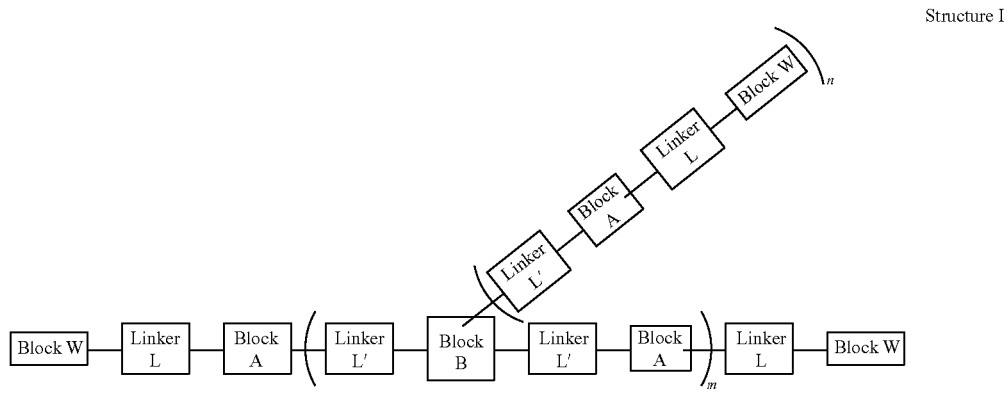
Structure I wherein the compound is water insoluble;

the compound has a Tg lower than 25° C.;

B is a branched or unbranched oligomer derived from a polyester, polyether, polyalkylene glycol, polysilicone or polycarbonate with a MW<10,000 q/mol;

Linker L is an urethane, urea bond, or amide bond;

Linker L' is an urethane or urea bond;

A is a chain extender of Mw ≤ 3000 g/mol comprising substituted or unsubstituted alkyl, cycloalkyl and/or aromatic groups;

W is a terminal adhesive selected from an adhesive benzene-1,2-diol derivative or an adhesive benzene-1,2,3-triol derivative;

m is 0 or 1; and n is 0, 1, 2, 3 or 4; or a cross-linked polymer produced by cross-linking compounds of structure 1.

* * * * *